US012681007B2

(12) United States Patent
Dong et al.

(10) Patent No.: US 12,681,007 B2
(45) Date of Patent: Jul. 14, 2026

(54) HIGH THROUGHPUT METHOD FOR CONSTRUCTING AND SCREENING COMPOUND LIBRARY AND REACTION DEVICE

(71) Applicant: ZHONGHONGXIN INVESTMENT HOLDINGS (SHENZHEN) CO., LTD., Shenzhen (CN)

(72) Inventors: Jiajia Dong, Shanghai (CN); Karl Barry Sharpless, Shanghai (CN); Genyi Meng, Shanghai (CN); Taijie Guo, Shanghai (CN); Tiancheng Ma, Shanghai (CN)

(73) Assignee: DEEPSYN. CO, Shanghai (CN)

( * ) Notice: Subject to any disclaimer, the term of this patent is extended or adjusted under 35 U.S.C. 154(b) by 1165 days.

(21) Appl. No.: 17/597,409

(22) PCT Filed: Jun. 29, 2020

(86) PCT No.: PCT/CN2020/099034
§ 371 (c)(1),
(2) Date: Jan. 5, 2022

(87) PCT Pub. No.: WO2021/004326
PCT Pub. Date: Jan. 14, 2021

(65) Prior Publication Data

US 2022/0291202 A1 Sep. 15, 2022

(30) Foreign Application Priority Data

Jul. 5, 2019 (CN) ........................ 201910605212.5

(51) Int. Cl.
*G01N 33/50* (2006.01)
*C07D 401/14* (2006.01)
*C07D 403/12* (2006.01)
*C07D 403/14* (2006.01)
*C07D 413/14* (2006.01)
*C40B 30/00* (2006.01)
*C40B 30/06* (2006.01)
*C40B 50/04* (2006.01)
*C40B 60/08* (2006.01)

(52) U.S. Cl.
CPC ....... *G01N 33/5011* (2013.01); *C07D 401/14* (2013.01); *C07D 403/12* (2013.01); *C07D 403/14* (2013.01); *C07D 413/14* (2013.01); *C40B 30/06* (2013.01); *C40B 50/04* (2013.01); *C40B 60/08* (2013.01); *B01J 2219/00315* (2013.01); *B01J 2219/00736* (2013.01)

(58) Field of Classification Search
CPC ....... C40B 50/04; G01N 33/50; G01N 3/5011
See application file for complete search history.

(56) References Cited

U.S. PATENT DOCUMENTS

2006/0172881 A1 8/2006 Devaraj
2006/0269942 A1* 11/2006 Kolb ................. A61K 51/0455 435/7.1

FOREIGN PATENT DOCUMENTS

CN 1173921 A 2/1998
CN 103421876 A 12/2013
WO 2009105746 A2 8/2009
WO WO-2013191550 A1 * 12/2013 ........... C07H 15/234

OTHER PUBLICATIONS

International Search Report issued Sep. 27, 2020 in corresponding PCT/CN2020/099034.
Written Opinion issued Sep. 27, 2020 in corresponding PCT/CN2020/099034.
Lee, L.V., et al., "A potent and highly selective inhibitor of human alpha-1, 3-fucosyltransferase via click chemistry," Journal of the American Chemical Society, American Chemical Society, vol. 125, No. 32, pp. 9588-9589, Aug. 13, 2003.
Lee, L.V., et al., "Supporting information: A potent and highly selective inhibitor of human alpha-1, 3-fucosyltransferase via click chemistry," Journal of the American Chemical Society, American Chemical Society, retrieved from the Internet: URL:http://pubs.acs.org/doi/suppl/10.1021/ja0302836/suppl_file/ja0302836_s.pdf, Jul. 22, 2003, (retrieved on Apr. 14, 2011).
Meng, Genyi, et al., "Modular click chemistry libraries for functional screens using a diazotizing reagent," Nature, Nature Publishing Group UK, London, vol. 574, No. 7776, pp. 86-89, Oct. 1, 2019.
Srinivasan, Rajavel, et al., "High-trhoughput synthesis of azide libraries suitable for direct "click" chemistry and in situ screening," Organic & Biomolecular Chemistry, vol. 7, pp. 1821-1828 (2009).

* cited by examiner

*Primary Examiner* — Amy M Bunker
(74) *Attorney, Agent, or Firm* — Ice Miller LLP

(57) ABSTRACT

The present invention provides a high throughput method for constructing and screening a compound library and a reaction device. Specifically, the method of the present invention comprises: (a) providing a reactor comprising n independent and addressable reaction chambers; (b) performing m independent synthesis reactions in said n reaction chambers, thereby constructing a compound library; and (c) performing activity tests in reaction chambers in which synthesis reactions are performed. In the present invention, the preparation and screening processes of a compound can be completed in the same reaction system. As the reactions of the present invention almost quantitatively generate products, the products can be directly used in enzymatic or even cytological activity test experiments without separation.

5 Claims, 9 Drawing Sheets

HIGH THROUGHPUT METHOD FOR CONSTRUCTING AND SCREENING COMPOUND LIBRARY AND REACTION DEVICE

CROSS-REFERENCE TO RELATED APPLICATION

This application is a Section 371 of International Application No. PCT/CN2020/099034 filed Jun. 29, 2020, which was published in the Chinese language Jan. 14, 2021, under International Publication No. WO 2021/004326 A1, which claims priority to Chinese Patent Application No. 201910605212.5 filed Jul. 5, 2019, the disclosures of which are incorporated herein by reference in their entireties.

TECHNICAL FIELD

The present invention relates to the chemical and biological fields, in particular to a high-throughput method for constructing and screening compound library and a reaction device.

BACKGROUND OF THE INVENTION

Triazole is an important five-membered nitrogen heterocyclic compound, which involves a wide range of industrial applications, such as agricultural chemicals, corrosion inhibitors, dyes, fluorescent brighteners, and bioactive agents, etc. Azide functional groups are very important and widely used in organic synthesis. However, this kind of compounds have great potential safety hazards in the process of synthesis, storage and transportation due to their high energy, which leads to difficulty in synthesis and use. At present, the synthetic methods of azide compounds are very limited, among which alkyl, acyl and sulfonyl azide are mostly obtained by nucleophilic substitution reactions with $NaN_3$ being used to replace the leaving functional groups in polar solvents, and the method need further purification, and the syn thesis efficiency is not high, resulting tedious post-treatment when used for further activity screening.

In the development of pharmaceuticals and agrochemicals, commercial compound libraries and compound libraries produced by combinatorial synthesis have been screened to find biologically active substances (such as leading compounds). However, in the synthesis of compounds used as drugs, separation and purification take a lot of time, and it is difficult to find leading compounds that can be used as drugs. The compound library produced by combinatorial chemistry is a mixture of many compounds, and the structure of products is difficult to control. In addition, in order to establish a compound library, it is necessary to identify the structure of compounds during the synthesis of compounds and their derivatives, so as to determine the suitable methods for modifying compounds and explore the reaction conditions for synthesizing derivatives. The resulting adverse result is that it takes a lot of time to synthesize compounds.

Therefore, it is necessary to develop a simple, efficient and high-throughput method for synthesizing compound libraries and screening their activities.

SUMMARY OF THE INVENTION

The invention provides a simple, efficient and high-throughput method for synthesizing a compound library and screening their activities.

In a first aspect of the invention, provided is a method for constructing and screening a high-throughput compound library comprising:

(a) providing a reactor comprising n reaction chambers, wherein the reaction chambers are each independent and addressable, and the n reaction chambers constitute an addressable array of reaction chambers;

(b) performing m each independent synthesis reactions in t e n reaction chambers, and obtaining respective synthetic products in each of reaction chambers in which the synthesis reactions are carried out, thereby constructing and obtaining a compound library;

wherein, the synthesis reaction comprises the following steps:

(b1) in a reaction chamber, in an inert solvent, carrying out a 1, 3-dipolar cycloaddition reaction with a 1, 3-dipolar cyclization reagent and a reaction substrate containing terminal unsaturated bond, thereby forming a reaction product containing 1, 3-dipolar ring;

and (c) optionally, adding activity test reagent into the reaction chamber where the synthesis reaction is carried out, respectively to carry out activity test, thereby carrying out activity screening on each synthetic product;

wherein, n is a positive integer ≥10, and m is a positive integer ≤n and m≥10.

In another preferred embodiment, in step (c), after adding activity test reagent, performing incubation so that the activity test reagent reacts or contacts with each synthesis reaction.

In another preferred embodiment, the reactor comprises an array reactor.

In another preferred embodiment, n is 20-50000, preferably 36-10000, more preferably 48-5000, most preferably 96-2500.

In another preferred embodiment, the 1, 3-dipolar cyclization reagent is $R—N_3$, where R is the molecular moiety or fragment attached to the azide group.

In another preferred embodiment, in two or more reaction chambers, performing the same synthesis reactions.

In another preferred embodiment, different synthesis reactions are carried out in each reaction chamber.

In another preferred embodiment, in the synthesis reaction, m kinds of 1, 3-dipolar cyclization reagents located in m reaction chambers respectively, are used to react with the same kind of reaction substrates containing terminal unsaturated bond.

In another preferred embodiment, the "terminal unsaturated bond" means that there is a double bond or triple bond between the terminal atom (except hydrogen atom) located at the terminal and its adjacent subterminal atom (except hydrogen atom).

In another preferred embodiment, the terminal atom and t e adjacent subterminal atom are each independently selected from the group consisting of C, N, and combinations thereof.

In another preferred embodiment, the "terminal unsaturated bond" is selected from the group consisting of C═C, C═C, C═N, and combinations thereof.

In another preferred embodiment, the reaction chamber is a micro or small reaction chamber.

In another preferred embodiment, the volume of each of the reaction chambers is independently 5 μL-5000 μL.

In another preferred embodiment, the volume of the reaction chamber is 10-2000 μL, more preferably from 20 μL-1500 μL.

In another preferred embodiment, in a single reaction chamber, the volume of the reaction system in which the synthesis reaction is carried out is 52 ml, preferably ≤1 ml, more preferably 50.6 ml.

In another preferred embodiment, in a single reaction chamber, the volume of the reaction system in which the synthesis reaction is carried out is 5-2000 μL, preferably 10-1000 μL, more preferably 20-600 μL.

In another preferred embodiment, the activity test reagent is selected from the group consisting of small molecule compounds, proteins, nucleic acids, cells and combinations thereof.

In another preferred embodiment, the activity test reagent comprises an enzyme activity test reagent composition, or a cell activity test reagent composition.

In another preferred embodiment, the activity test reagent is a compound having physiological activity, preferably selected from the group consisting of enzyme inhibitor, ligand/receptor binding inhibitor, angiogenesis inhibitor, cell adhesion inhibitor, gene expression inhibitor and growth factor-like active substance.

In another preferred embodiment, the enzyme inhibitor is elected from the group consisting of tyrosinase inhibitor, cyclooxygenase inhibitor telomerase inhibitor, matrix metalloprotein inhibitor, prostaglandin D synthesis inhibitor, phosphodiesterase inhibitor, cholinesterase inhibitor, viral protease inhibitor, reverse transcriptase inhibitor, and a combination thereof.

In another preferred embodiment, the protein comprises an antibody, a ligand, an antigen, or a combination thereof.

In another preferred embodiment, the step (c) comprises a step of detecting each of reaction chamber thereby obtaining activity test results in each chamber, respectively.

In another preferred embodiment, a step of separating or purifying the reaction product is not included between the steps (b) and (c).

In another preferred embodiment, after the end of step (b) (e.g. step (b1)), it is directly applied in step (c) for subsequent activity testing without separation.

In another preferred embodiment, in the step (b), the reaction formula for the 1, 3-dipolar cycloaddition reaction is selected from the group consisting of

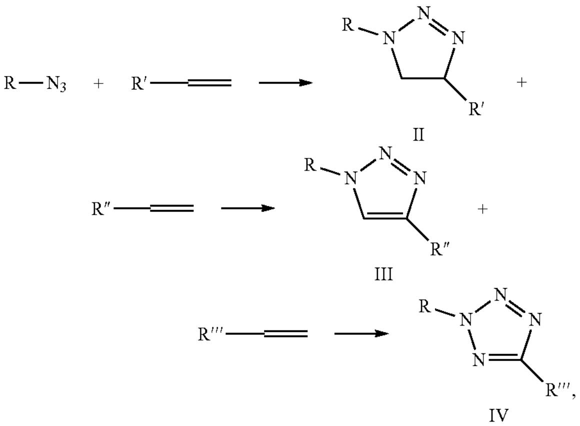

II

III

IV wherein, R, R', R'' and R'' are each independently $R^1$ or

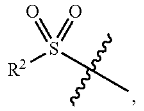

and $R^1$ and $R^2$ are each independently a substrate fragment.

In another preferred embodiment, in the step (b), the reaction formula for the 1, 3-dipolar cycloaddition reaction is as follows:

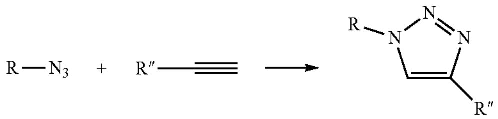

III wherein, R and R'' are each independently $R^1$ or

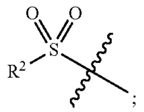

$R^1$ and $R^2$ are each independently a substrate fragment.

In another preferred embodiment, $R^1$ and $R^2$ are the remaining molecular moiety of the reaction substrate other than molecular moiety of the terminal unsaturated bond.

In another preferred embodiment, $R^1$ and $R^2$ each are independently drug active fragments.

In another preferred embodiment, $R^1$ and $R^2$ are each independently substituted or unsubstituted groups selected from the group consisting of alkyl, cycloalkyl, heteroalkyl, heterocyclyl, alkenyl, cycloalkenyl, alkynyl, aryl, heteroaryl, sulfonyl, or a combination thereof.

In another preferred embodiment, $R^1$ and $R^2$ are each independently selected from the group consisting of substituted or unsubstituted $C_1$-$C_{12}$ alkyl, substituted or unsubstituted 3-12 heteroalkyl, substituted or unsubstituted 5-16 heteroaryl, substituted or unsubstituted $C_6$-$C_{18}$ aryl, substituted or unsubstituted 3-20 heterocyclyl, substituted or unsubstituted $C_3$-$C_{12}$ cycloalkyl; wherein the "substituted" means that one or more hydrogen atoms in the groups are substituted by substituent Ra, and Ra is selected from the group consisting of halogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{12}$ cycloalkyl, oxo (i.e. =O), Rf—$SO_2$—, =NRf—CN, hydroxyl, —ORf, NRdRe, substituted or unsubstituted $C_1$-$C_6$ amino, substituted or unsubstituted —($C_1$-$C_6$ alkylene)-NH—($C_1$-$C_6$ alkylene), carboxyl, substituted or unsubstituted $C_6$-$C_{10}$ aryl, substituted or unsubstituted 5-12-membered heteroaryl having 1-3 heteroatoms, substituted or unsubstituted 5-12-membered heterocyclyl having 1-4 heteroatoms, wherein the substituent is selected from group consisting of halogen, hydroxyl, carboxyl, cyano, C1-C6 alkoxy, and C1-C6 alkylamino;

Rd, Re, Rf are each independently selected from the group consisting of H, substituted or unsubstituted $C_1$-$C_6$ alkyl, substituted or unsubstituted $C_3$-$C_{10}$ cycloalkyl, substituted or unsubstituted $C_6$-$C_{10}$ aryl, substituted or unsubstituted 5-12-membered heteroaryl having 1-3 heteroatoms, substituted or unsubstituted 5-12-membered heterocyclyl having 1-4 heteroatoms;

the "substituted" in Ra, Rd, Re and Rf means that being substituted by one or more (e.g. 2, 3, 4, etc.) substituents selected from the group consisting of halogen, $—CH_2Cl$, $—CHCl_2$, $—CCl_3$, $—CH_2F$, $—CHF_2$, $—CF_3$, $—O(CH_2)_xO(CH_2)_yCH_3$, oxo —CN, hydroxy, amino, substituted amino, carboxyl, —NHAc, a group selected from the group consisting of, which is unsubstituted or substituted by one or more substituents selected from the group consisting of, $C_1$-$C_6$ alkyl, $C_1$-$C_6$ alkoxy, $C_6$-$C_{10}$ aryl, $C_3$-$C_8$ cycloalkyl, halogenated $C_6$-$C_{10}$ aryl, 5-10-membered heteroaryl having 1-3 heteroatoms selected from N, S and O, 5-10-membered heterocyclyl having 1-3 heteroatoms selected from N, S and 0;

x is 1, 2, 3, 4, 5 or 6;

y is 0, 1, 2, 3, 4, 5 or 6;

in each of the above-mentioned formula, any one of the heteroatoms is independently selected from the group consisting of N, S and O.

In another preferred embodiment, any one of the reaction substrates and the reaction products, or the groups or atoms thereof, conforms to the relevant rules of the valence state of the compound (for example, the highest valence state of C is 4, and the highest valence state of N is 5).

In another preferred embodiment, the reaction substrates and reaction products are organic compounds.

In another preferred embodiment, the R—$NH_2$ is unprotected free amine or a salt of acid-protected amine.

In another preferred embodiment, the 1, 3-dipolar cycl addition reaction is a modular synthesis using the click chemical reaction principle.

In another preferred embodiment, the 1, 3-dipolar cyclization reagent is prepared in situ or added to the reaction chamber.

In another preferred embodiment, in the step (b), prior to step (b1), further comprises:

(b0) in an inert solvent, in the presence of a base, react ng an amine fragment (preferably R—$NH_2$) with $FSO_2N_3$ to obtain a 1,3-dipolar cyclization reagent;

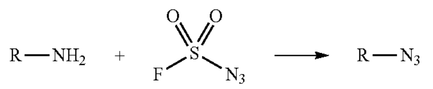

wherein, R is the molecular moiety or fragment attached to the azide group.

In another preferred embodiment, the step (b0) is performed in or out of the reaction chamber.

In another preferred embodiment, in the step (b0), reacting m different amines respectively located in m reaction chambers with $FSO_2N_3$ respectively to obtain different R—$N_3$.

In another preferred embodiment, the molar ratio of R—$NH_2$ and $FSO_2N_3$ is preferably about 1:2 to 2:1, such as about 1:1.

In another preferred embodiment, the molar ratio of the base and $FSO_2N_3$ is about 10:1 to 2:1, preferably about 4:1.

In another preferred embodiment, in the step (b0), the reaction for preparation of azide compound can be carried out at 0° C.-60%° C., preferably 25° C.-30° C.

In another preferred embodiment, the azide R—$N_3$ prepared in the step (b0) can be directly used in the subsequent 1, 3-dipolar cycloaddition reaction without separation.

In another preferred embodiment, in the step (b) (comprising steps (b0) and/or (b1)), the inert solvent is selected from the group consisting of water, nitrile solvent, alcohol solvent, aromatic solvent, haloalkane solvent, sulfur dioxide, alkane solvent, ester solvent, ketone solvent, ether solvent, sulfoxide solvents amide solvent and N-methylpyrrolidone, or a combination thereof.

In another preferred embodiment, the nitrile solvent is acetonitrile.

In another preferred embodiment, the alcohol solvent is selected from the group consisting of methanol, ethanol, tert-butyl alcohol, or a combination thereof.

In another preferred embodiment, the aromatic solvent is selected from the group consisting of benzene, toluene, trifluorotoluene, fluorobenzene, or a combination thereof.

In another preferred embodiment, the haloalkane solvent is elected from the group consisting of dichloromethane, chloroform, 1, 2-dichloroethane, or a combination thereof.

In another preferred embodiment, the alkane solvent is selected from the group consisting of petroleum ether 30-60, petroleum ether 60-90, n-hexane, or a combination thereof.

In another preferred embodiment, the ester solvent is ethyl acetate.

In another preferred embodiment, the ketone solvent is acetone.

In another preferred embodiment, the ether solvent is selected from the group consisting of methyl tert-butyl ether, 1, 4-dioxane, diethyl ether, tetrahydrofuran, or a combination thereof.

In another preferred embodiment, the sulfoxide solvent is dimethyl sulfoxide.

In another preferred embodiment, the amide solvent is N, N-dimethylformamide.

In another preferred embodiment, the solvent is a mixed solvent of an ether solvent, a sulfoxide solvent and water, or a mixed solvent of an ether solvent, a nitrile solvent and water.

In another preferred embodiment, the solvent is a mixture of methyl tert-butyl ether, dimethyl sulfoxide and water, or a mixture of methyl tert-butyl ether, acetonitrile and water.

In another preferred embodiment, when the solvent is a mixed solvent of ether solvent, sulfoxide solvent and water, the volume ratio of the ether solvent, sulfoxide solvent and water is 2-7: 10-20:0.8-1.2; preferably 5:15:1.

In another preferred embodiment, when the solvent is a mixed solvent of ether solvent, nitrile solvent and water, the volume ratio of the mixed solvent of ether solvent, nitrile solvent and water is 15-25:0.8-1.2:15-25; preferably 20:1:20.

In another preferred embodiment, in the step (b) (comprising steps (b0) and/or (b1)), the base is an inorganic base and/or an organic base.

In another preferred embodiment, when the base is an inorganic base, the inorganic base is one or more of sodium carbonate, potassium carbonate, cesium carbonate, sodium hydroxide, potassium hydroxide, sodium bicarbonate, potassium bicarbonate and potassium phosphate.

In another preferred embodiment, when the base is an organic base, the organic base is one or more of triethylamine, N, N-diisopropyl ethylamine, pyrrole, pyridine, 4-dimethylaminopyridine, sodium acetate, potassium acetate, sodium methoxide, sodium ethoxide, potassium tert-butoxide, 1, 8-diazabicycloundecan-7-ene and tetramethylethylenediamine.

In another preferred embodiment, the method further comprises: correlating the reaction substrate, reaction product, and activity test data based on the addressable address of the reaction chambers to obtain an addressable data set.

In a second aspect of the invention, provided is a high-throughput addressable reaction device, and the device comprising:

(i) a reaction module for carrying out a 1, 3-dipolar cycloaddition reaction; and the reaction module comprises at least one reactor comprising n reaction chambers, wherein the reaction chambers are each independent and addressable, and the n reaction chambers constitute an addressable array of reaction chambers, the reaction chamber is used for carrying out the 1, 3-dipolar cycloaddition reaction, resulting in the formation of a synthetic product in the reaction chamber.

wherein, n is a positive integer ≥10, and m is a positive integer ≤n and m≥10;

and (ii) optionally, an activity test module for carrying out an in-situ activity test on a synthetic product formed in the reaction chamber, thereby obtaining activity test data.

In another preferred embodiment, the reactor comprises m reaction reagents respectively located in m reaction chambers; wherein, the reaction reagent is a 1, 3-dipolar cyclization reagent or an amine precursor (i.e. an amine fragment) thereof.

In another preferred embodiment, the device further comprises (iii) an automatic pipetting module for adding a reaction reagent and/or an activity test reagent to predetermined each of addressable reaction chambers.

In another preferred embodiment, the device further comprises (iv) a processor for controlling one or more of the reaction module, the activity test module, and the automatic pipetting module.

In another preferred embodiment, the processor is also used for correlating the reaction substrate, the reaction product, and the activity test data based on the addressable address of the reaction chamber to obtain an addressable data set, and sending or storing the data set.

In another preferred embodiment, the reactor is selected from the group consisting of a microplate, an array of PE tubes, an array of test tubes, an array of reaction flasks, or a combination thereof.

In another preferred embodiment, the reactor is an array reactor.

In a third aspect of the invention, provided is a method for constructing a compound library, comprising the steps of:

(1) using the high-throughput addressable reaction device escribed in the second aspect to construct the compound library.

In another preferred embodiment, the step (1) comprises the steps of:

(1a) when the reaction reagent is an amine fragment, reacting $FSO_2N_3$ with amine fragment compounds in each reaction chamber to prepare 1, 3-dipolar cyclization reagent, thereby obtaining a first compound library composed of 1, 3-dipolar cyclization reagent; and (1b) optionally, in the reaction chamber, reating the reaction substrates containing terminal unsaturated bonds with the 1, 3-dipolar cyclization r agents respectively to form 1, 3-dipolar ring compounds, thereby obtaining a second compound library composed of the 1, 3-dipolar ring compounds.

In another preferred embodiment, the method further comprises:

(2) carrying out activity test in situ in the reaction chamber on the 1, 3-dipolar ring compound in the second compound library.

A fourth aspect of the invention provides a use of a high-throughput addressable reaction device according to the second aspect for one or more uses selected from the group consisting of a) synthesizing different compounds simultaneously;

b) high throughput (HTS) random screening of physiologically active compounds;

c) searching for drugs or agricultural chemicals; and d) searching for leading compounds for drugs or agrochemicals.

It should be understood that in the present invention, any of the technical features specifically described above and below (such as in the Example can be combined with each other, thereby constituting new or preferred technical solutions. Limited by space, it will not be repeated here.

DETAILED DESCRIPTION OF THE INVENTION

Figure 1:
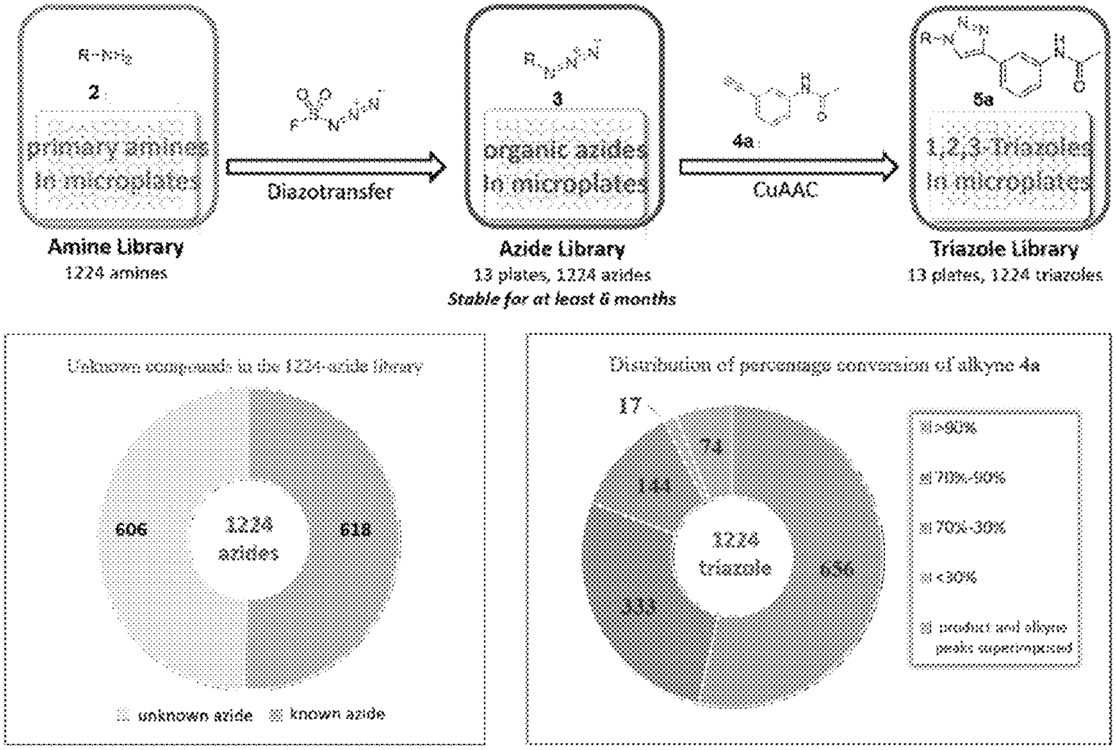
FIG. 1 shows libraries of 1224 azide compounds and libraries of 1224 triazole compounds prepared from primary amine compound libraries.
Figure 2A:
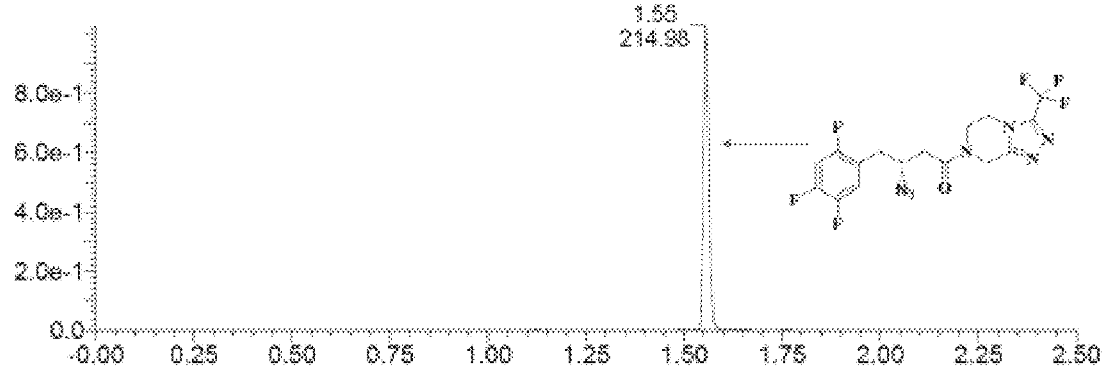
FIGS. 2*a-f* show an exemplary UPLC chromatography for preparing an azide library from a primary amine library.
Figure 2B:
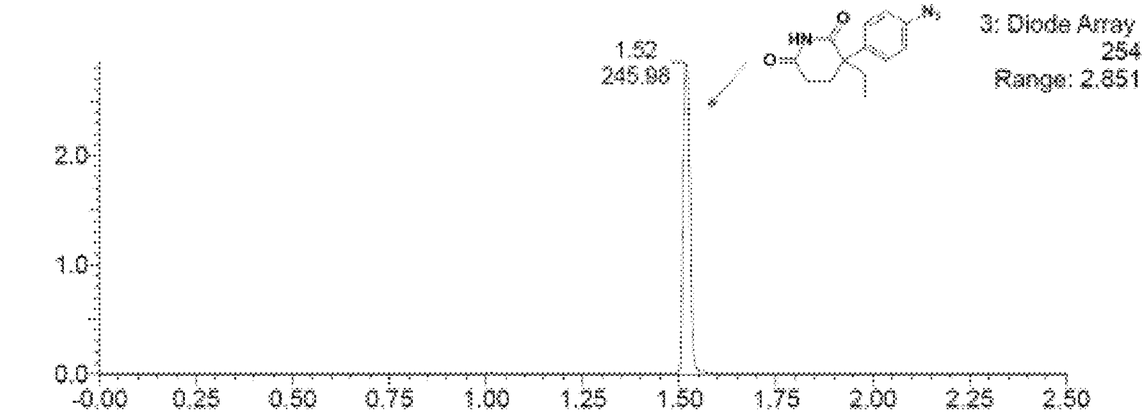
Figure 2C:
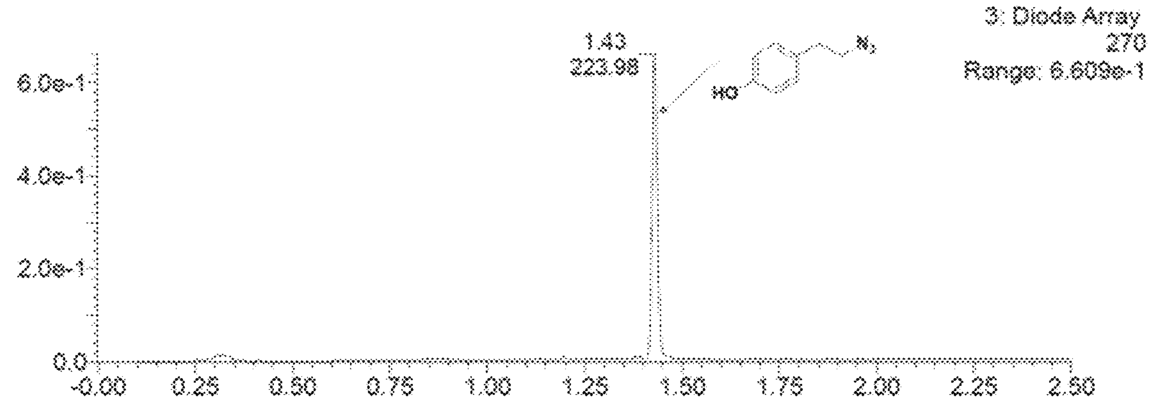
Figure 2D:
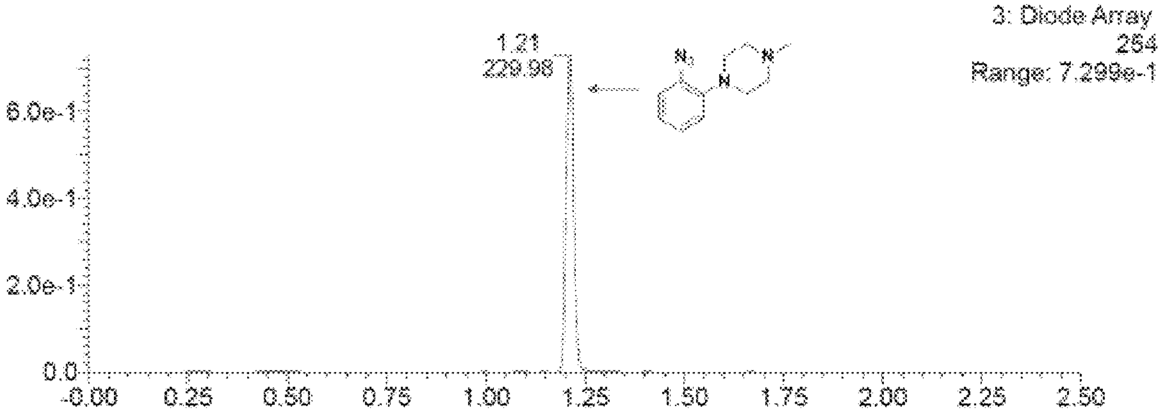
Figure 2E:
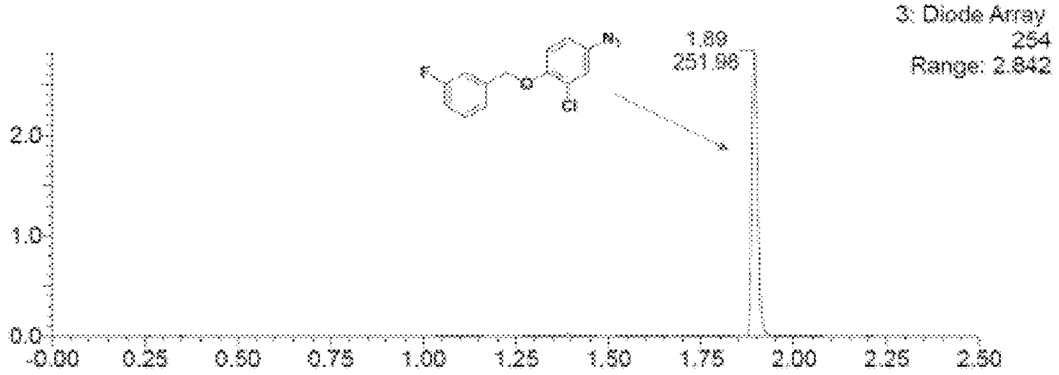
Figure 2F:
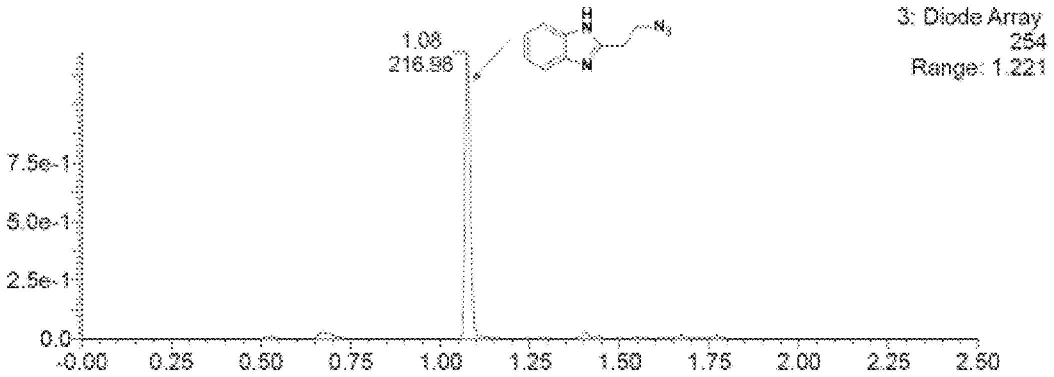
Figure 3A:
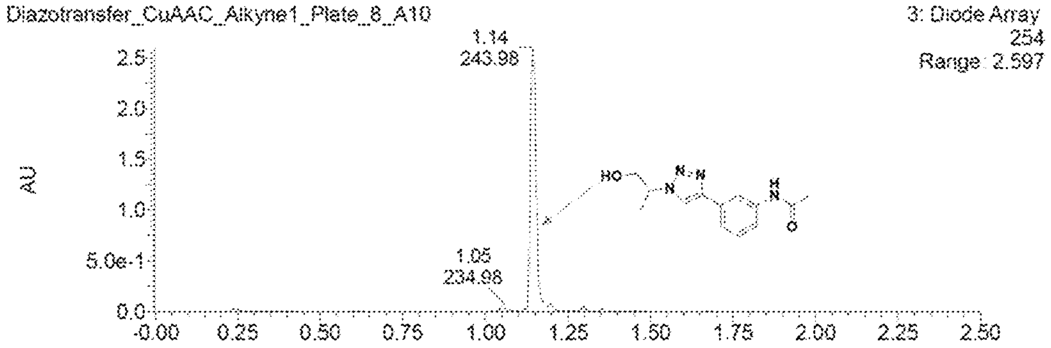
FIGS. 3*a-f* show exemplary UPLC chromatography of an azide library with copper-catalyzed azide-terminated acetylene (4a) cycloaddition (CuAAC).
Figure 3B:
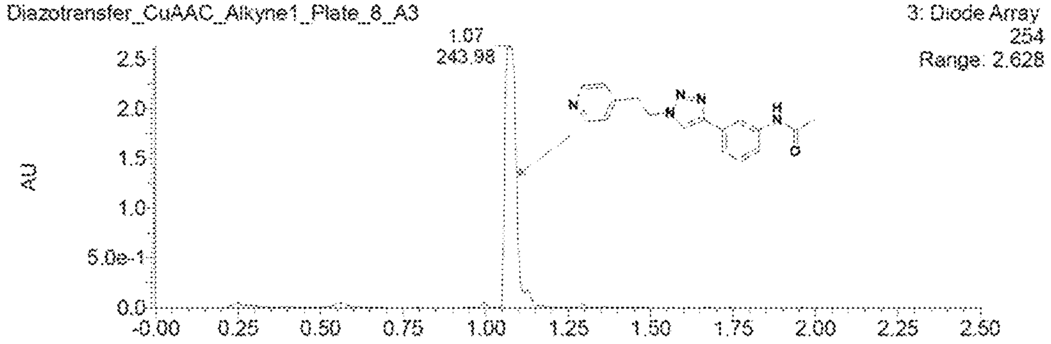
Figure 3C:
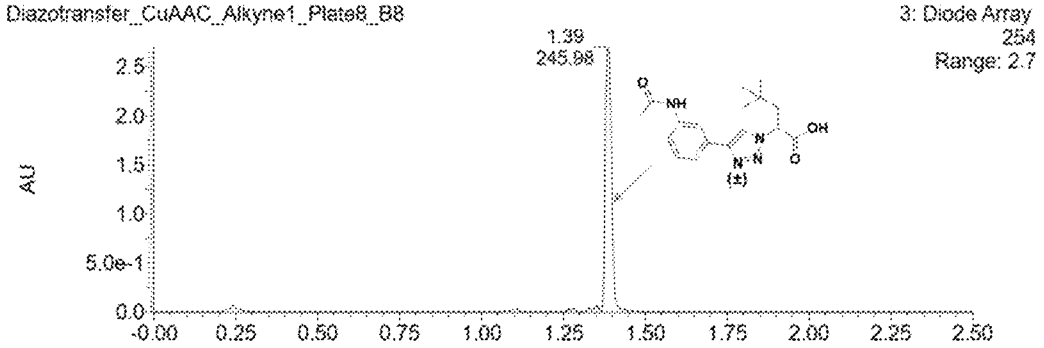
Figure 3D:
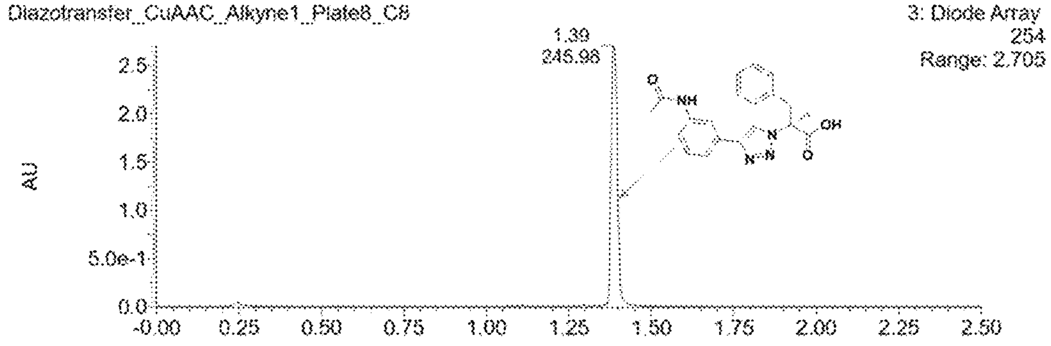
Figure 3E:
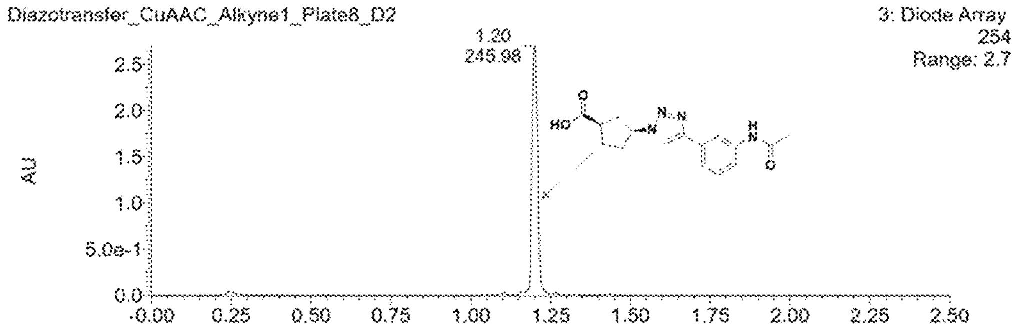
Figure 3F:
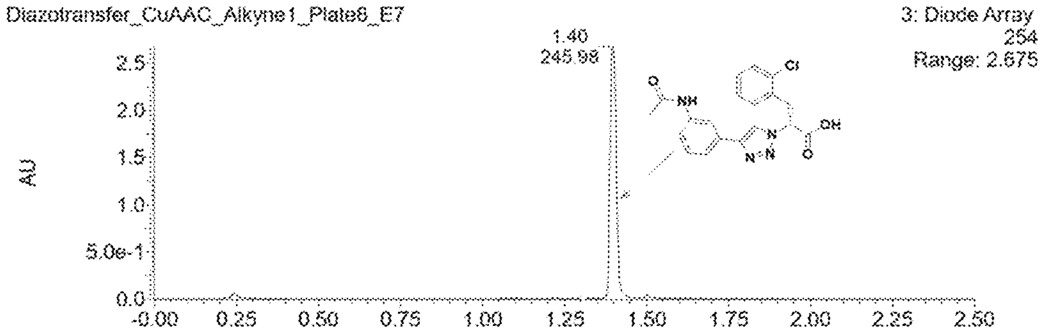
Figure 4A:
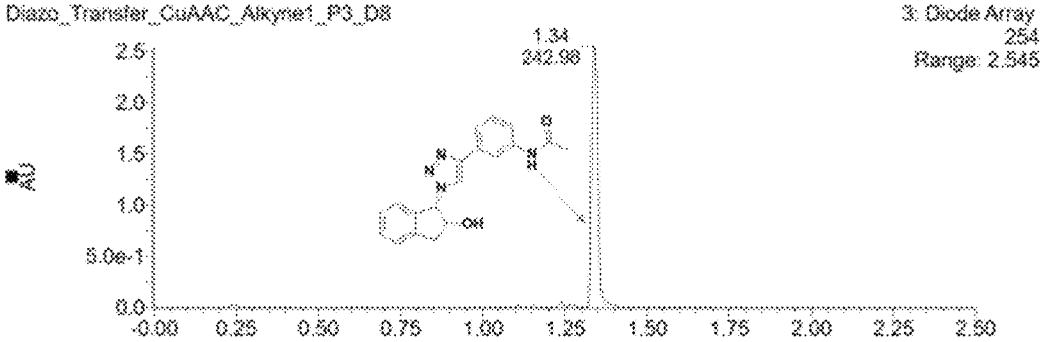
FIGS. 4*a-i* show exemplary UPLC chromatography that a library of primary amine compounds directly results in a library of 1, 2, 3-triazole compounds by copper-catalyzed azide-terminated acetylene (4a) cycloaddition (CuAAC).
Figure 4B:
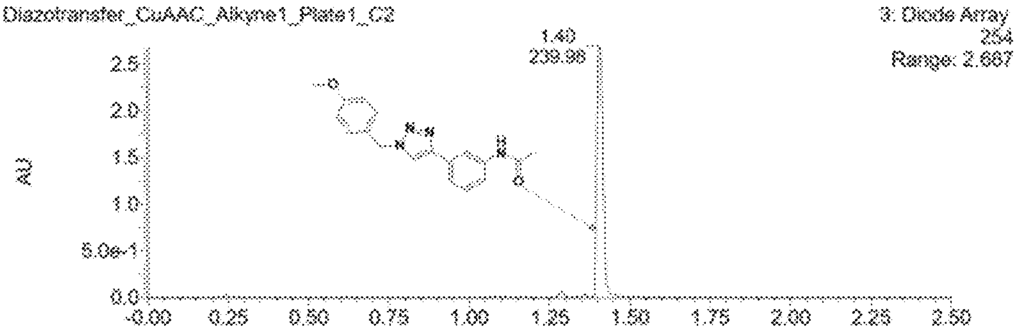
Figure 4C:
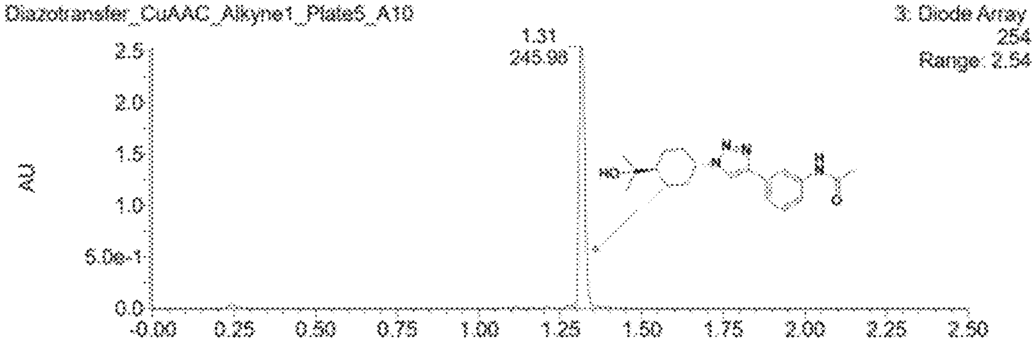
Figure 4D:
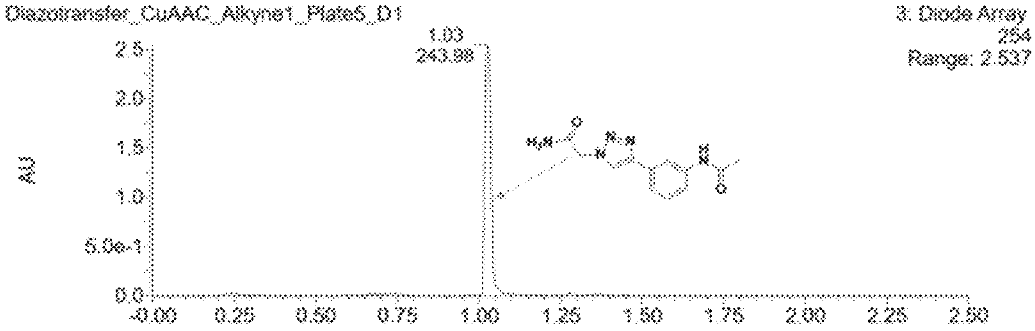
Figure 4E:
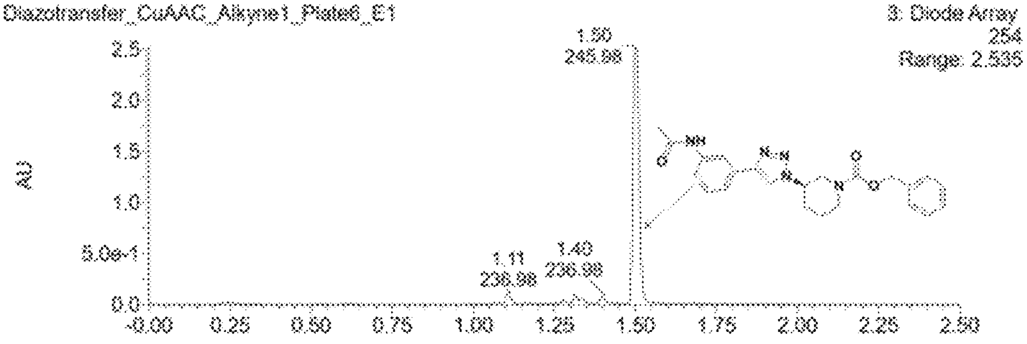
Figure 4F:
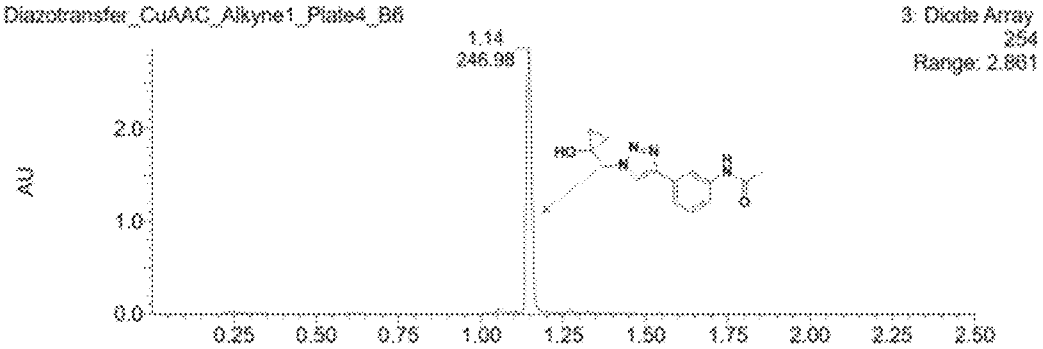
Figure 4G:
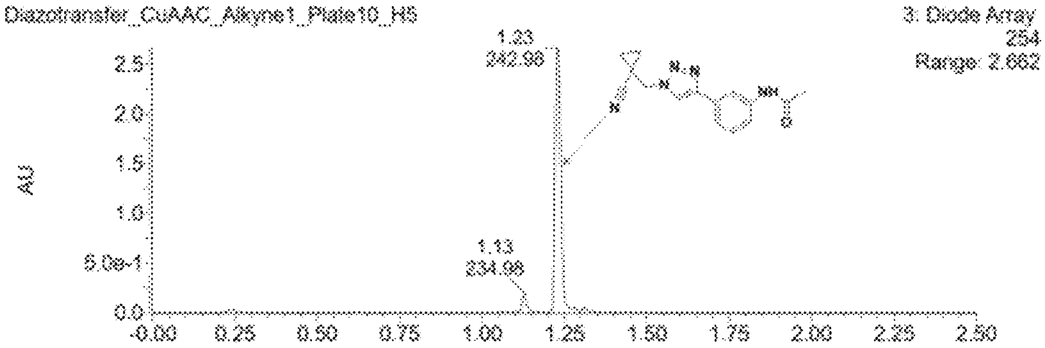
Figure 4H:
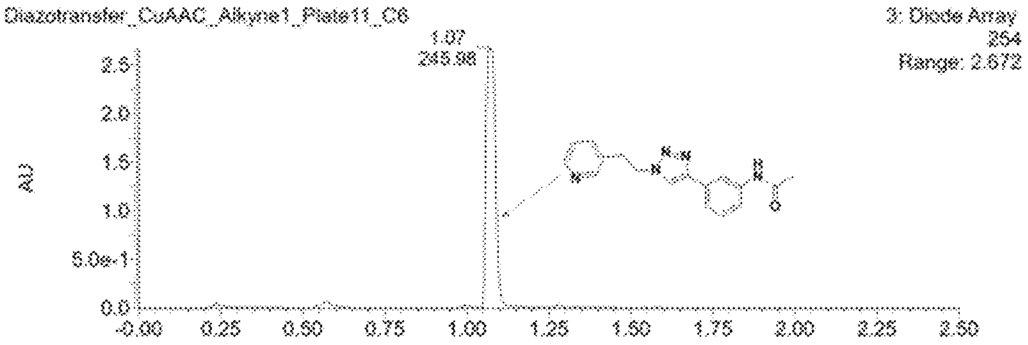
Figure 4I:
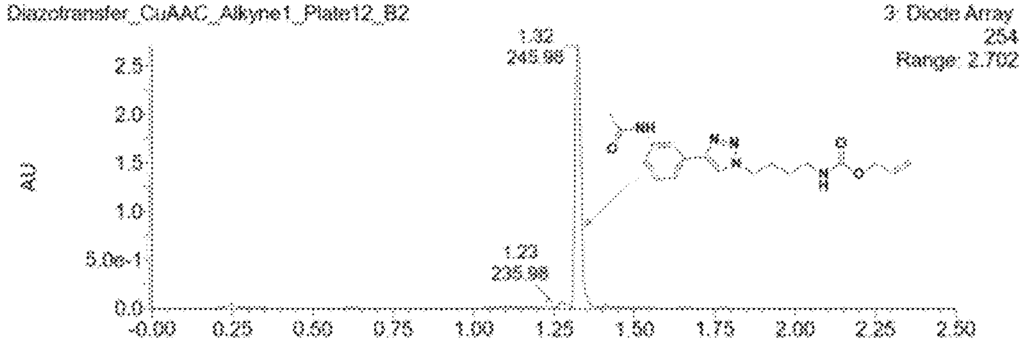
Figure 5A:
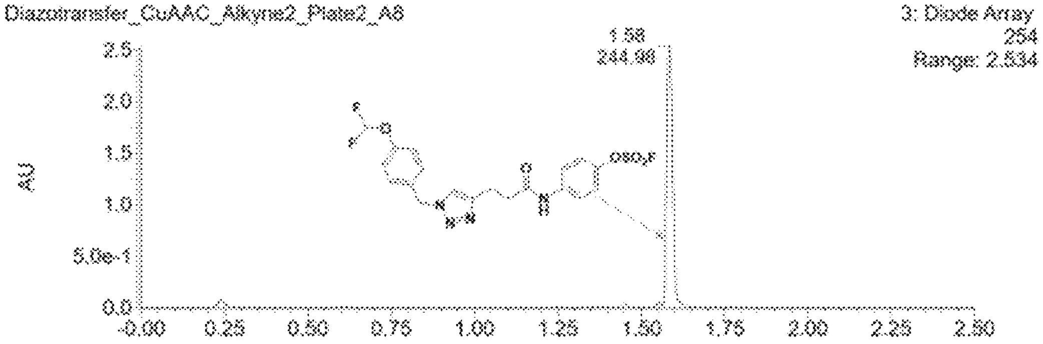
FIGS. 5*a-d* show exemplary UPLC chromatography that a library of primary amine compounds directly results in a library of 1, 2, 3-triazole compounds by diazotransfer and copper-catalyzed azide-terminated alkynes (4b) cycloaddition (CuAAC).
Figure 5B:
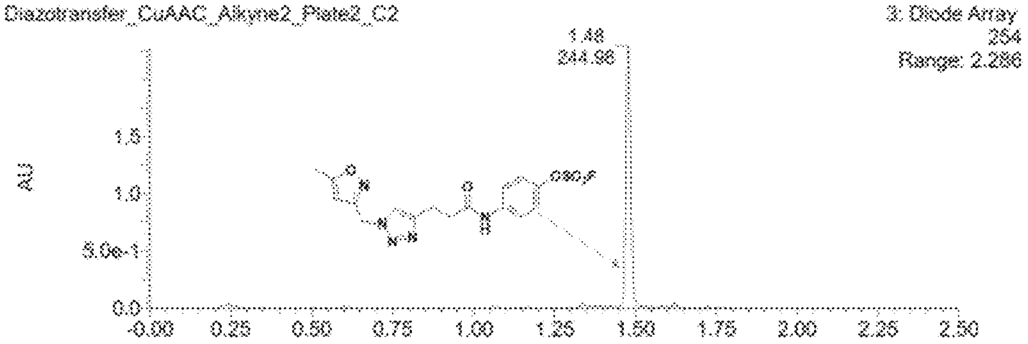
Figure 5C:
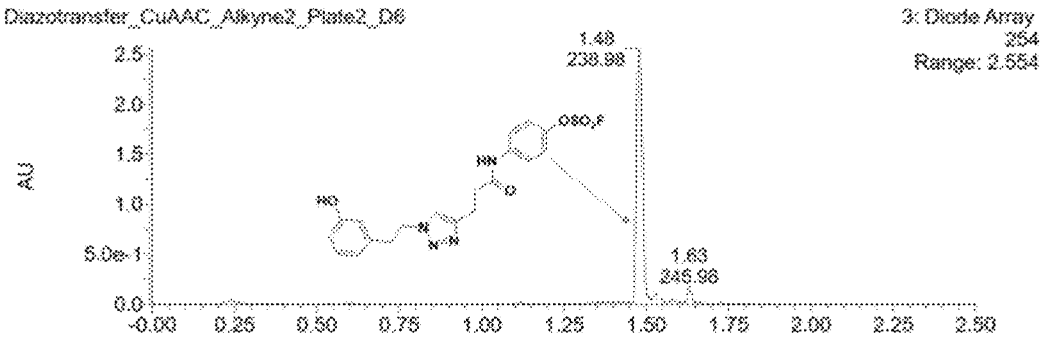
Figure 5D:
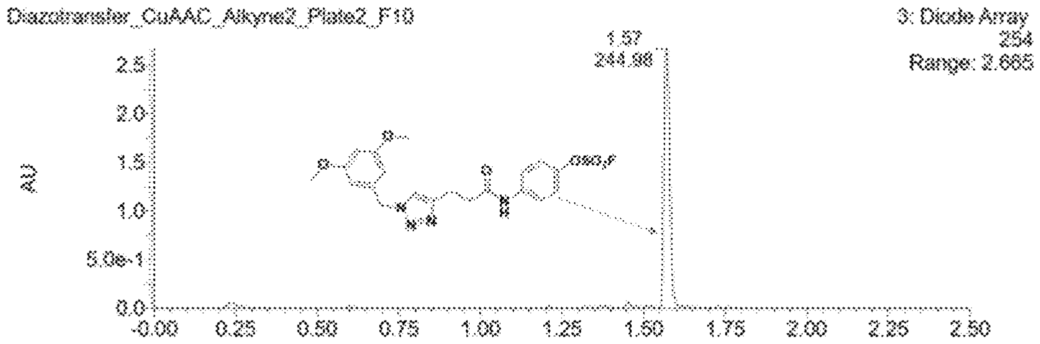

Through extensive and in-depth research, the present inventors have developed a high throughput method for constructing and screening a compound library and a device for the method for the first time. In the method of the invention, n addressable reaction chamber array formed by a plurality of independent and addressable reaction chambers is adopted for the first time, and specific synthetic reaction are independently carried out in each reaction chamber, thus a large number of different reaction products with well-defined structures could be prepared in high throughput and a high throughput compound library could be obtained. Unexpectedly, the experiment shows that subsequent compound activity determination in situ can be directly carried out in the addressable reaction chamber array (or corresponding compound library) containing the reaction product without separation and purification, thus greatly improving the construction and screening efficiency of compound library. On this basis, the present invention was completed.

In a preferred embodiment, the present inventor employs reaction chamber array to synthesize thousands of different 1, 3-dipolar ring reagents in high throughput (as a library of azides, or a first compound library), and then thousands of different 1, 3-dipolar ring reaction products (as triazole derivative library, or a second compound library) were synthesized in high throughput. Through in-situ activity screening of the compound library of the invention, the discovery of leading compound of drug is greatly accelerated, the screening speed is improved, and the development and research cycle of new inhibitors are shortened (which can be shortened from several years to several weeks or several days).

Terms

As used herein, the "reaction chamber" is any kind of devices capable of carrying out chemical reactions, including but not limited to micropore of microplate, PE tube, test tube, reaction flask, etc.

Definitions of standardized terms can be found in references including Carey and Sundberg "ADVANCED ORGANIC CHEMISTRY 4TH ED." Vols. A (2000) and B (2001), Plenum Press, New York. Unless otherwise indicated, conventional methods within the scope of the art, such as mass spectrometry, NMR, IR and UV/VIS spectroscopy and pharmacological methods are employed. Unless otherwise indicated, terms used herein in the description of analytical chemistry, organic synthetic chemistry and pharmaceutical and pharmaceutical chemistry are known in the art. For example, the reaction and purification may be carried out using the manufacturer's instructions for the use of the kit or in a manner well known in the art or in accordance with the instructions of the present invention. The above-described techniques and methods may generally be practiced in accordance with conventional metho s well known in the art in accordance with the description in a plurality of summary and more specific documents cited and discussed in this specification. In this specification, groups and their substituents may be selected by those skilled in the art to provide stable structural moieties and compounds.

When a substituent is described by a conventional chemical formula written from left to right, the substituent also includes a chemically equivalent substituent obtained by writing a structural formula from right to left. For example, $—CH_2O—$ is equivalent to $—OCH_2—$.

The chapter headings used in this article are for organizational purposes only and should not be construed as limiting the subject matter. All documents or portions of documents cited in the present application including but not limited to patents, patent applications, articles, books, manuals and papers are incorporated herein by reference in their entirety.

Certain chemical groups defined herein are preceded by simplified symbols to indicate the total number of carbon atoms present in that group. For example, C1-C6 alkyl is an alkyl having a total of 1 to 6 carbon atoms as defined below. The total number of carbon atoms in the simplified symbol does not include carbon that may be present in the substituent of the group.

In addition to the foregoing, when used in the specification and claims of present application, the following terms have the following meanings unless otherwise specifically indicated.

As used herein, the term "halogen" refers to fluorine, chlorine, bromine or iodine.

"Hydroxyl" refers to —OH.

"Carbonyl" refers to —C(═O)—.

"Cyano" refers to —CN.

"Amino" refers to $—NH_2$.

"Substituted amino" refers to an amino substituted with one or two alkyl, alkylcarbonyl, aralkyl, heteroaralkyl as defined below, for example, monoalkylamino, dialkylamino, alkylamido, aralkylamino, heteroaralkylamino.

"Carboxyl" refers to —COOH.

As used herein, as a group or part of other group (for example, in halogen-substituted alkyl), the term "alkyl" refers to a fully saturated straight or branched hydrocarbon chain group consisting only of carbon and hydrogen atoms, having for example 1 to 12 (preferably 1 to 8, preferably 1 to 6) carbon atoms, and connected to the rest of the molecule by a single bond. Examples include but not limited to methyl, ethyl, n-propyl, isopropyl, n-butyl, isobutyl, sec-butyl, tert-butyl, n-amyl, 2-methyl-butyl, 2, 2-dimethyl-propyl, n-hexyl, heptyl, 2-methyl-hexyl, 3-methyl-hexyl, octyl, nonyl and decyl, etc. Examples of cycloalkyl include monocycloalkyl or polycycloalkyl such as cyclopropyl, cyclobutyl, cyclopentyl, cyclohexyl, cycloheptyl, cyclooctyl, cyclononyl and cyclodecyl.

"Alkylene" is used alone or in combination words such as optionally substituted alkylene to denote the same group as "alkyl" as defined above, except that another hydrogen is removed to form a divalent group. It should be understood that the optional substituent may be attached to or form part of the alkylene chain.

"Alkenyl" used alone or in combination words such as "optionally substituted alkenyl" denotes a group formed from a straight-chain, branched or cyclic olefin, including an ethylene mono-, di- or polyunsaturated alkyl or cycloalkyl, preferably a C2-6 alkenyl, as defined above. Examples of the alkenyl include vinyl, allyl, 1-methylvinyl, butenyl, isobutenyl, 3-methyl-2-butenyl, 1-pentenyl, cyclopentenyl, 1-methylcyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1, 3-butadienyl, 1, 4-pentadienyl, 1, 3-cyclopentadienyl, 1, 3-hexadienyl, 1, 4-hexadienyl, 1, 3-cyclohexadienyl, 1, 4-cyclohexadienyl, 1, 3-cycloheptadienyl, 1,3, 5-cycloheptrienyl and 1, 3, 5, 7-cyclooctatetraenyl.

"Alkynyl" used alone or in combination words such as "optionally substituted alkynyl" denotes a group formed from a straight, branched or mono-, di- or polycyclic alkyne, preferably a C2-6 alkynyl. Examples of alkynyl include ethynyl, 1-propynyl, 1- and 2-butyynyl, 2-methyl-2-propynyl, 2-pentynyl, 3-pentynyl, -pentynyl, 2-hexynyl, 3-hexynyl, 4-hexynyl, 5-hexynyl, 10-undecynyl, 4-ethyl-1-octy 1-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl, and the like.

As used herein, the term "heteroalkyl" as a group or part of other group means a fully saturated straight or branched hydrocarbon chain group consisting of 2 to 14 carbon atoms and 1 to 6 heteroatoms selected from the group consisting of nitrogen, phosphorus, oxygen and sulfur. The nitrogen, carbon or sulfur atoms in the heteroalkyl can be optionally oxidized; the nitrogen atoms can optionally be quaternized.

As used herein, the term "heterocyclyl" as a group or part of other means a stable 3 to 20 nonaromatic cyclic group consisting of 2 to 14 carbon atoms and 1 to 6 heteroatoms selected from the group consisting of nitrogen, phosphorus, oxygen and sulfur. Unless otherwise specifically specified in this specification, the heterocyclyl may be a monocyclic, bicyclic, tricyclic, or more ring system, which may include a fused ring system, a bridge ring system, or a spiro ring system. The nitrogen, carbon or sulfur atoms in the heterocyclyl are optionally oxidized. The nitrogen atom can optionally be quaternized. And the heterocyclyl can be partially or completely saturated.

Heterocyclyl can be connected to the rest of the molecule via carbon atoms or heteroatoms and through single bond. Among the heterocyclyl containing fused rings, one or more of the rings may be aryl or heteroaryl as defined below, provided that the connection point with the rest of the molecule is a non-aromatic ring atom. For purposes of the present invention, the heterocyclyl is preferably a stable 4-11 membered non-aromatic monocyclic, bicyclic, bridged or spiro group containing 1 to 3 heteroatoms selected from nitrogen, oxygen and sulfur, and more preferably a stable 4-8 non-aromatic monocyclic, bicyclic, bridged or spiro group containing 1 to 3 heteroatoms selected from nitrogen, oxygen and sulfur. Examples of heterocyclic groups include, but are not limited to pyrrolidinyl, morpholinyl, piperazinyl, homopiperazinyl, piperidinyl, thiomorpholinyl, 2, 7-diaza-spiro [3.5]nonan-7-yl, 2-oxa-6-aza-spiro [3.3]heptan-6-yl, 2,5-diaza-bicyclo[2.2.1]heptan-2-yl, a etidinyl, pyranyl, tetrahydropyranyl, thiopyranyl, tetrahydrofuranyl, oxazinyl, dioxycyclopentyl, tetrahydroisoquinolinyl, decahydroisoquinolinyl, imidazoinyl, imidazolidinyl, quinazinyl, thiazolidinyl, isothiazolidinyl, isoxazolidinyl, indolnyl, octahydroindolinyl, octahydroisoindolinyl, pyrrolidinyl, pyrazolidinyl, phthalimido and the like.

As used herein, the term “aryl” as a group or a part of other group means a conjugated hydrocarbon ring system group having 6 to 18 carbon atoms (preferably 6 to 10 carbon atoms). For the purposes of the invention, the aryl may be a ring system of monocyclic, bicyclic, tricyclic or more rings and may also be fused with a cycloalkyl or heterocyclyl as defined above, provided that the aryl is connected to the rest of the molecule by a single bond via an atom on the aromatic ring. Examples of the aryl include, but are not limited to phenyl, naphthyl, anthryl, phenanthryl, fuorenyl, 2, 3-dihydro-1H-isoindolyl, 2-benzoxazolinone, 2H-1, 4-benzoxazin-3 (4H)-keto-7-yl, and the like.

As used herein, the term “heteroaryl” as a group or part of other group means a 5- to 16-membered conjugated ring group having 1 to 15 carbon atoms (preferably 1 to 10 carbon atoms) and 1 to 6 heteroatoms selected from nitrogen, oxygen and sulfur in the ring. Unless otherwise specifically specified in this specification, the heteroaryl may be a ring system of monocyclic, bicyclic, tricyclic or more rings and may also be fused with a cycloalkyl or heterocyclyl as defined above, provided that the heteroaryl is connected to the rest of the molecule by a single bond via an atom on the aromatic ring.

The nitrogen, carbon or sulfur atoms in the heteroaryl can be optionally oxidized; the nitrogen atoms can optionally be quaternized. For purposes of the present invention, the heteroaryl is preferably a stable 5- to 12-membered aromatic group comprising 1 to 5 heteroatoms selected from nitrogen, oxygen and sulfur, and more preferably a stable 5- to 10-membered aromatic group comprising 1 to 4 heteroatoms selected from nitrogen, oxygen and sulfur or a 5- to 6-membered aromatic group comprising 1 to 3 heteroatoms selected from nitrogen, oxygen and sulfur. Examples of heteroaryl include but are not limited to thienyl, imidazolyl, pyrazolyl, thiazolyl, oxazolyl, xadiazolyl, isoxazolyl, pyridyl, pyrimidyl, pyrazinyl, pyridazinyl, benzimidazolyl, b nzopyrazolyl, indolyl, furyl, pyrrolyl, triazolyl, tetrazolyl, triazinyl, indazinyl, isoindolyl, indazolyl, isoindazolyl, purinyl, quinolinyl, isoquinolinyl, diazanaphthyl, naphthyridyl, quinoxolinyl, pterridinyl, carbazolyl, carbolinyl, phenanthridinyl, phenanthrolinyl, acridinyl, phenazinyl, isothiazolyl, benzothiazolyl, benzothiophenyl, oxtriazolyl, cinolinyl, quinazolinyl, phenylthio, indolizinyl, o-diazophenyl, isoxazolyl, phenoxazinyl, phenothiazinyl, 4, 5, 6, 7-tetrahydrobenzo [b] thienyl, naphthopyridyl, [1, 2, 4]triazolo [4, 3-b]pyridazinyl, [1, 2, 4]triazolo[4, 3-b]pyrzinyl, [1, 2, 4]triazolo [4, 3-c]pyrimidinyl, [1, 2, 4]triazolo[4, 3-a]pyridinyl, imidazolo [1, 2-a]pyridinyl, imidazolo [1,2-b]pyridinyl, imidazolo [1,2-b]pyridazin 1, imidazolo [1, 2-a]pyrazinyl, etc.

As used herein, “optionally” or “substituted or unsubstituted” means that a subsequently described event or condition may or may not occur, and that the description includes both the occurrence and non-occurrence of the event or condition.

For example, “optionally substituted aryl” means substituted or unsubstituted aryl, and the description includes both substituted and unsubstituted aryl. The “optional” substituent as described in the claims and specification sections of the present invention is selected from the group consisting of alkyl, alkenyl, alkynyl, halogen, haloalkyl, haloalkenyl, haloalkynyl, cyano, nitro, optionally substituted aryl, optionally substituted heteroaryl, optionally substituted cyclic hydrocarbon, optionally substituted heterocyclic hydrocarbon.

As used herein, the term “substrate fragment” refers to the molecular portion of a reaction substrate other than a functional group (e. g., an unsaturated bond) involved in a particular reaction.

As used herein, the terms “moiety”, “structural moiety”, “chemical moiety,” “group” and “chemical group” refer to a particular fragment or functional group in a molecule. Chemical moieties are usually regarded as chemical entities embedded or attached to molecules.

Construction and Application of Compound Library

In a preferred embodiment of the present invention, a synthesis reaction based on CuAAC is employed to realize chemical connection between two molecules, thereby constructing a compound library in high throughput.

Because of the simplicity and high efficiency of the method of the invention, the diazotransfer can have certain industrial practicability even in a small laboratory. For example, in the case of obtaining 1000 primary amines, a person can construct a library of 1000 primary amine compounds with a concentration of 0.1 mol/L within 2 weeks, and the 1000 primary amine compounds can be azidated in one day, thus constructing an azide compound library containing 1000 azide compounds. The 1000 azide compounds can react with terminal alkynyl compounds, for example, 100 terminal alkynyl compounds to obtain 100, 000 triazole compounds which can be directly used for subsequent activity screening. Compared to conventional compound libraries produced by combinatorial chemistry, the compound libraries constructed by the present invention contain mainly one compound in each reactor, rather than a mixture of many compounds, and are easy to control.

The structures of the compounds in the library can be analyzed by any known structural analyse methods, such as mass spectrometry, tandem mass spectrometry, ultraviolet/visible absorption spectroscopy, proton nuclear magnetic resonance spectroscopy, $C^{13}$ nuclear magnetic resonance spectrum, infrared absorption spectrum and X-ray diffraction crystal spectrum, or their combination.

The invention provides a method for constructing and screening a high-throughput compound library, which can simultaneously synthesize different compounds in large quantities at one time, and the constructed compound library can be used for high-throughput (HTS) random screening, searching for drugs or agricultural chemicals, searching for leading compounds of drugs or agricultural chemicals, etc.

For example, in order to obtain compounds with physiological activity, the compound library can be used for various screening. Example of compounds having physiological activity include, but are not limited to enzyme inhibitor, ligand/receptor binding inhibitor, angiogenesis inhibitor, cell adhesion inhibitor, gene expression inhibitor and growth factor-like active substance. Examples of enzyme inhibitors include tyrosinase inhibitor, cyclooxygenase inhibitor, telomerase inhibitor, matrix metalloprotein inhibitor, prostaglandin D synthesis inhibitor, phosphodiesterase inhibitor, cholinesterase inhibitor, viral protease inhibitor and reverse transcriptase inhibitor. Examples of receptors include adrenergic receptor, histamine receptor, leukotriene receptor and opioid receptor.

1, 3-Dipolar Ring Reagent

In the present invention, a 1, 3-dipolar cyclization reaction is carried out on a substrate fragment having an unsaturated bond at the terminal with a 1, 3-dipolar ring reagent to obtain a compound containing a 1, 3-dipolar ring structure, such as a triazole compound. Exemplary reaction routes are as follows:

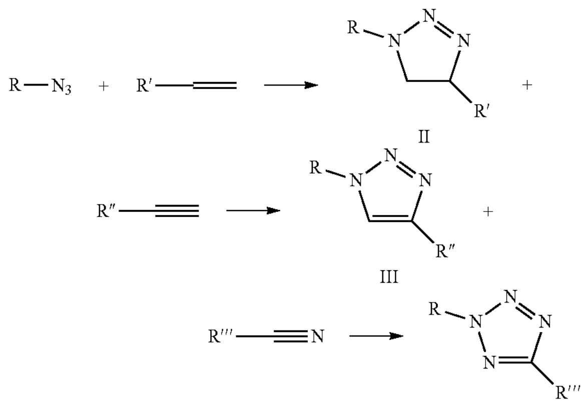

II

III

IV wherein, R, R', R" and R'" are each independently $R^1$ or

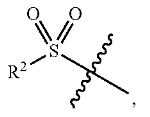

and $R^1$ and $R^2$ are each independently a substrate fragment.

In the present invention, $R^1$ and $R^2$ are the remaining molecular moiety of the reaction substrate other than the molecular moiety of the terminal unsaturated bond.

Preferably, $R^1$ and $R^2$ each are independently drug active fragments from drug molecules.

In the present invention, there is no particular limitations for R, R', R" and R'" or corresponding $R^1$ and $R^2$, they can be a variety of suitable organic groups. Typically, the representative Rand $R^2$ include organic groups formed of elements such as C, H, O, N, S, F, Cl, etc., such as a molecular moiety consisting of substituted or unsubstituted groups selected from the group consisting of alkyl, cycloalkyl, heteroalkyl, heterocyclyl, alkenyl, cycloalkenyl, alkynyl, aryl, heteroaryl, sulfonyl, or a combination thereof.

Although exemplary R, R', R" and R'" are enumerated in the present invention, it should be understood that any compound having an azide structure can be used as a 1, 3-dipolar cyclization agent of the present invention for reacting with a substrate having an unsaturated group (e.g. alkenyl, alkynyl, cycloalkenyl, cyano etc.) at the terminal to obtain a compound containing nitrogen heterocycle.

A particularly preferred type of substrate is a drug molecule (e.g. erlotinib molecule) known in the art or a known drug molecule modified y an unsaturated group.

In preferred embodiments, the modification may be obtained by means of methods known in the art, using inverse synthetic analysis, for example, modification of unsaturated groups may be performed using coupling reactions known in the art (e.g. Suzuki reaction, etc.).

1, 3-Dipolar Cyclization Reagent (Azide Compound)

In the present invention, an azide compound used as a 1, 3-dipolar cyclization reagent can also be prepared by reacting an amine fragment with a fluorosulfonyl azide.

Exemplary reactions are as follows:

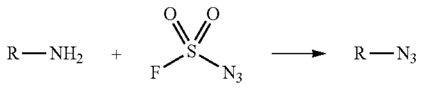

wherein the substituent R may be all substituted or unsubstituted alkyl, cycloalkyl, heteroalkyl, heterocyclyl, alkenyl, cycloalkenyl, alkynyl, aryl, heteroaryl, sulfonyl, or a combination thereof. See the definitions of R, R', R" and R'" above for the exemplary definitions of R.

Although the present invention enumerates an exemplary R group, it should be understood that any substrate with a primary amine structure can be used as an amine fragment of the present invention for constructing an azide compound as a 1, 3-dipolar cyclization agent under the process of the present invention. It should be understood that due to the abundance of primary amine compounds in nature, the method can be carried out using any existing primary amine fragment or any subsequently developed primary amine fragment.

The main advantages of the present invention include:

1 The reaction is simple and efficient, and hundreds or thousands of structure well-defined compounds can be rapidly synthesized on a large scale, thus obtaining an addressable library of compounds.

2. The library of 1, 3-dipolar cyclization reagent and 1, 3-dipolar ring reagent can be constructed quickly.

3. Compared to conventional compound libraries produced by combinatorial chemistry, the compound libraries constructed by the present invention contain mainly one compound in each reactor, rather than a mixture of many compounds, and are easy to control.

4. The high-throughput method for constructing and screen ng a compound library of the present invention can be applied to fragment-based drug discovery because the stoichiometric reagents are almost quantitative.

5. The high-throughput method for constructing and screening a compound library of the present invention can be directly applied to activity research or even phenotype screening, which cannot be realized by previous combinatorial chemistry.

The present invention will be further illustrated below with reference to the specific examples. It should be understood that these examples re only to illustrate the invention but not to limit the scope of the invention. The experimental methods without specific conditions in the following examples usually follow conventional conditions, or according to the conditions recommended by the manufacturer. Unless otherwise stated, percentage and parts are calculated by weight.

Example 1

Preparation of fluorosulfonyl azide ($FSO_2N_3$)

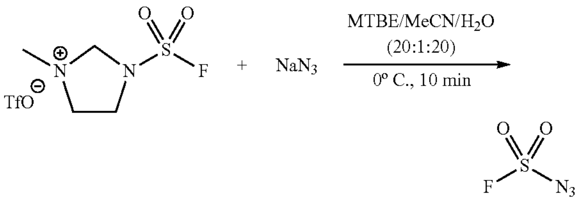

1-(fluorosulfonyl)-2, 3-dimethyl-1H-imidazole trifluoromethanesulfonate in acetonitrile (6 mmol, 1 ml MeCN) was added to a mixed system of sodium azide aqueous solution (0.25 M, 20 ml; containing 5 mmol $NaN_3$) and methyl tert-butyl ether (20 ml) under ice bath. The reaction system was stirred under ice bath for 10 minutes, followed by letting the reaction solution stand at room temperature (25° C.) for 5 minutes. The water phase in the reaction system was removed to obtain the organic phase which was fluorosulfonyl azide $(FSO)_2N_3$) solution with a yield of 92% (through $^{19}F$ NMR determination, relative to the number of moles of sodium azide used; in methyl tert-butyl ether (MTBE), the chemical shift of the product is +61.5 ppm, and

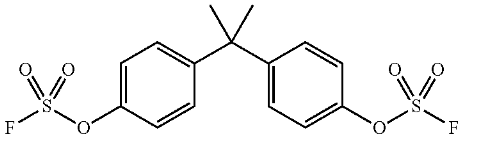 [SMILES: CC(C)(c1ccc(OS(=O)(=O)F)cc1)c1ccc(OS(=O)(=O)F)cc1]

with known quantity can be used as internal standard (δ+36.7 ppm) for quantification, and the total amount of products in the reaction system was calculated by the integral ratio of the signal of the product and the internal standard in fluorine spectrum, so as to calculate the reaction yield). GC-MS (tR): 1.69 min; EI-MS (m/z): 125 $[M]^+$ (GC-MS (EI) spectra were determined by Agilent 7890A GC system and Agilent 5975C Inert MSD system. Methods: $T_0$=40° C., 1=10 min, ramp=20° C./min; $T_1$=200° C., t=10 min). Dimethyl sulfoxide (DMSO, bout 20 ml) was added to the solution of fluorosulfonyl azide ($FSO_2N_3$), and the resulting solution can be directly used for the diazotransfer reaction of primary amine compounds (see EXAMPLE 3).

Example 2 Preparation of Primary Amine Compound Library 1128 different primary amine compounds (including alkyl primary amine, aryl primary amine and heteroaryl primary amine) were respectively prepared into a solution with a concentration of about 100 mM, the solvent was dimethyl sulfoxide, the volume was about 1 ml, and the solution was stored in a 96-well microplate with a size of 1.2 ml.

When the primary amine compound is an aryl primary amine or heteroaryl primary amine, and the compound contains n primary amine functional groups that can be converted to azide, 0.10/n mmol primary amine was dissolved in 1.0 ml of dimethyl sulfoxide in a 1.5 ml centrifuge tube, and then transferred to the wells in the corresponding locations of its corresponding microplate.

When the primary amine compound is an ammonium salt obtained by neutralizing alkyl primary amine with hydrochloric acid, methanesulfonic acid, tartaric acid, p-toluenesulfonic acid, or hydrobromic acid, and the compound contains n primary amine functional groups that can be converted to azide, 0.10/n mmol primary amine was dissolved in 1.0 ml of dimethyl sulfoxide in a 1.5 ml centrifuge tube, and then transferred to the wells in the corresponding locations of its corresponding microplate.

When the primary amine compound is a free alkyl primary amine, and the compound contains n primary amine functional groups that can be converted to azide, 0.10/n mmol primary amine was dissolved in 1.0 ml 100/n mM methanesulfonic acid solution (solvent is dimethyl sulfoxide) in a 1.5 ml centrifuge tube. If the compound contains two or more free basic functional groups (primary amine, secondary amine, tertiary amine, guanidine, etc.), increase the concentration of methanesulfonic acid solution to 200/n mM. The prepared primary amine solution was then transferred to wells at in the corresponding locations of its corresponding microplate.

Primary amines with poor solubility in dimethyl sulfoxide could also be prepared into azide compounds by diazotransfer, and most of these azide products can be dissolved in dimethyl sulfoxide and classified into azide compound library in solution form. However, these primary amines with poor solubility could not be stored in the primary amine compound library in solution form. In addition to the above mentioned 1128 primary amine compound libraries stored in solution form in microplates (distributed in 12 96-well microplates), another 96 primary amines (some of which have poor solubility) were selected as substrates for diazotransfer. Thus, a library contained 1224 primary amines with different structures was constructed, which can be used for the subsequent preparation of azide compound library (FIG. 1).

Example 3 Preparation of Azide Compound Library

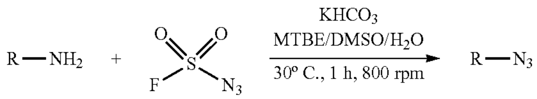

The fluorosulfonyl azide solution prepared by the method of EXAMPLE 1 (the solvent was methyl tert-butyl ether, the concentration was about 400 mM through $^{19}F$ NMR determination, about 40 ml) diluted with dimethyl sulfoxide (40 ml) to obtain a fluorosulfonyl azide solution (the concentration was about 20 C mM through $^{19}F$ NMR measurement, 80 ml, the solvent was dimethyl sulfoxide/methyl tert-butyl ether 1:1).

Using a 96-well pipette to transfer the primary amine solution (100 mM in the solvent dimethyl sulfoxide; took out 200 μl, containing 20 μmol of primary amine) in each well of a 96-well plate in the primary amine compound library prepared in Example 2 to an empty 1.2 ml 96-well microplate. Aqueous potassium bicarbonate solution (3.0 M, 26.7 μl, containing 80 μmol of potassium bicarbonate) and the above diluted fluorosulfonyl azide solution (200 mM, 100 μl, containing 20 μmol of fluorosulfonyl azide) were added to each well. Additional dimethyl sulfoxide (73 μl) was added to bring the total volume about 400 μl. The microplate was sealed and placed in a shaker, shaken for 1 hour at 800 rpm under 30° C. After shaking, a 50 mM solution of the corresponding azide compound (the solvent system was about 3:1 of dimethyl sulfoxide/methyl tert-butyl ether) was obtained with a yield close to quantitative in each well in the microplate. The reaction solution in each well in the microplate was detected by UPLC-MS. Exemplary UPLC chromatography were shown in FIGS. 2*a-f.*

From the compound library of 1128 primary amines in Example 2, 1128 corresponding azides were obtained by this method. The 1128 azide solutions were distributed in 12 96-well microplates (serial number of the microplates were 1-7 and 10-14). The 96 separately stored primary amines mentioned in EXAMPLE 2 (some of which have poor solubility) were reacted by the same method in this example to yield 96 soluble azide solutions and transferred to a new 96-well microplate (see plate 8 of azide library for details). Thereby, a compound library containing 1224 azide solutions with different structures was constructed.

The compound library containing 1224 azide solutions with different structures were distributed in 13 96-well microplates. The microplate of the azide compound library could be sealed and stored in a refrigerator at a refrigeration temperature (4° C.), stable for at least 6 months. The compound library could be directly used for reaction without separation.

The structures in azide compound library and their locations in the microplates were as follows, and the corresponding locations of primary amine library (except the eighth plate) and triazole library remained unchanged.

Example 4 Copper-Catalyzed Cycloaddition of Azide Terminated Alkynes (CuAAC) Using an Azide Library

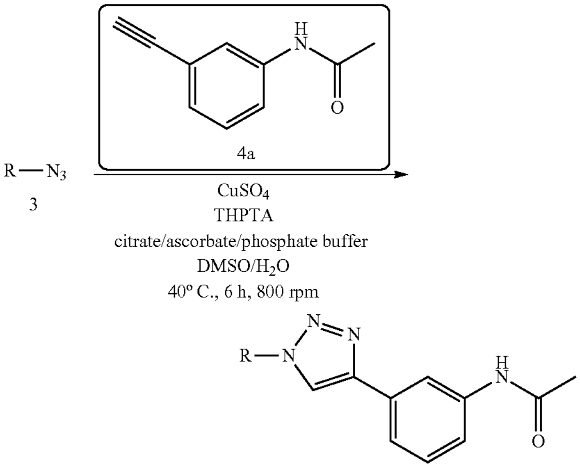

5a

-continued

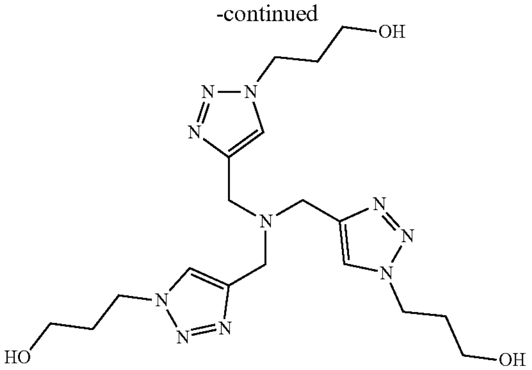

THPTA

Sodium ascorbate (2.48 g, 12.5 mmol), disodium hydrogen phosphate (7.0 g, 49.3 mmol) and citric acid (4.87 g, 25.4 mmol) were mixed and dissolved in distilled water to 100 ml aqueous solution to obtain a sodium buffer solution of ascorbate/disodium hydrogen phosphate/citric acid with a pH value of about 5.

From the eighth plate of the azide library obtained in EXAMPLE 2, the solution (100 μl, the concentration of about 50 mM, containing about 5 μl mol of azide) was taken from each well and transferred to a new 96-well plate with a size of 350 μl. The above buffer solution of ascorbic acid/disodium hydrogen phosphate/citric acid (40 g 1) was successively added to each well, and after sealing film, shaken at 800 rpm for 15 minutes at 30° C. Tearing off the sealing film, 3-acetamidophenylacetylene solution (compound 4a, 100 mM, the solvent was dimethyl sulfoxide; 47.5 μl, containing 4.75 μmol of 3-acetaminophenylacetylene) and copper sulfate/THPTA aqueous solution (the concentrations of both copper sulfate and THPTA were 20 mM respectively, 12.5 g 1, 0.25 μmol) were added to each well. The microplate was sealed and shaken for 6 hour at 800 rpm under 40° C. After the reaction was completed, the in-plate mixture was transferred one-to-one to an empty 1.2 ml 96-well plate, diluted by adding methanol (400 μl) and acetonitrile (400 μl) to each well, and the resulting 1, 2, 3-triazole products were detected by UPLC-MS.

Exemplary UPLC chromatograms of 1, 2, 3-triazole products were shown in FIGS. 3*a-f.*

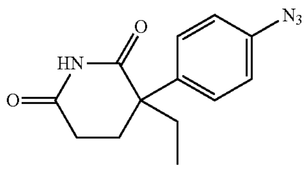 [SMILES: CCC1(c2ccc(N=[N+]=[N-])cc2)CCC(=O)NC1=O]

Plate 1 A1

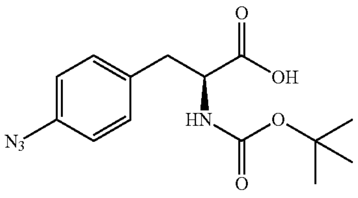

Plate 1 A2

-continued
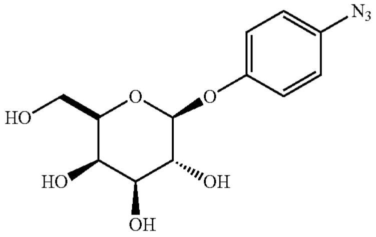 [SMILES: [N-]=[N+]=Nc1ccc(O[C@@H]2O[C@H](CO)[C@H](O)[C@H](O)[C@H]2O)cc1]
Plate 1 A3
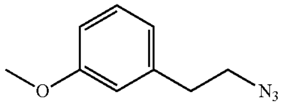
Plate 1 A4
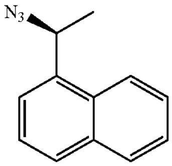
Plate 1 B1
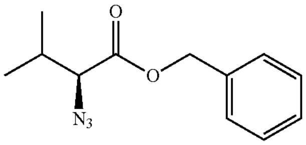
Plate 1 B2
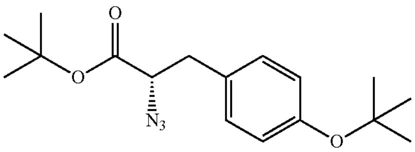
Plate 1 B3
Plate 1 B3
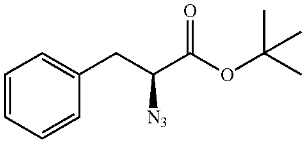
Plate 1 B4
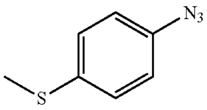
Plate 1 C1
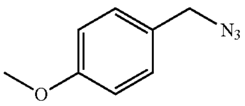
Plate 1 C2
-continued
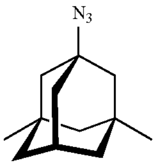
Plate 1 C3
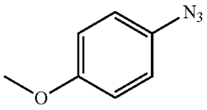
Plate 1 C4
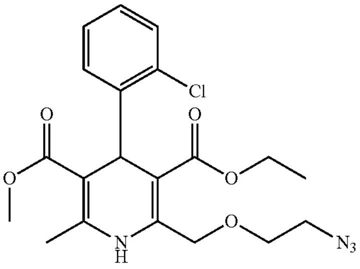 [SMILES: CCOC(=O)C1=C(COCCN=[N+]=[N-])NC(C)=C(C(=O)OC)C1c1ccccc1Cl]
Plate 1 D1
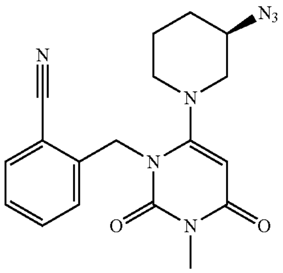 [SMILES: Cn1c(=O)cc(N2CCC[C@@H](N=[N+]=[N-])C2)n(Cc2ccccc2C#N)c1=O]
Plate 1 D2
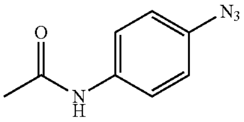
Plate 1 D3
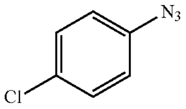
Plate 1 D4
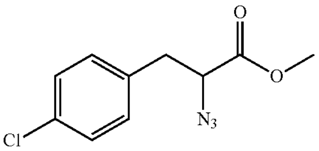 [SMILES: COC(=O)C(Cc1ccc(Cl)cc1)N=[N+]=[N-]]
Plate 1 E1

-continued
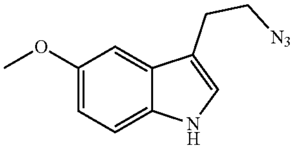 [SMILES: COc1ccc2[nH]cc(CCN=[N+]=[N-])c2c1]
Plate 1 E2
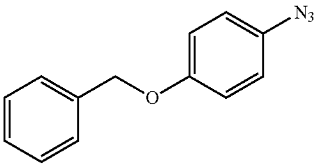 [SMILES: [N-]=[N+]=Nc1ccc(OCc2ccccc2)cc1]
Plate 1 E3
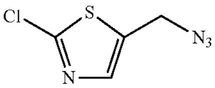
Plate 1 E4
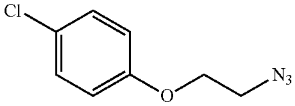 [SMILES: [N-]=[N+]=NCCOc1ccc(Cl)cc1]
Plate 1 F1
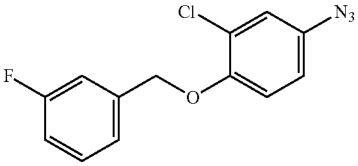 [SMILES: [N-]=[N+]=Nc1ccc(OCc2cccc(F)c2)c(Cl)c1]
Plate 1 F2
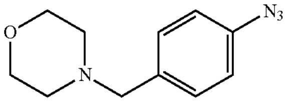 [SMILES: [N-]=[N+]=Nc1ccc(CN2CCOCC2)cc1]
Plate 1 F3
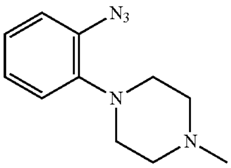 [SMILES: CN1CCN(c2ccccc2N=[N+]=[N-])CC1]
Plate 1 F4
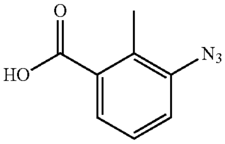
Plate 1 G1
-continued
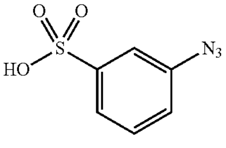 [SMILES: [N-]=[N+]=Nc1cccc(S(=O)(=O)O)c1]
Plate 1 G2
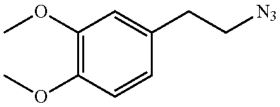
Plate 1 G3
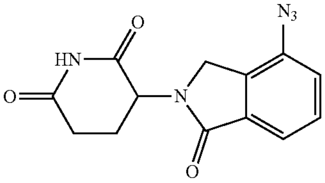 [SMILES: [N-]=[N+]=Nc1cccc2c1CN(C1CCC(=O)NC1=O)C2=O]
Plate 1 G4
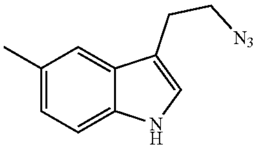
Plate 1 H1
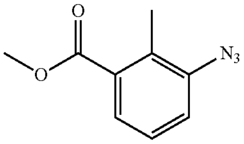
Plate 1 H2
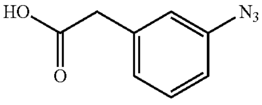 [SMILES: [N-]=[N+]=Nc1cccc(CC(=O)O)c1]
Plate 1 H3
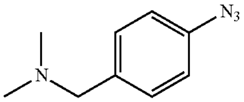
Plate 1 H4
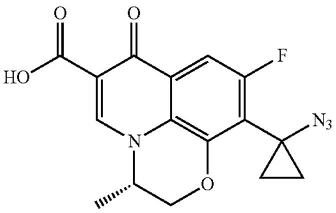 [SMILES: C[C@H]1COc2c(C3(N=[N+]=[N-])CC3)c(F)cc3c(=O)c(C(=O)O)cn1c23]
Plate 1 A5

-continued
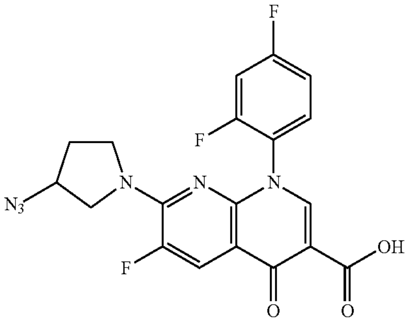 [SMILES: [N-]=[N+]=NC1CCN(c2nc3c(cc2F)c(=O)c(C(=O)O)cn3-c2ccc(F)cc2F)C1]
Plate 1 A6
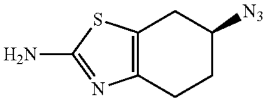 [SMILES: [N-]=[N+]=N[C@H]1CCc2nc(N)sc2C1]
Plate 1 A7
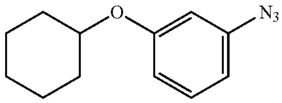 [SMILES: [N-]=[N+]=Nc1cccc(OC2CCCCC2)c1]
Plate 1 A8
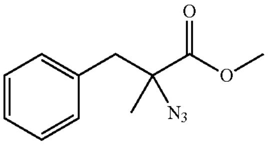
Plate 1 B5
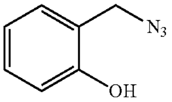
Plate 1 B6
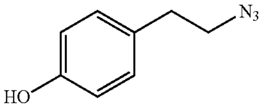
Plate 1 B7
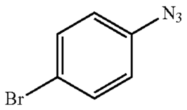
Plate 1 B8
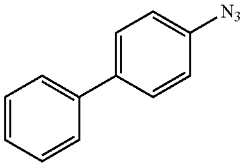 [SMILES: [N-]=[N+]=Nc1ccc(-c2ccccc2)cc1]
Plate 1 C5
-continued
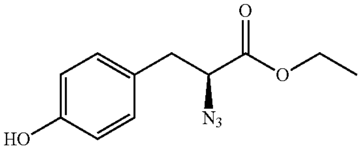 [SMILES: CCOC(=O)[C@H](Cc1ccc(O)cc1)N=[N+]=[N-]]
Plate 1 C6
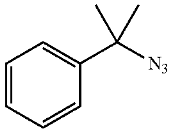
Plate 1 C7
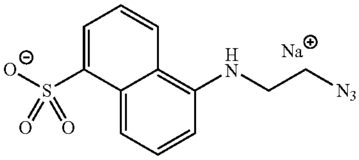 [SMILES: [N-]=[N+]=NCCNc1cccc2c(S(=O)(=O)[O-])cccc12 ; [Na+]]
Plate 1 C8
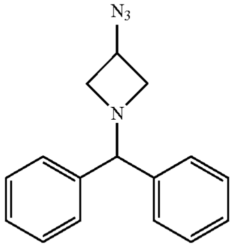 [SMILES: [N-]=[N+]=NC1CN(C(c2ccccc2)c2ccccc2)C1]
Plate 1 D5
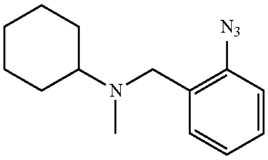 [SMILES: CN(Cc1ccccc1N=[N+]=[N-])C1CCCCC1]
Plate 1 D6
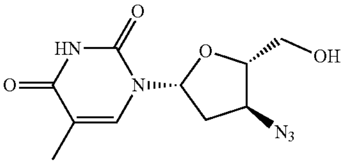 [SMILES: Cc1cn([C@H]2C[C@H](N=[N+]=[N-])[C@@H](CO)O2)c(=O)[nH]c1=O]
Plate 1 D7
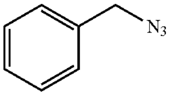
Plate 1 D8
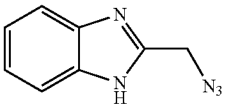
Plate 1 E5

-continued
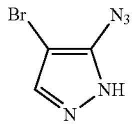
Plate 1 E6
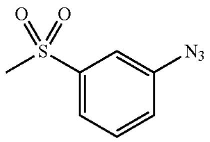
Plate 1 E7
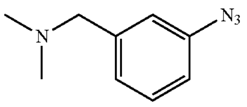
Plate 1 E8
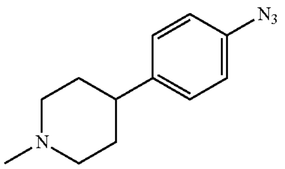 [SMILES: CN1CCC(c2ccc(N=[N+]=[N-])cc2)CC1]
Plate 1 F5
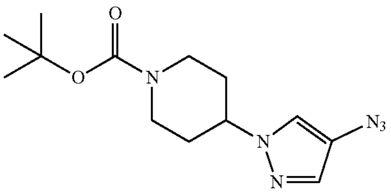 [SMILES: CC(C)(C)OC(=O)N1CCC(n2cc(N=[N+]=[N-])cn2)CC1]
Plate 1 F6
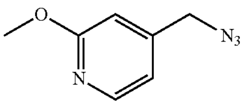
Plate 1 F7
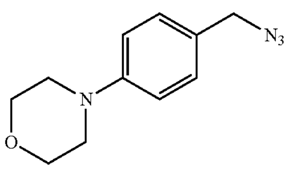 [SMILES: [N-]=[N+]=NCc1ccc(N2CCOCC2)cc1]
Plate 1 F8
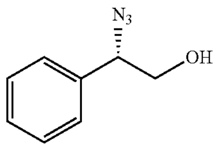 [SMILES: [N-]=[N+]=N[C@H](CO)c1ccccc1]
Plate 1 G5
-continued
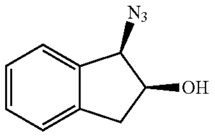 [SMILES: [N-]=[N+]=N[C@@H]1c2ccccc2C[C@@H]1O]
Plate 1 G6
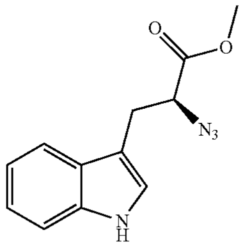 [SMILES: COC(=O)[C@H](Cc1c[nH]c2ccccc12)N=[N+]=[N-]]
Plate 1 G7
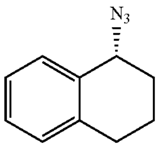 [SMILES: [N-]=[N+]=N[C@@H]1CCCc2ccccc21]
Plate 1 G8
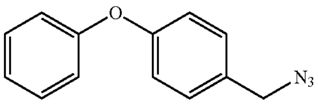 [SMILES: [N-]=[N+]=NCc1ccc(Oc2ccccc2)cc1]
Plate 1 H5
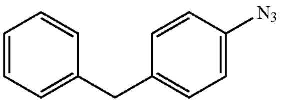 [SMILES: [N-]=[N+]=Nc1ccc(Cc2ccccc2)cc1]
Plate 1 H6
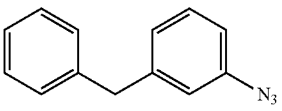
Plate 1 H7
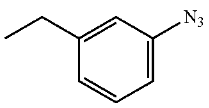
Plate 1 H8
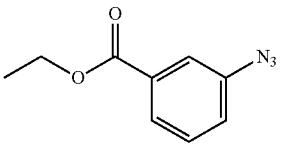
Plate 1 A9

-continued
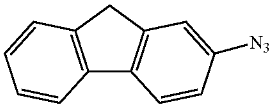
Plate 1 A10
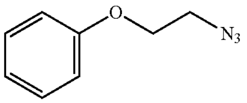
Plate 1 A11
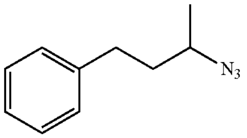
Plate 1 A12
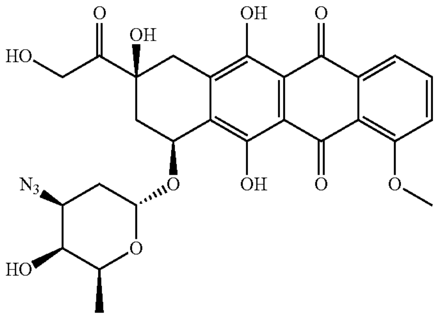
Plate 1 B9
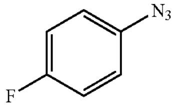
Plate 1 B10
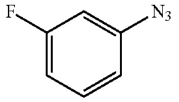
Plate 1 B11
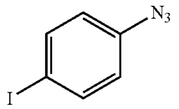
Plate 1 B12
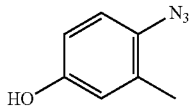
Plate 1 C9
-continued
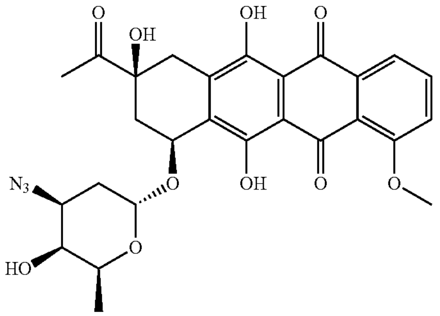 [SMILES: COc1cccc2c1C(=O)c1c(O)c3c(c(O)c1C2=O)C[C@@](O)(C(C)=O)C[C@@H]3O[C@H]1C[C@H](N=[N+]=[N-])[C@H](O)[C@H](C)O1]
Plate 1 C10
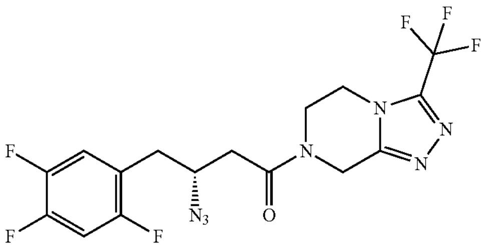 [SMILES: [N-]=[N+]=N[C@@H](CC(=O)N1CCn2c(nnc2C(F)(F)F)C1)Cc1cc(F)c(F)cc1F]
Plate 1 C11
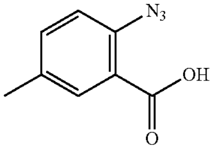
Plate 1 C12
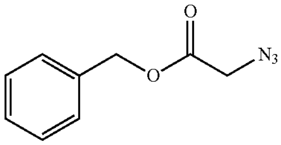 [SMILES: [N-]=[N+]=NCC(=O)OCc1ccccc1]
Plate 1 D9
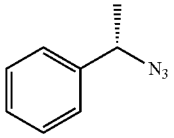
Plate 1 D10
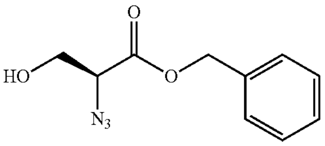 [SMILES: [N-]=[N+]=N[C@@H](CO)C(=O)OCc1ccccc1]
Plate 1 D11

-continued
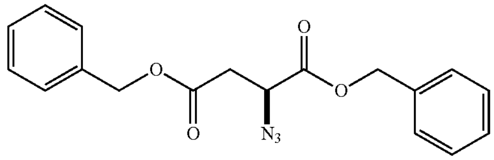 [SMILES: [N-]=[N+]=N[C@@H](CC(=O)OCc1ccccc1)C(=O)OCc1ccccc1]
Plate 1 D12
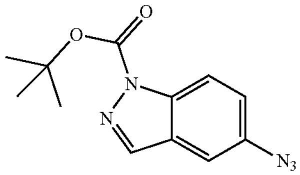 [SMILES: CC(C)(C)OC(=O)n1ncc2cc(N=[N+]=[N-])ccc21]
Plate 1 E9
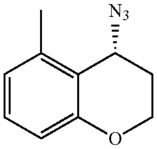
Plate 1 E10
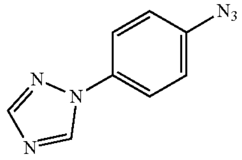 [SMILES: [N-]=[N+]=Nc1ccc(-n2cncn2)cc1]
Plate 1 E11
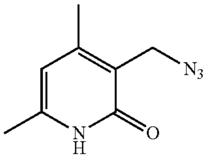
Plate 1 E12
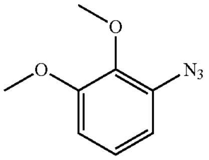
Plate 1 F9
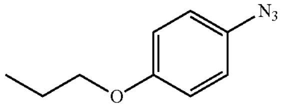
Plate 1 F10
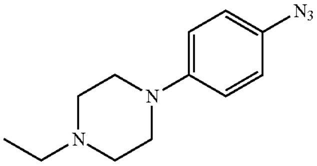 [SMILES: CCN1CCN(c2ccc(N=[N+]=[N-])cc2)CC1]
Plate 1 F11
-continued
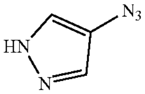
Plate 1 F12
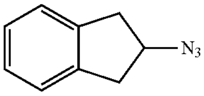 [SMILES: [N-]=[N+]=NC1Cc2ccccc2C1]
Plate 1 G9
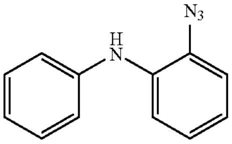 [SMILES: [N-]=[N+]=Nc1ccccc1Nc1ccccc1]
Plate 1 G10
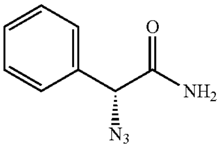
Plate 1 G11
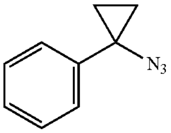 [SMILES: [N-]=[N+]=NC1(c2ccccc2)CC1]
Plate 1 G12
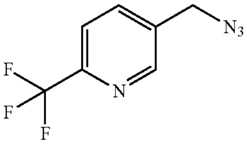 [SMILES: [N-]=[N+]=NCc1ccc(C(F)(F)F)nc1]
Plate 1 H9
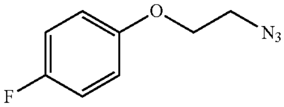 [SMILES: [N-]=[N+]=NCCOc1ccc(F)cc1]
Plate 1 H10
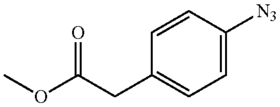
Plate 1 H11
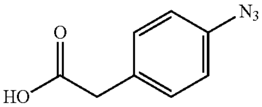 [SMILES: [N-]=[N+]=Nc1ccc(CC(=O)O)cc1]
Plate 1 H12

Plate 2
| | 1 | 2 | 3 | 4 |
|---|---|---|---|---|
| A | 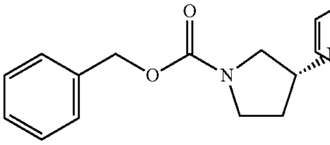 A1 | 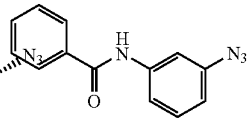 A2 | 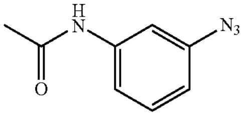 A3 | 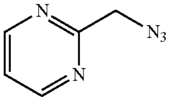 A4 |
| B | 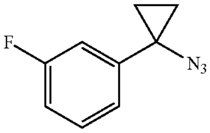 B1 | 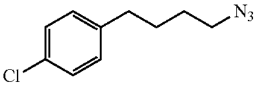 B2 | 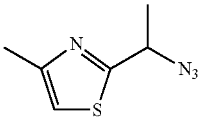 B3 | 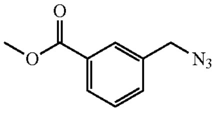 B4 |
| C | 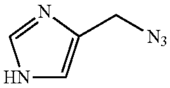 C1 | 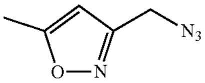 C2 | 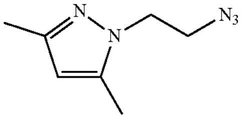 C3 | 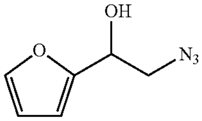 C4 |
| D | 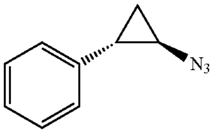 D1 | 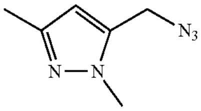 D2 | 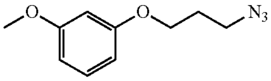 D3 | 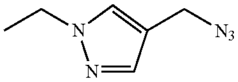 D4 |
| E | 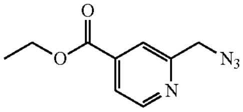 E1 | 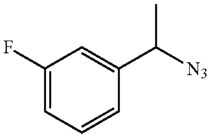 E2 | 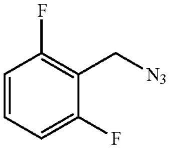 E3 | 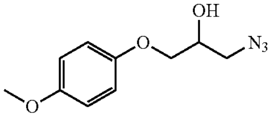 E4 |
| F | 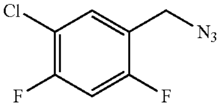 F1 | 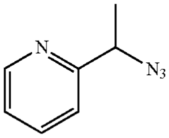 F2 | 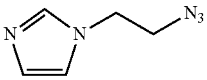 F3 | 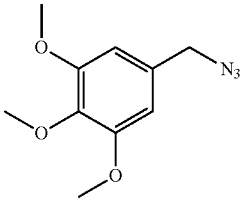 F4 |
| G | 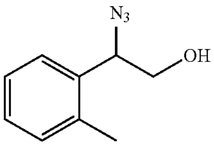 G1 | 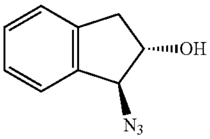 G2 | 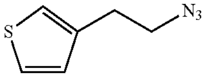 G3 | 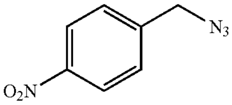 G4 |
| H | 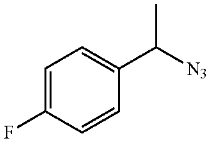 H1 | 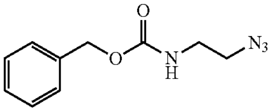 H2 | 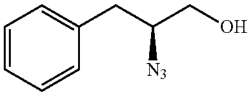 H3 | 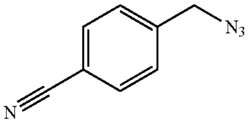 H4 |

-continued
Plate 2
| | 5 | 6 | 7 | 8 |
|---|---|---|---|---|
| A | 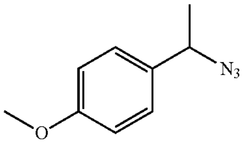 A5 | 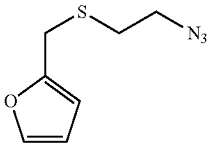 A6 | 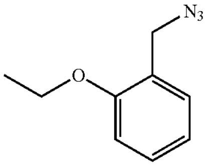 A7 | 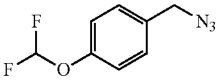 A8 |
| B | 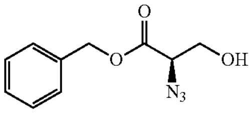 B5 | 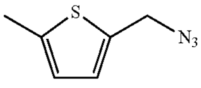 B6 | 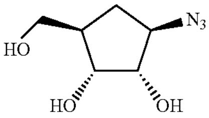 B7 | 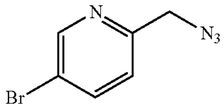 B8 |
| C | 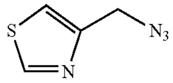 C5 | 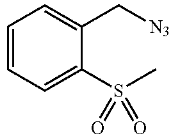 C6 | 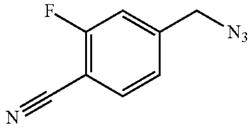 C7 | 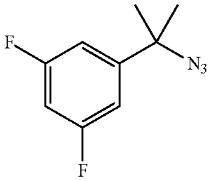 C8 |
| D | 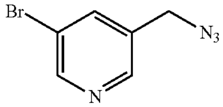 D5 | 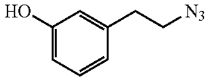 D6 | 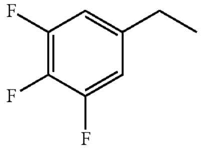 D7 | 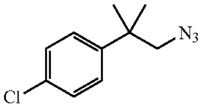 D8 |
| E | 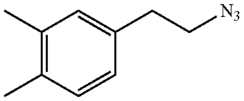 E5 | 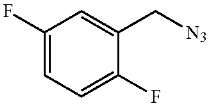 E6 | 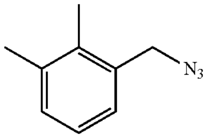 E7 | 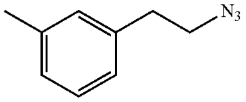 E8 |
| F | 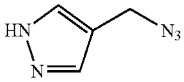 F5 | 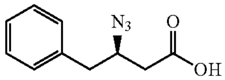 F6 | 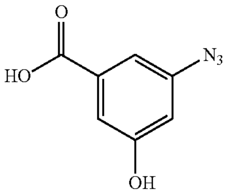 F7 | 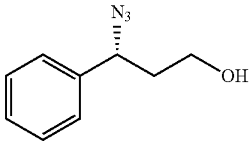 F8 |
| G | 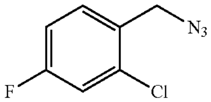 G5 | 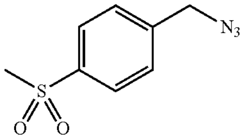 G6 | 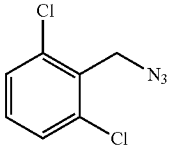 G7 | 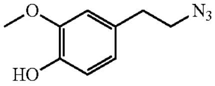 G8 |
| H | 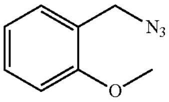 H5 | 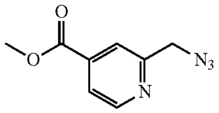 H6 | 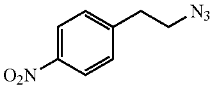 H7 | 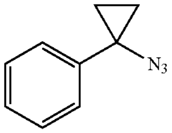 H8 |

-continued
| Plate 2 | | | | |
|---|---|---|---|---|
| | 9 | 10 | 11 | 12 |
| A | 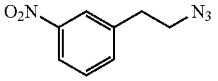 A9 | 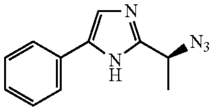 A10 | 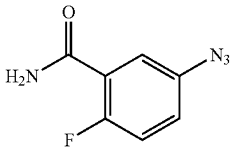 A11 | 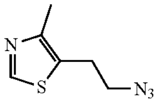 A12 |
| B | 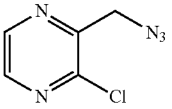 B9 | 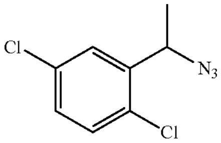 B10 | 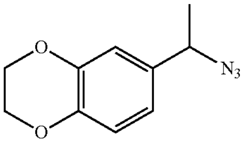 B11 | 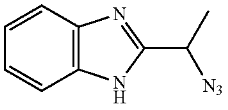 B12 |
| C | 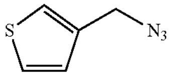 C9 | 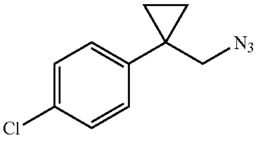 C10 | 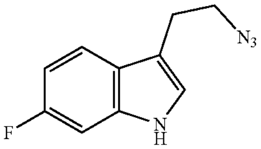 C11 | 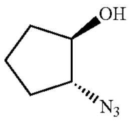 C12 |
| D | 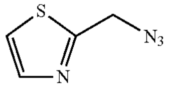 D9 | 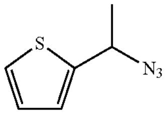 D10 | 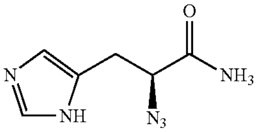 D11 | 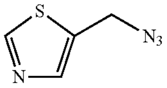 D12 |
| E | 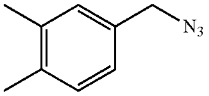 E9 | 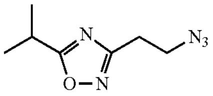 E10 | 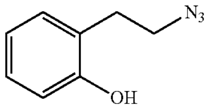 E11 | 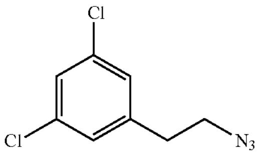 E12 |
| F | 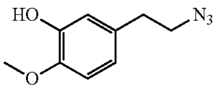 F9 | 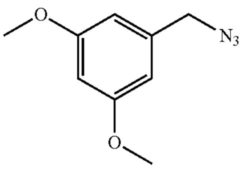 F10 | 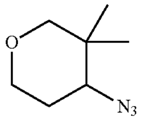 F11 | 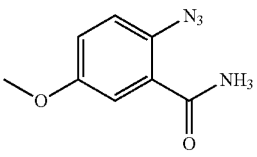 F12 |
| G | 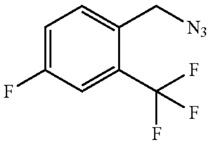 G9 | 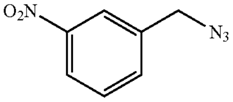 G10 | 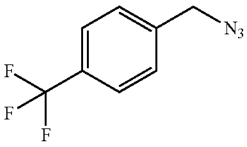 G11 | 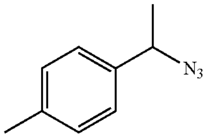 G12 |
| H | 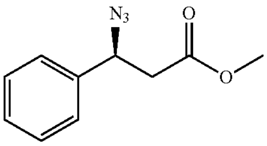 H9 | 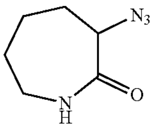 H10 | 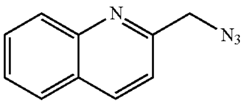 H11 | 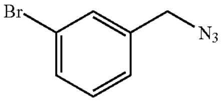 H12 |

Plate 3
| | 1 | 2 | 3 | 4 |
|---|---|---|---|---|
| A | 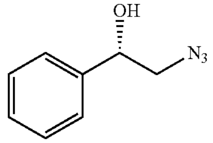 A1 | 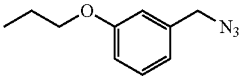 A2 | 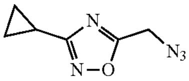 A3 | 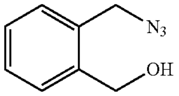 A4 |
| B | 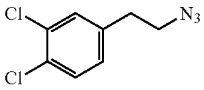 B1 | 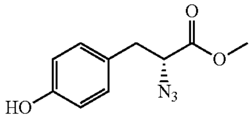 B2 | 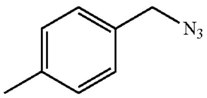 B3 | 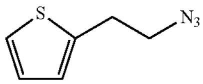 B4 |
| C | 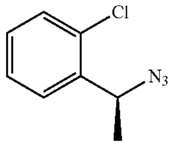 C1 | 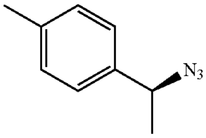 C2 | 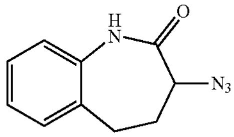 C3 | 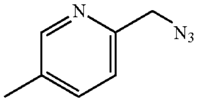 C4 |
| D | 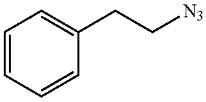 D1 | 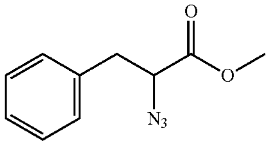 D2 | 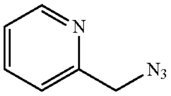 D3 | 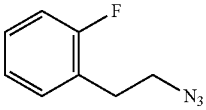 D4 |
| E | 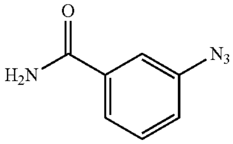 E1 | 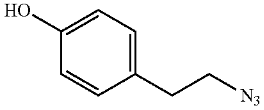 E2 | 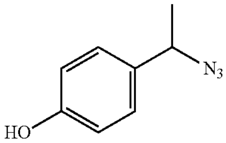 E3 | 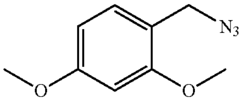 E4 |
| F | 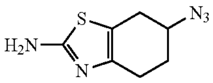 F1 | 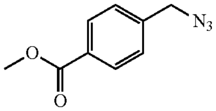 F2 | 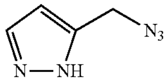 F3 | 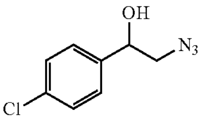 F4 |
| G | 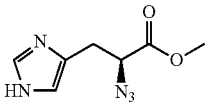 G1 | 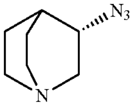 G2 | 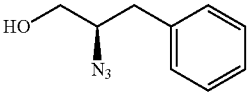 G3 | 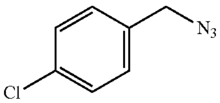 G4 |
| H | 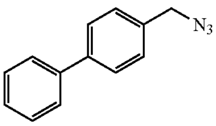 H1 | 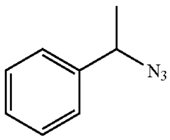 H2 | 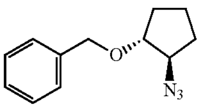 H3 | 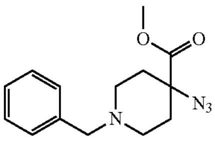 H4 |

-continued
| Plate 3 | | | | |
|---|---|---|---|---|
| | 5 | 6 | 7 | 8 |
| A | 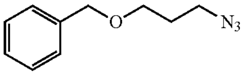 A5 | 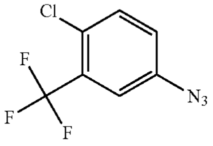 A6 | 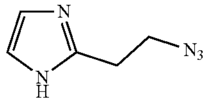 A7 | 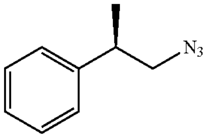 A8 |
| B | 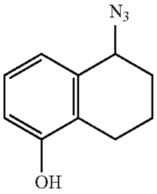 B5 | 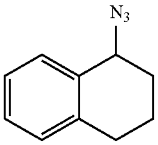 B6 | 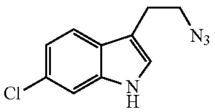 B7 | 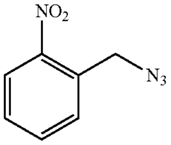 B8 |
| C | 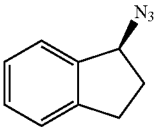 C5 | 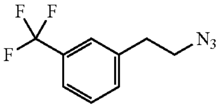 C6 | 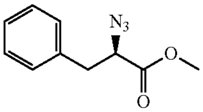 C7 | 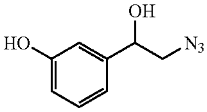 C8 |
| D | 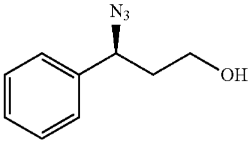 D5 | 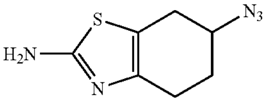 D6 | 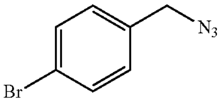 D7 | 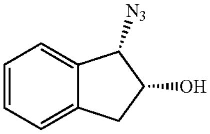 D8 |
| E | 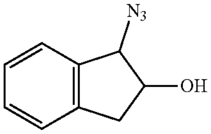 E5 | 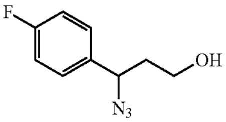 E6 | 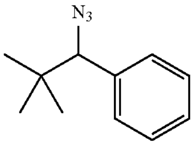 E7 | 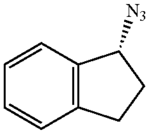 E8 |
| F | 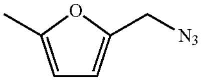 F5 | 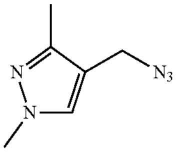 F6 | 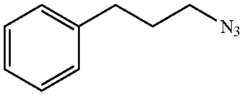 F7 | 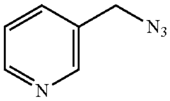 F8 |
| G | 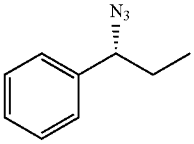 G5 | 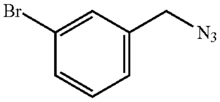 G6 | 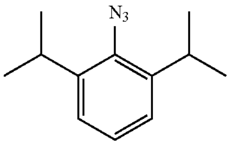 G7 | 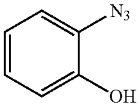 G8 |
| H | 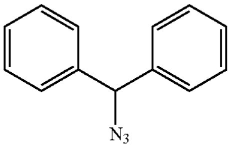 H5 | 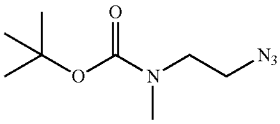 H6 | 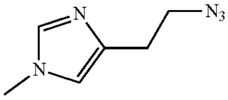 H7 | 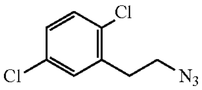 H8 |

-continued
| Plate 3 | | | | |
|---|---|---|---|---|
| | 9 | 10 | 11 | 12 |
| A | 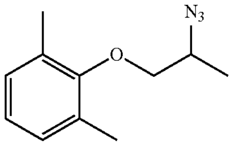 A9 | 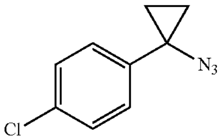 A10 | 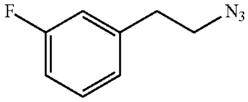 A11 | 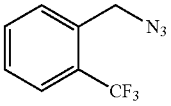 A12 |
| B | 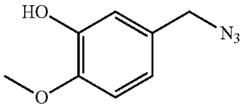 B9 | 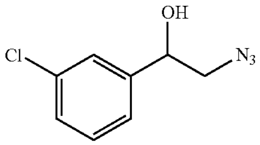 B10 | 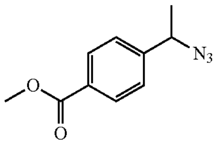 B11 | 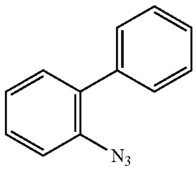 B12 |
| C | 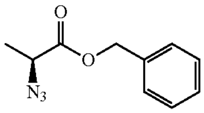 C9 | 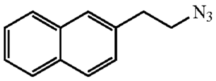 C10 | 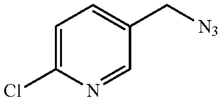 C11 | 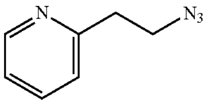 C12 |
| D | 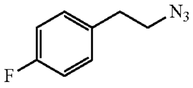 D9 | 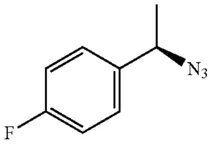 D10 | 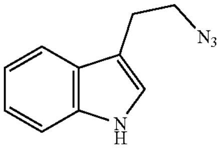 D11 | 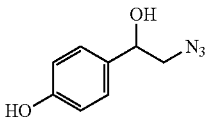 D12 |
| E | 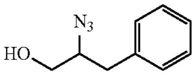 E9 | 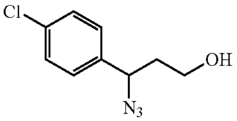 E10 | 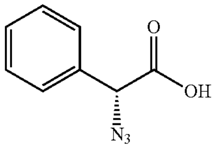 E11 | 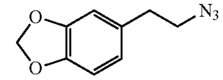 E12 |
| F | 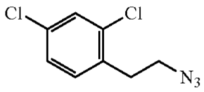 F9 | 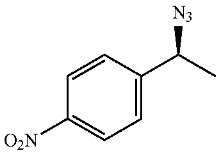 F10 | 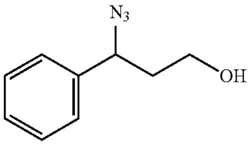 F11 | 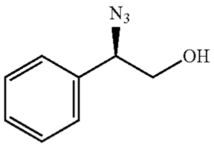 F12 |
| G | 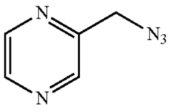 G9 | 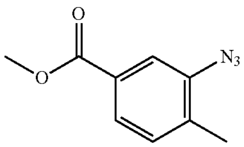 G10 | 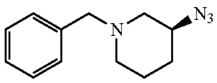 G11 | 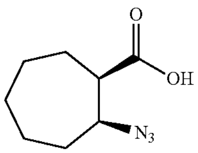 G12 |
| H | 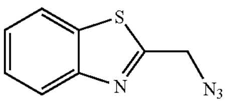 H9 | 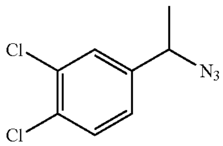 H10 | 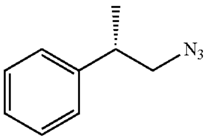 H11 | 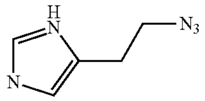 H12 |

Plate 4
| | 1 | 2 | 3 | 4 |
|---|---|---|---|---|
| A | 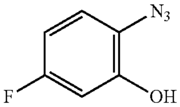 A1 | 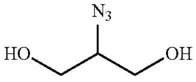 A2 | 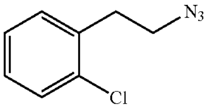 A3 | 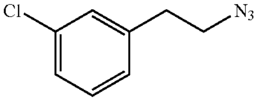 A4 |
| B | 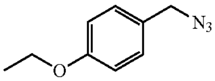 B1 | 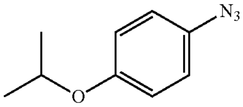 B2 | 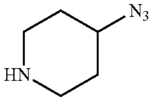 B3 | 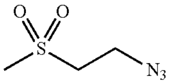 B4 |
| C | 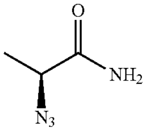 C1 | 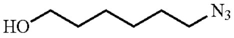 C2 | 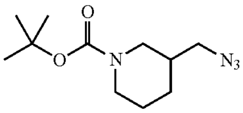 C3 | 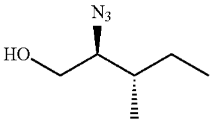 C4 |
| D | 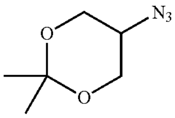 D1 | 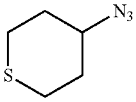 D2 | 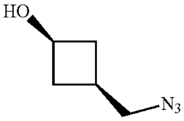 D3 | 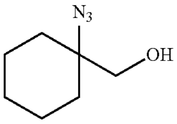 D4 |
| E | 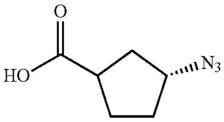 E1 | 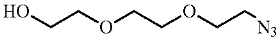 E2 | 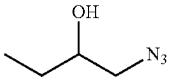 E3 | 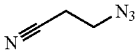 E4 |
| F | 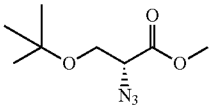 F1 | 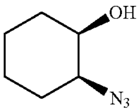 F2 | 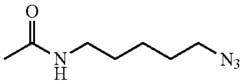 F3 | 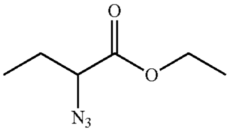 F4 |
| G | 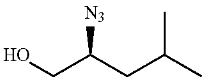 G1 | 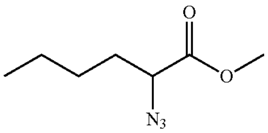 G2 | 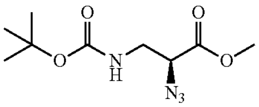 G3 | 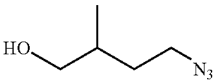 G4 |
| H | 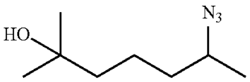 H1 | 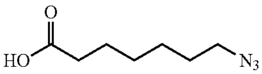 H2 | 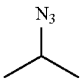 H3 | 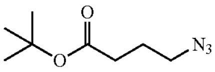 H4 |
| | 5 | 6 | 7 | 8 |
| A | 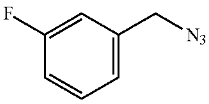 A5 | 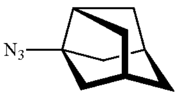 A6 | 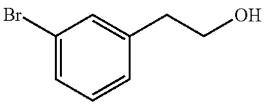 A7 | 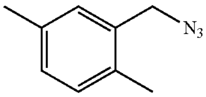 A8 |

-continued
| | | | | |
|---|---|---|---|---|
| | Plate 4 | | | |
| B | 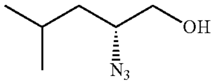 B5 | 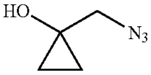 B6 | 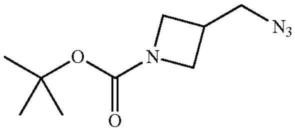 B7 | 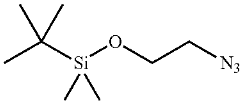 B8 |
| C | 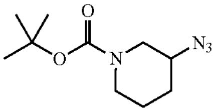 C5 | 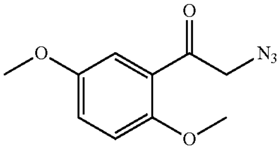 C6 | 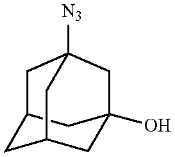 C7 | 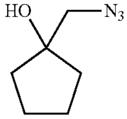 C8 |
| D | 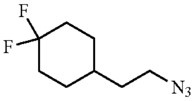 D5 | 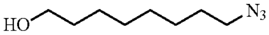 D6 | 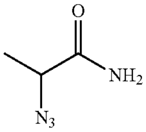 D7 | 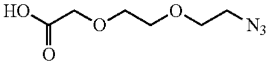 D8 |
| E | 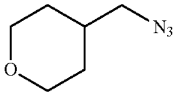 E5 | 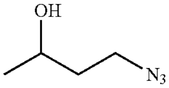 E6 | 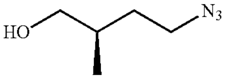 E7 | 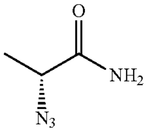 E8 |
| F | 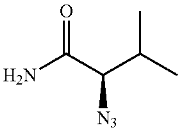 F5 | 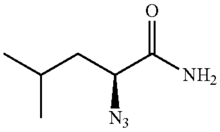 F6 | 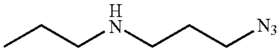 F7 | 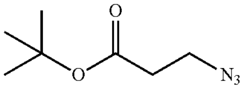 F8 |
| G | 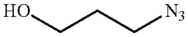 G5 | 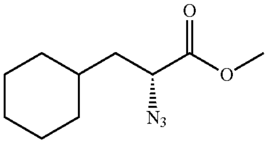 G6 | 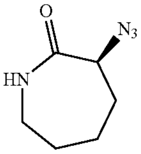 G7 | 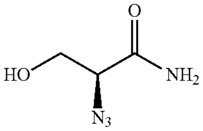 G8 |
| H | 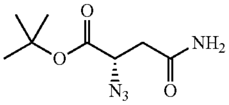 H5 | 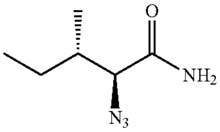 H6 | 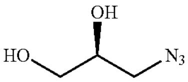 H7 | 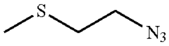 H8 |
| | 9 | 10 | 11 | 12 |
| A | 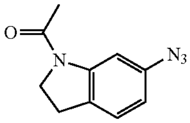 A9 | 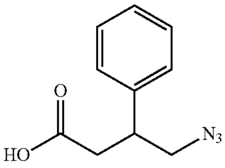 A10 | 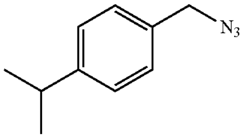 A11 | 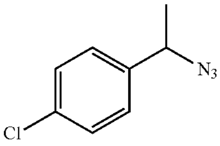 A12 |

-continued
| Plate 4 | | | | |
| --- | --- | --- | --- | --- |
| B | 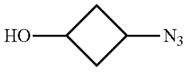 B9 | 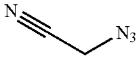 B10 | 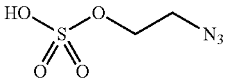 B11 | 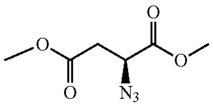 B12 |
| C | 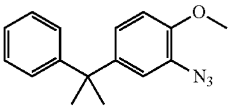 C9 | 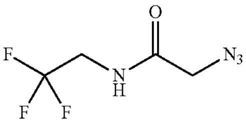 C10 | 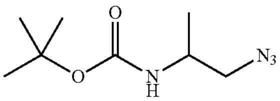 C11 | 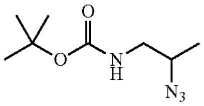 C12 |
| D | 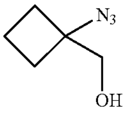 D9 | 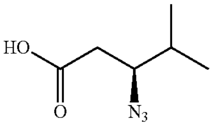 D10 | 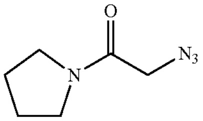 D11 | 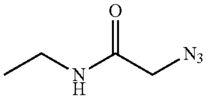 D12 |
| E | 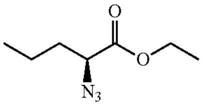 E9 | 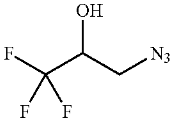 E10 | 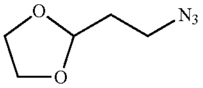 E11 | 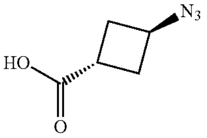 E12 |
| F | 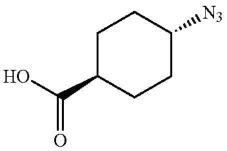 F9 | 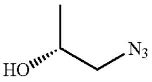 F10 | 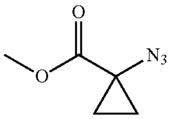 F11 | 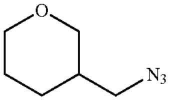 F12 |
| G | 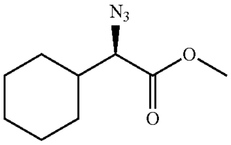 G9 | 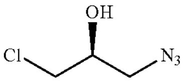 G10 | 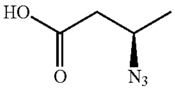 G11 | 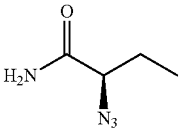 G12 |
| H | 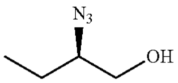 H9 | 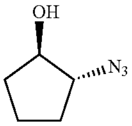 H10 | 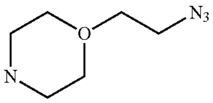 H11 | 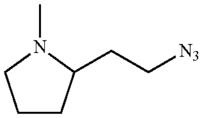 H12 |
| Plate 5 | | | | |
| --- | --- | --- | --- | --- |
| | 1 | 2 | 3 | 4 |
| A | 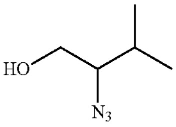 A1 | 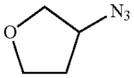 A2 | 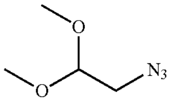 A3 | 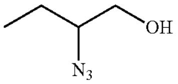 A4 |

-continued
| | Plate 5 | | | |
|---|---|---|---|---|
| B | 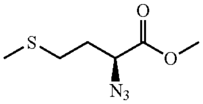 B1 | 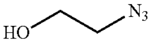 B2 | 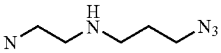 B3 | 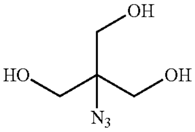 B4 |
| C | 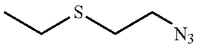 C1 | 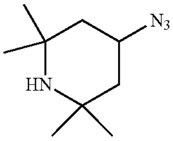 C2 | 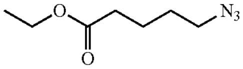 C3 | 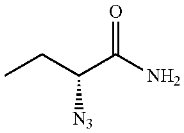 C4 |
| D | 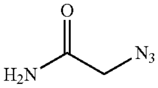 D1 | 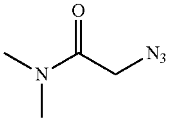 D2 | 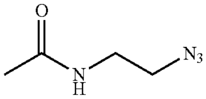 D3 | 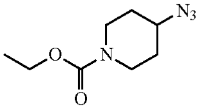 D4 |
| E | 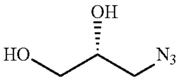 E1 | 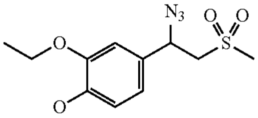 E2 | 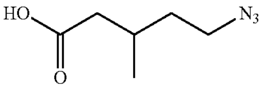 E3 | 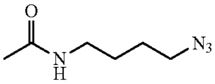 E4 |
| F | 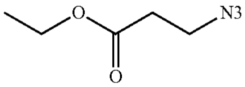 F1 | 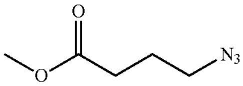 F2 | 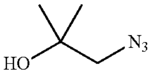 F3 | 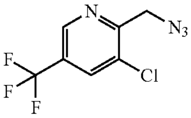 F4 |
| G | 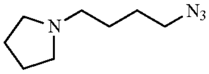 G1 | 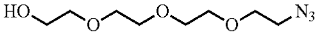 G2 | 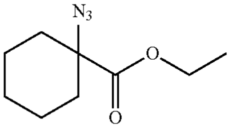 G3 | 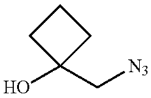 G4 |
| H | 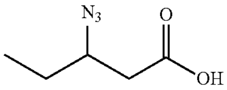 H1 | 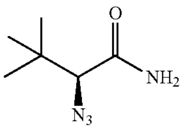 H2 | 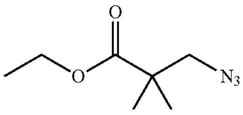 H3 | 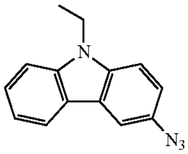 H4 |
| | 5 | 6 | 7 | 8 |
| A | 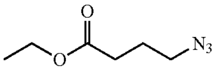 A5 | 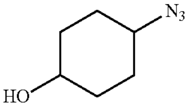 A6 | 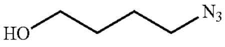 A7 | 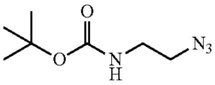 A8 |
| B | 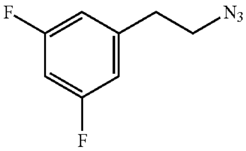 B5 | 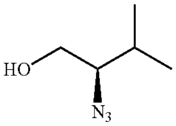 B6 | 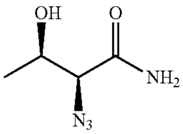 B7 | 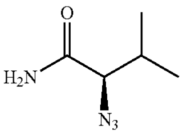 B8 |

-continued
| Plate 5 | | | | |
|---|---|---|---|---|
| C | 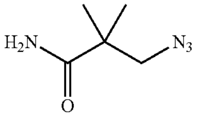 C5 | 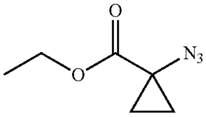 C6 | 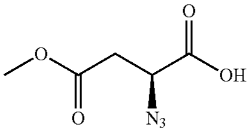 C7 | 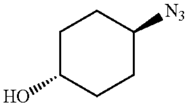 C8 |
| D | 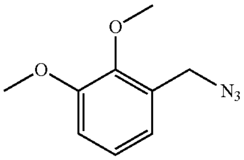 D5 | 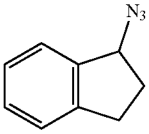 D6 | 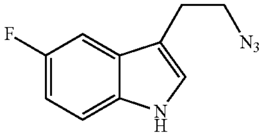 D7 | 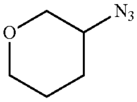 D8 |
| E | 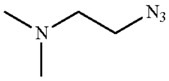 E5 | 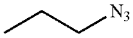 E6 | 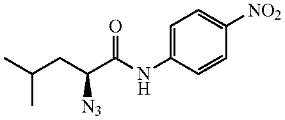 E7 | 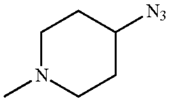 E8 |
| F | 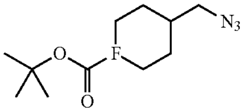 F5 | 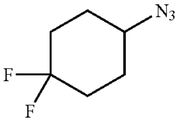 F6 | 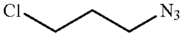 F7 | 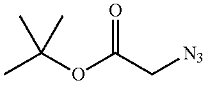 F8 |
| G | 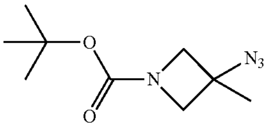 G5 | 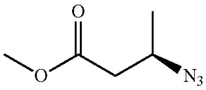 G6 | 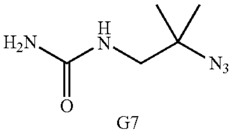 G7 | 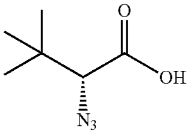 G8 |
| H | 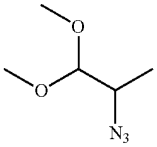 H5 | 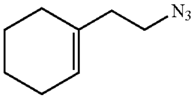 H6 | 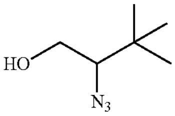 H7 | 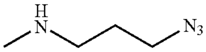 H8 |
| | 9 | 10 | 11 | 12 |
|---|---|---|---|---|
| A | 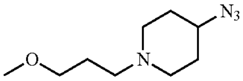 A9 | 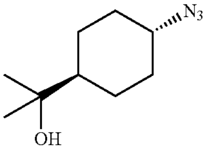 A10 | 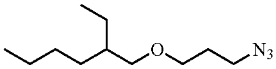 A11 | 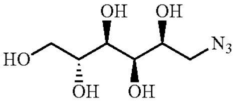 A12 |
| B | 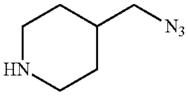 B9 | 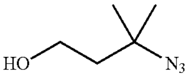 B10 | 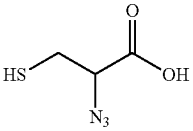 B11 | 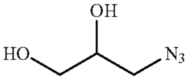 B12 |

-continued
| Plate 5 | | | | |
|---|---|---|---|---|
| C | 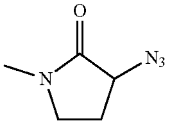 C9 | 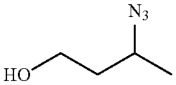 C10 | 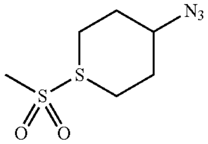 C11 | 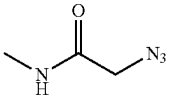 C12 |
| D | 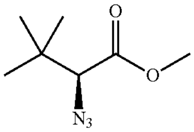 D9 | 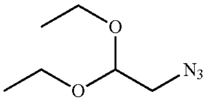 D10 | 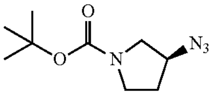 D11 | 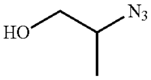 D12 |
| E | 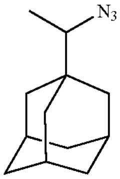 E9 | 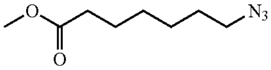 E10 | 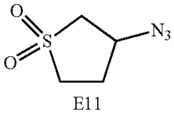 E11 | 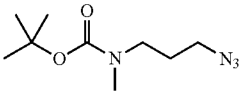 E12 |
| F | 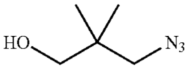 F9 | 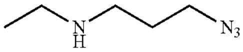 F10 | 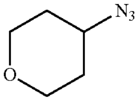 F11 | 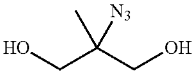 F12 |
| G | 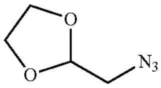 G9 | 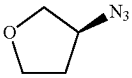 G10 | 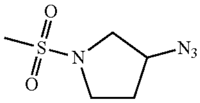 G11 | 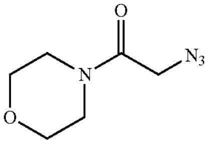 G12 |
| H | 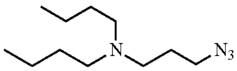 H9 | 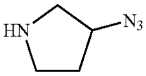 H10 | 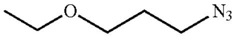 H11 | 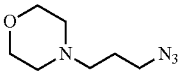 H12 |
Plate 6
| | 1 | 2 | 3 | 4 |
|---|---|---|---|---|
| A | 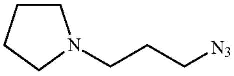 A1 | 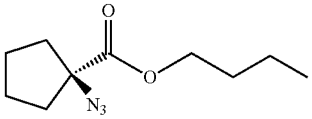 A2 | 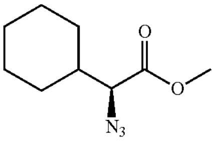 A3 | 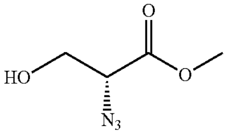 A4 |
| B | 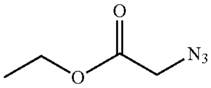 B1 | 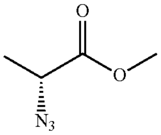 B2 | 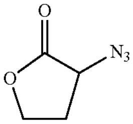 B3 | 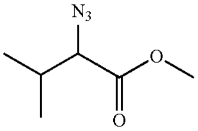 B4 |

-continued
| | Plate 6 | | | |
|---|---|---|---|---|
| C | 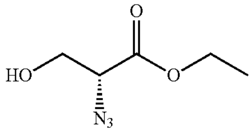 C1 | 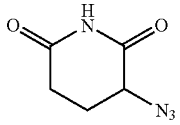 C2 | 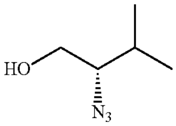 C3 | 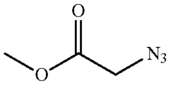 C4 |
| D | 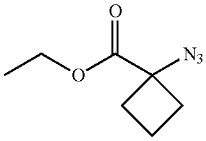 D1 | 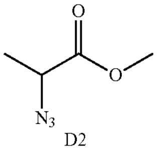 D2 | 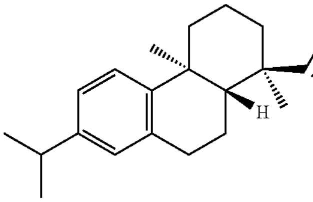 D3 | 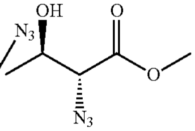 D4 |
| E | 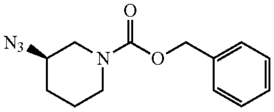 E1 | 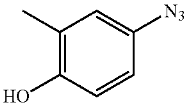 E2 | 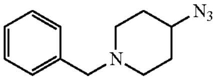 E3 | 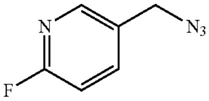 E4 |
| F | 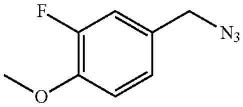 F1 | 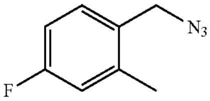 F2 | 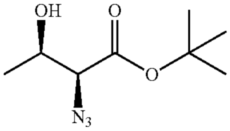 F3 | 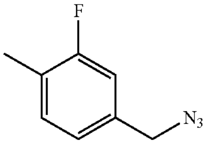 F4 |
| G | 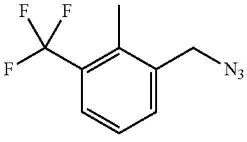 G1 | 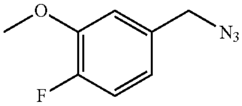 G2 | 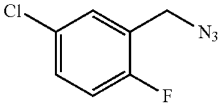 G3 | 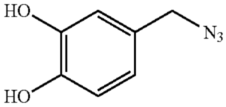 G4 |
| H | 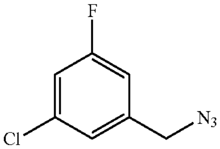 H1 | 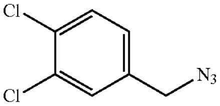 H2 | 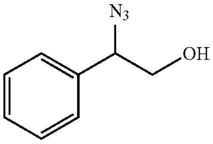 H3 | 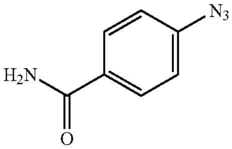 H4 |
| | 5 | 6 | 7 | 8 |
| A | 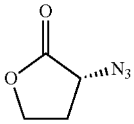 A5 | 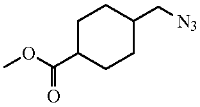 A6 | 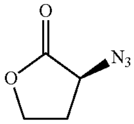 A7 | 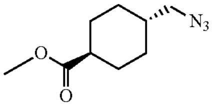 A8 |
| B | 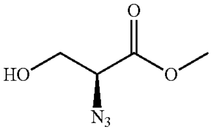 B5 | 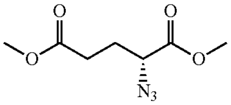 B6 | 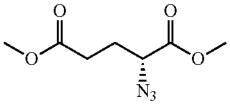 B7 | 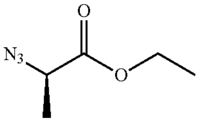 B8 |

-continued
Plate 6
| | | | | |
|---|---|---|---|---|
| C | 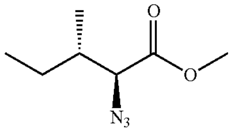 C5 | 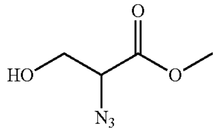 C6 | 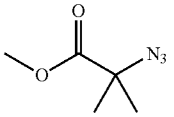 C7 | 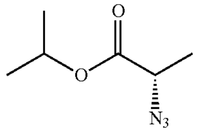 C8 |
| D | 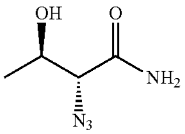 D5 | 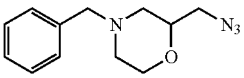 D6 | 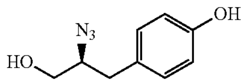 D7 | 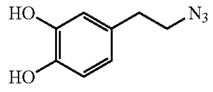 D8 |
| E | 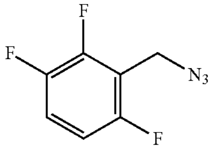 E5 | 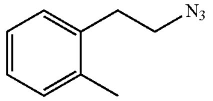 E6 | 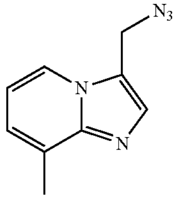 E7 | 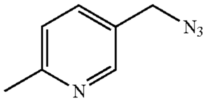 E8 |
| F | 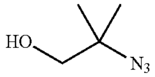 F5 | 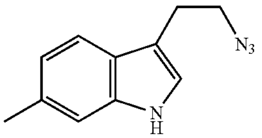 F6 | 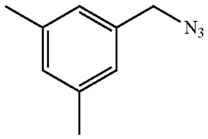 F7 | 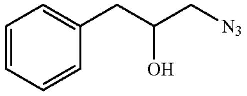 F8 |
| G | 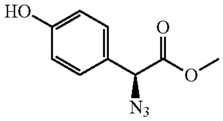 G5 | 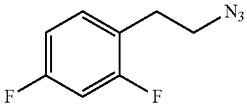 G6 | 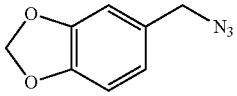 G7 | 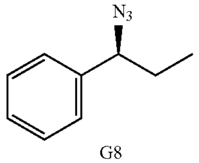 G8 |
| H | 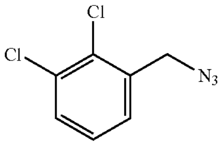 H5 | 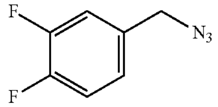 H6 | 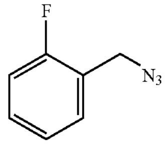 H7 | 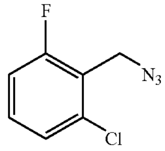 H8 |
| | 9 | 10 | 11 | 12 |
|---|---|---|---|---|
| A | 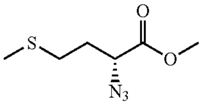 A9 | 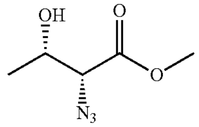 A10 | 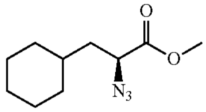 A11 | 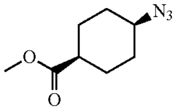 A12 |
| B | 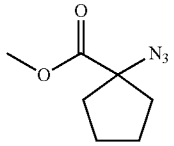 B9 | 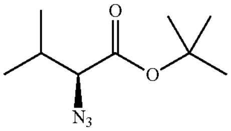 B10 | 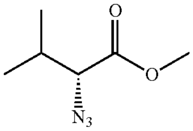 B11 | 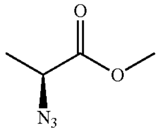 B12 |

-continued
| Plate 6 | | | | |
|---|---|---|---|---|
| C | 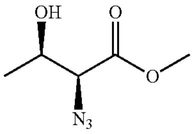 C9 | 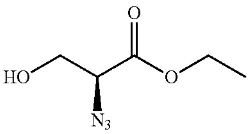 C10 | 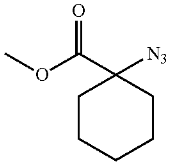 C11 | 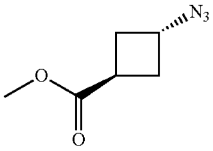 C12 |
| D | 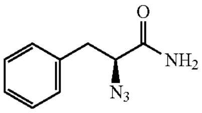 D9 | 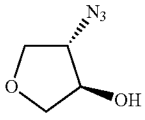 D10 | 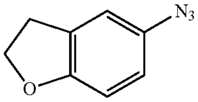 D11 | 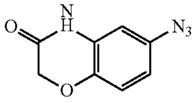 D12 |
| E | 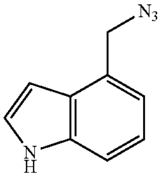 E9 | 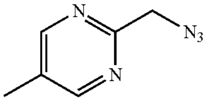 E10 | 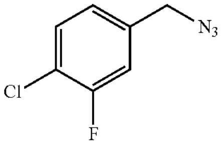 E11 | 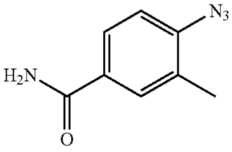 E12 |
| F | 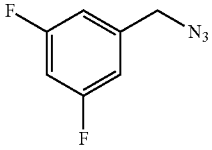 F9 | 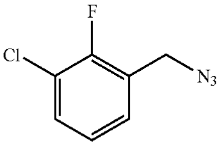 F10 | 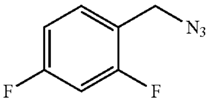 F11 | 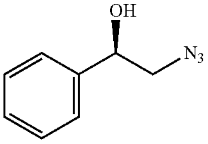 F12 |
| G | 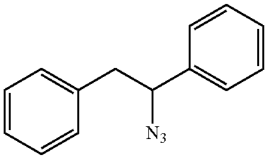 G9 | 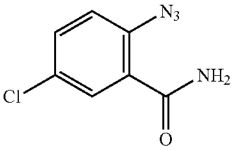 G10 | 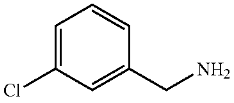 G11 | 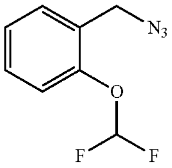 G12 |
| H | 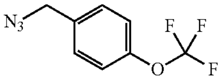 H9 | 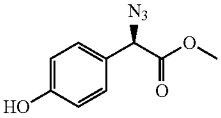 H10 | 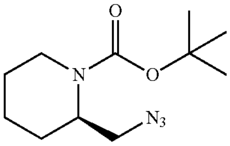 H11 | 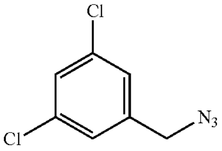 H12 |
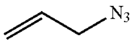
Plate 7 A1
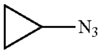
Plate 7 A2
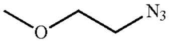
Plate 7 A3
-continued
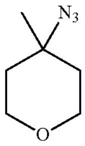
Plate 7 A4
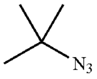
Plate 7 B1

-continued
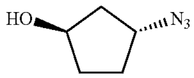
Plate 7 B2
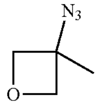
Plate 7 B3
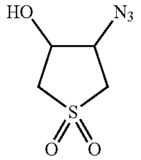
Plate 7 B4
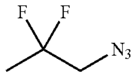
Plate 7 C1
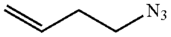
Plate 7 C2
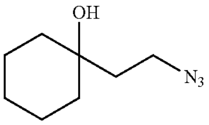 [SMILES: [N-]=[N+]=NCCC1(O)CCCCC1]
Plate 7 C3
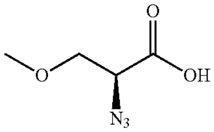
Plate 7 C4
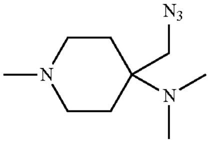
Plate 7 D1
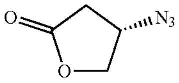
Plate 7 D2
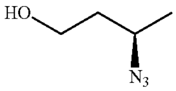
Plate 7 D3
-continued
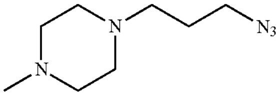
Plate 7 D4
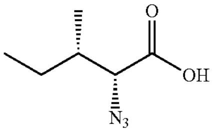
Plate 7 E1
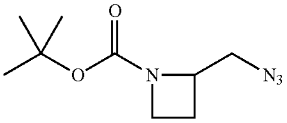
Plate 7 E2
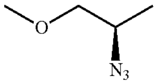
Plate 7 E3
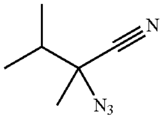
Plate 7 E4
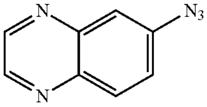
Plate 7 F1
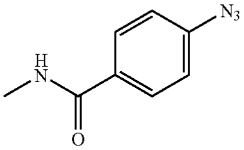
Plate 7 F2
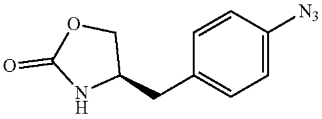
Plate 7 F3
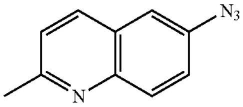
Plate 7 F4
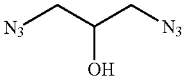
Plate 7 G1

-continued
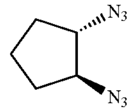
Plate 7 G2
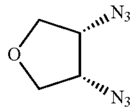
Plate 7 G3
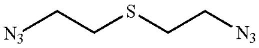
Plate 7 G4
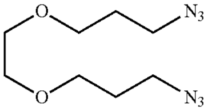
Plate 7 H1
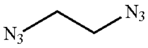
Plate 7 H2
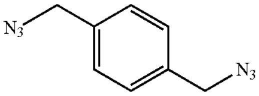
Plate 7 H3
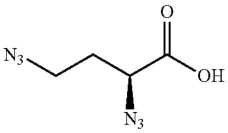
Plate 7 E4
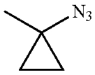
Plate 7 A5
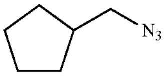
Plate 7 A6
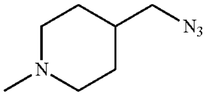
Plate 7 A7
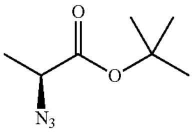
Plate 7 A8
-continued
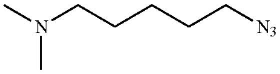
Plate 7 B5
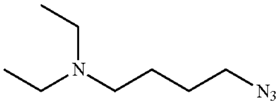
Plate 7 B6
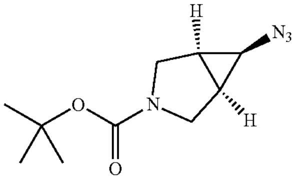 [SMILES: CC(C)(C)OC(=O)N1C[C@@H]2[C@H](C1)[C@@H]2N=[N+]=[N-]]
Plate 7 B7
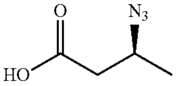
Plate 7 B8
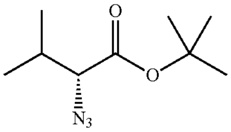
Plate 7 C5
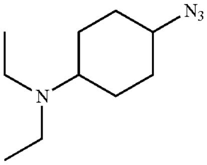
Plate 7 C6
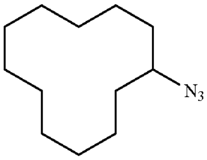 [SMILES: [N-]=[N+]=NC1CCCCCCCCCCC1]
Plate 7 C7
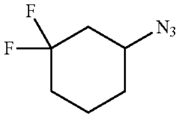 [SMILES: [N-]=[N+]=NC1CCCC(F)(F)C1]
Plate 7 C8

-continued
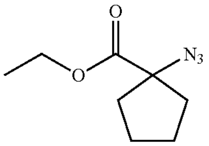
Plate 7 D5
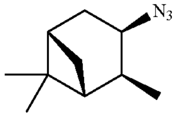
Plate 7 D6
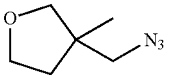
Plate 7 D7
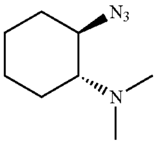
Plate 7 D8
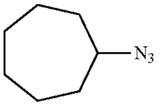
Plate 7 E5
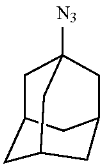 [SMILES: [N-]=[N+]=NC12CC3CC(CC(C3)C1)C2]
Plate 7 E6
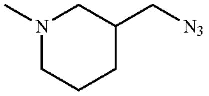
Plate 7 E7
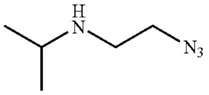
Plate 7 E8
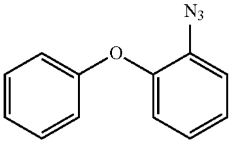 [SMILES: [N-]=[N+]=Nc1ccccc1Oc1ccccc1]
Plate 7 F5
-continued
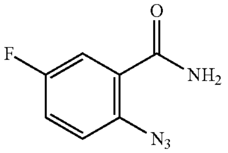 [SMILES: [N-]=[N+]=Nc1ccc(F)cc1C(N)=O]
Plate 7 F6
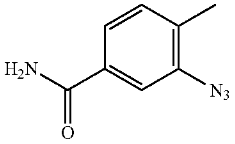
Plate 7 F7
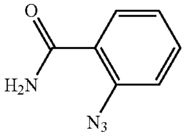
Plate 7 F8
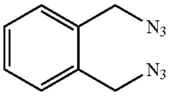 [SMILES: [N-]=[N+]=NCc1ccccc1CN=[N+]=[N-]]
Plate 7 G5
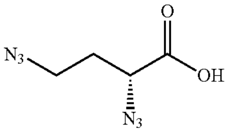
Plate 7 G6
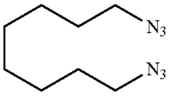 [SMILES: [N-]=[N+]=NCCCCCCCCN=[N+]=[N-]]
Plate 7 G7
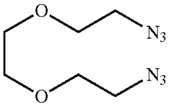 [SMILES: [N-]=[N+]=NCCOCCOCCN=[N+]=[N-]]
Plate 7 G8
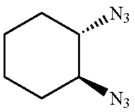
Plate 7 H5
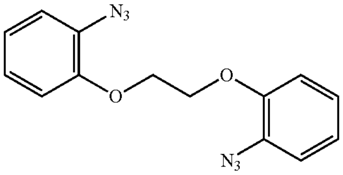 [SMILES: [N-]=[N+]=Nc1ccccc1OCCOc1ccccc1N=[N+]=[N-]]
Plate 7 H6

-continued
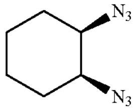
Plate 7 H7
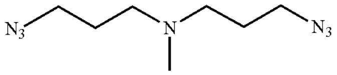
Plate 7 H8
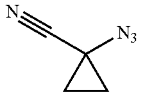
Plate 7 A9
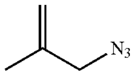
Plate 7 A10
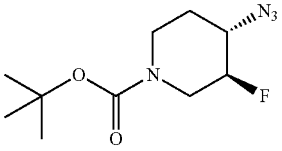 [SMILES: CC(C)(C)OC(=O)N1CC[C@H](N=[N+]=[N-])[C@@H](F)C1]
Plate 7 A11
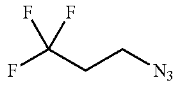
Plate 7 A12
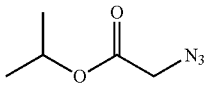
Plate 7 B9
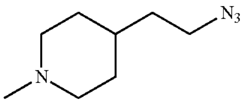
Plate 7 B10
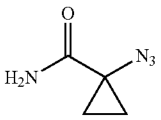
Plate 7 B11
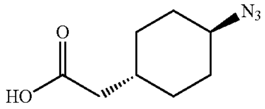 [SMILES: [N-]=[N+]=N[C@H]1CC[C@H](CC(=O)O)CC1]
Plate 7 B12
-continued
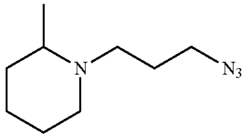
Plate 7 C9
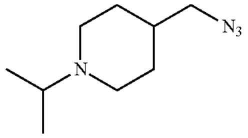
Plate 7 C10
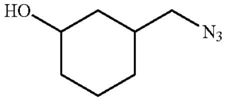 [SMILES: [N-]=[N+]=NCC1CCCC(O)C1]
Plate 7 C11
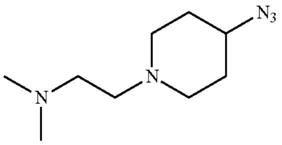
Plate 7 C12
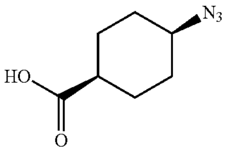 [SMILES: [N-]=[N+]=N[C@H]1CC[C@@H](C(=O)O)CC1]
Plate 7 D9
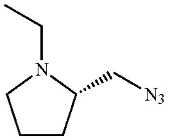
Plate 7 D10
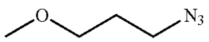
Plate 7 D11
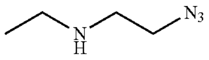
Plate 7 D12
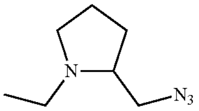
Plate 7 E9

-continued
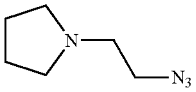
Plate 7 E10
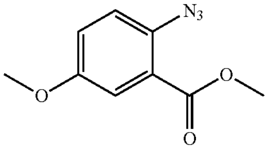
Plate 7 E11
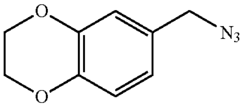 [SMILES: [N-]=[N+]=NCc1ccc2c(c1)OCCO2]
Plate 7 E12
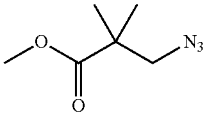
Plate 7 F9
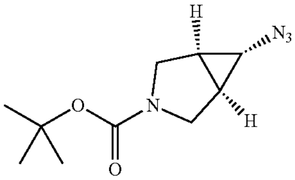 [SMILES: CC(C)(C)OC(=O)N1C[C@@H]2[C@H](C1)[C@H]2N=[N+]=[N-]]
Plate 7 F10
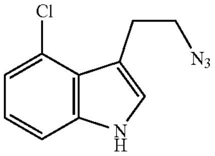 [SMILES: [N-]=[N+]=NCCc1c[nH]c2cccc(Cl)c12]
Plate 7 F11
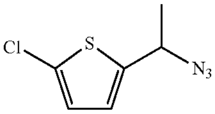
Plate 7 F12
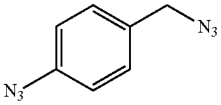 [SMILES: [N-]=[N+]=NCc1ccc(N=[N+]=[N-])cc1]
Plate 7 G9
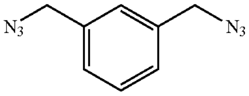 [SMILES: [N-]=[N+]=NCc1cccc(CN=[N+]=[N-])c1]
Plate 7 G10
-continued
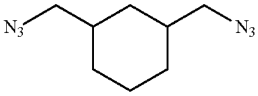 [SMILES: [N-]=[N+]=NCC1CCCC(CN=[N+]=[N-])C1]
Plate 7 G11
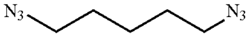 [SMILES: [N-]=[N+]=NCCCCCN=[N+]=[N-]]
Plate 7 G12
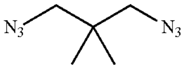
Plate 7 H9
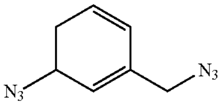
Plate 7 H10
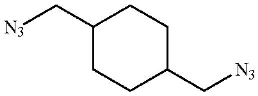
Plate 7 H11
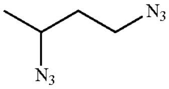
Plate 7 H12
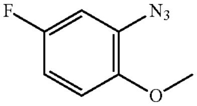
Plate 8 A1
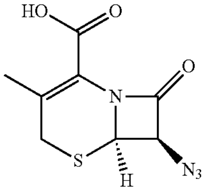
Plate 8 A2
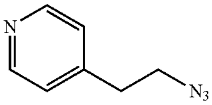
Plate 8 A3
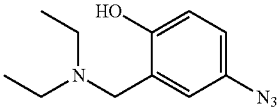
Plate 8 A4

-continued
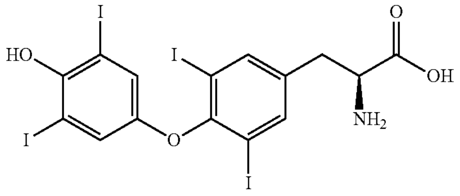
Plate 8 B1
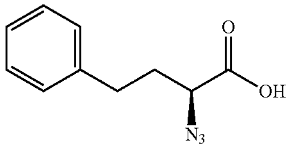
Plate 8 B2
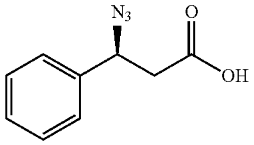
Plate 8 C3
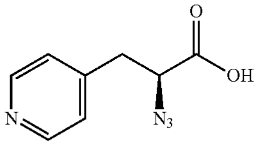
Plate 8 B4
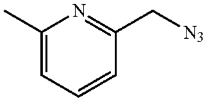
Plate 8 C1
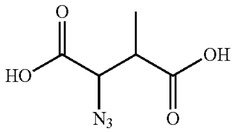
Plate 8 C2
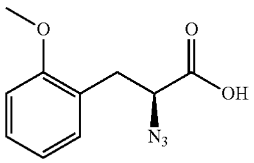
Plate 8 C3
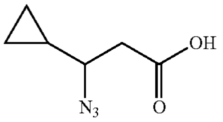
Plate 8 C4
-continued
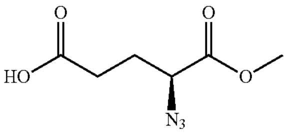
Plate 8 D1
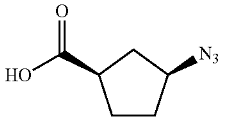
Plate 8 D2
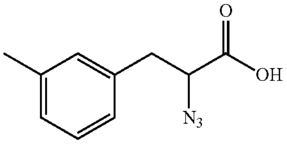
Plate 8 D3
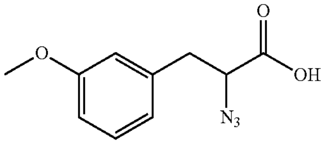
Plate 8 D4
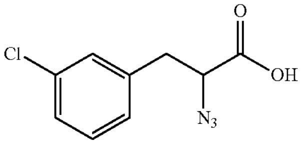
Plate 8 D4
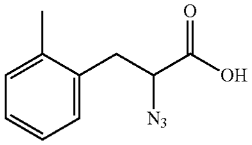
Plate 8 E2
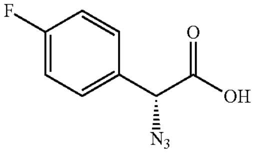
Plate 8 E3
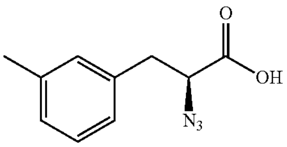
Plate 8 E4

-continued
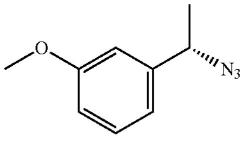
Plate 8 F1
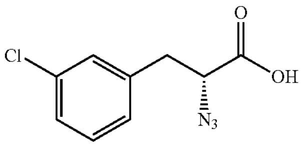
Plate 8 F2
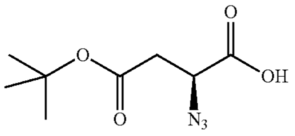
Plate 8 F3
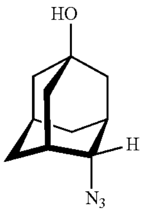
Plate 8 F4
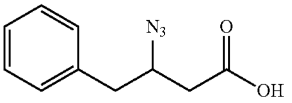
Plate 8 G1
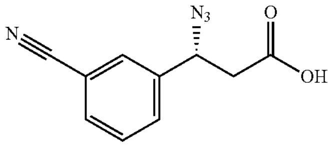
Plate 8 G2
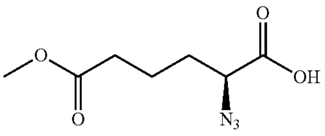
Plate 8 G3
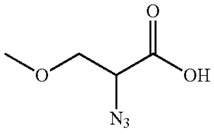
Plate 8 G4
-continued
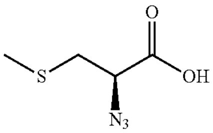
Plate 8 H1
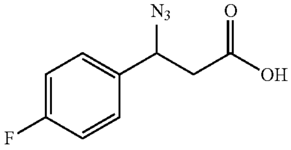 [SMILES: [N-]=[N+]=NC(CC(=O)O)c1ccc(F)cc1]
Plate 8 H2
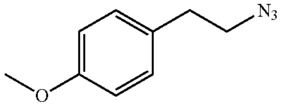
Plate 8 H3
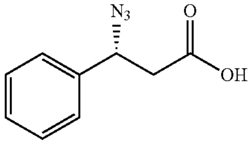 [SMILES: [N-]=[N+]=N[C@H](CC(=O)O)c1ccccc1]
Plate 8 H4
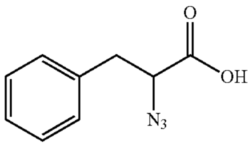 [SMILES: [N-]=[N+]=NC(Cc1ccccc1)C(=O)O]
Plate 8 A5
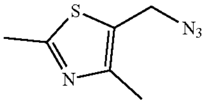
Plate 8 A6
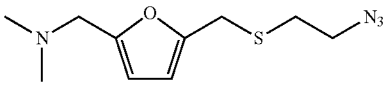 [SMILES: CN(C)Cc1ccc(CSCCN=[N+]=[N-])o1]
Plate 8 A7
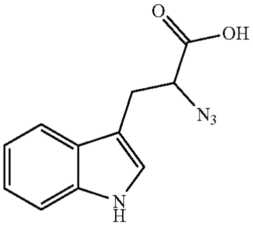 [SMILES: [N-]=[N+]=NC(Cc1c[nH]c2ccccc12)C(=O)O]
Plate 8 A8

-continued
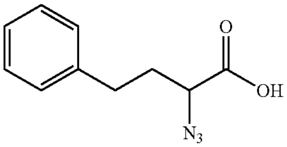 [SMILES: [N-]=[N+]=NC(CCc1ccccc1)C(=O)O]
Plate 8 B5
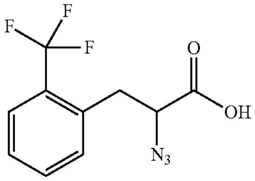 [SMILES: [N-]=[N+]=NC(Cc1ccccc1C(F)(F)F)C(=O)O]
Plate 8 B6
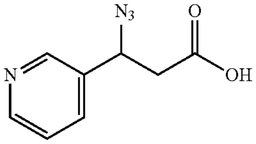 [SMILES: [N-]=[N+]=NC(CC(=O)O)c1cccnc1]
Plate 8 B7
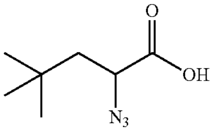
Plate 8 B8
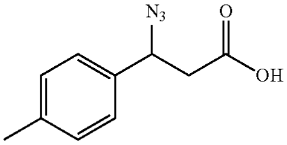
Plate 8 C5
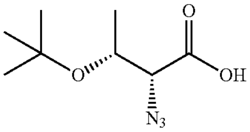
Plate 8 C6
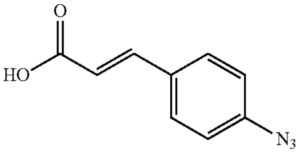 [SMILES: [N-]=[N+]=Nc1ccc(/C=C/C(=O)O)cc1]
Plate 8 C7
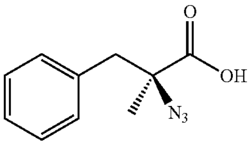
Plate 8 C8
-continued
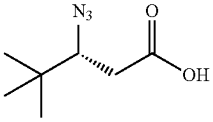
Plate 8 D5
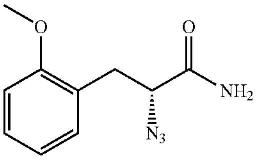 [SMILES: COc1ccccc1C[C@@H](N=[N+]=[N-])C(N)=O]
Plate 8 D6
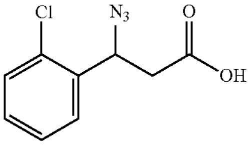 [SMILES: [N-]=[N+]=NC(CC(=O)O)c1ccccc1Cl]
Plate 8 D7
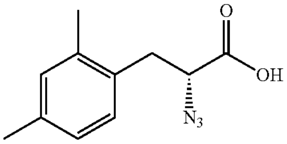 [SMILES: Cc1ccc(C[C@@H](N=[N+]=[N-])C(=O)O)c(C)c1]
Plate 8 D8
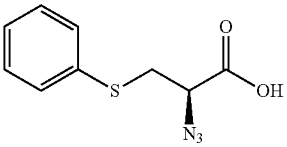 [SMILES: [N-]=[N+]=N[C@@H](CSc1ccccc1)C(=O)O]
Plate 8 E5
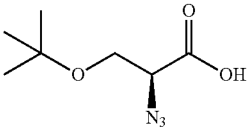
Plate 8 E6
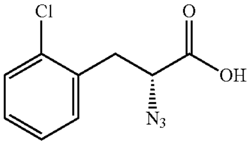 [SMILES: [N-]=[N+]=N[C@H](Cc1ccccc1Cl)C(=O)O]
Plate 8 E7
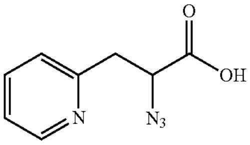 [SMILES: [N-]=[N+]=NC(Cc1ccccn1)C(=O)O]
Plate 8 E8

-continued
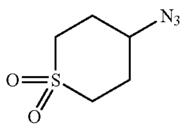 [SMILES: [N-]=[N+]=NC1CCS(=O)(=O)CC1]
Plate 8 F5
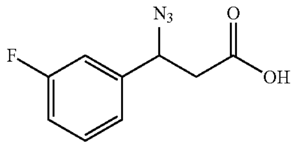 [SMILES: [N-]=[N+]=NC(CC(=O)O)c1cccc(F)c1]
Plate 8 F6
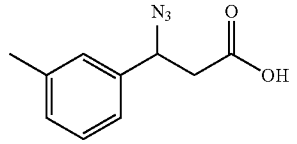
Plate 8 F7
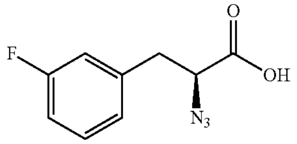 [SMILES: [N-]=[N+]=N[C@@H](Cc1cccc(F)c1)C(=O)O]
Plate 8 F8
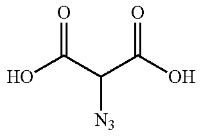
Plate 8 G5
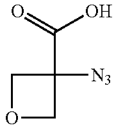
Plate 8 G6
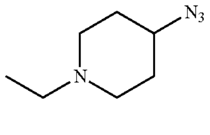
Plate 8 G7
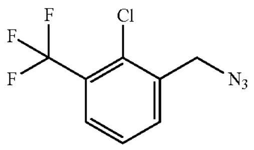 [SMILES: [N-]=[N+]=NCc1cccc(C(F)(F)F)c1Cl]
Plate 8 G8
-continued
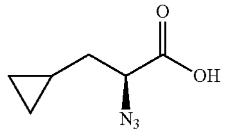 [SMILES: [N-]=[N+]=N[C@@H](CC1CC1)C(=O)O]
Plate 8 H5
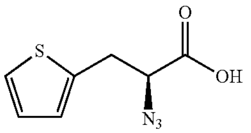 [SMILES: [N-]=[N+]=N[C@@H](Cc1cccs1)C(=O)O]
Plate 8 H6
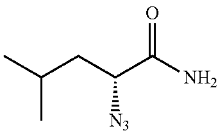
Plate 8 H7
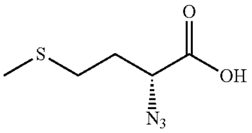
Plate 8 H8
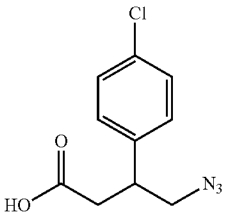 [SMILES: [N-]=[N+]=NCC(CC(=O)O)c1ccc(Cl)cc1]
Plate 8 A9
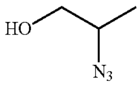
Plate 8 A10
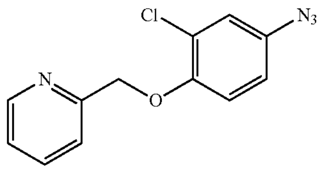 [SMILES: [N-]=[N+]=Nc1ccc(OCc2ccccn2)c(Cl)c1]
Plate 8 A11
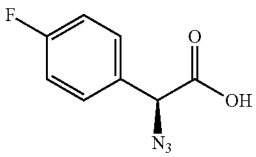 [SMILES: [N-]=[N+]=N[C@H](C(=O)O)c1ccc(F)cc1]
Plate 8 A12

-continued
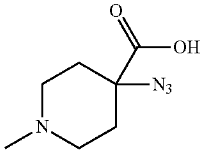
Plate 8 B9
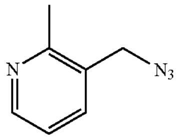
Plate 8 B10
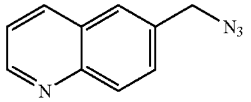 [SMILES: [N-]=[N+]=NCc1ccc2ncccc2c1]
Plate 8 B11
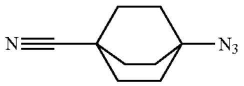 [SMILES: N#CC12CCC(N=[N+]=[N-])(CC1)CC2]
Plate 8 B12
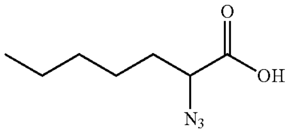
Plate 8 C9
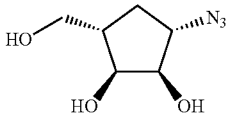
Plate 8 C10
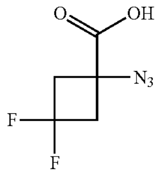
Plate 8 C11
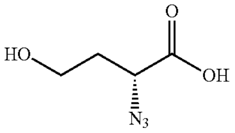
Plate 8 C12
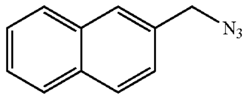
Plate 8 D9
-continued
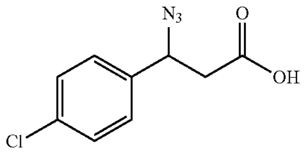
Plate 8 D10
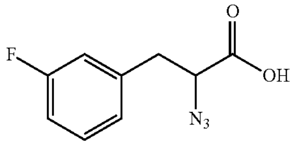
Plate 8 D11
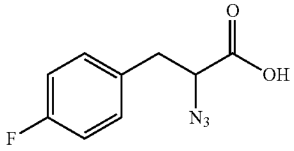
Plate 8 D12
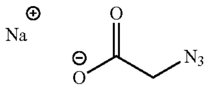
Plate 8 E9
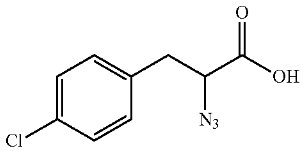
Plate 8 E10
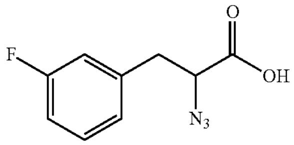
Plate 8 D11
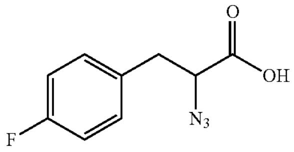
Plate 8 D12
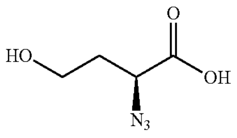
Plate 8 F9

-continued
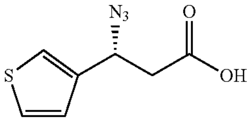
Plate 8 F10
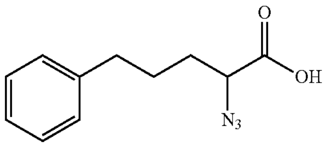
Plate 8 F11
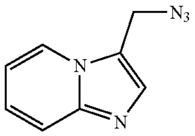 [SMILES: [N-]=[N+]=NCc1cnc2ccccn12]
Plate 8 F12
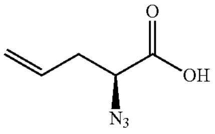
Plate 8 G9
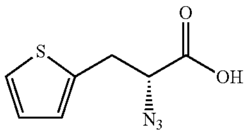 [SMILES: [N-]=[N+]=N[C@H](Cc1cccs1)C(=O)O]
Plate 8 G10
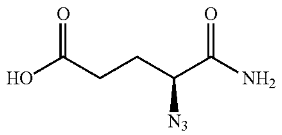
Plate 8 G11
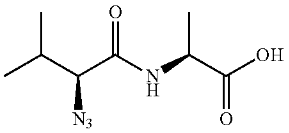
Plate 8 G12
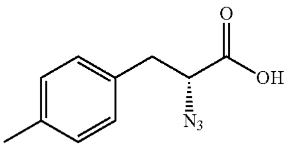
Plate 8 H9
-continued
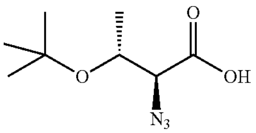
Plate 8 H10
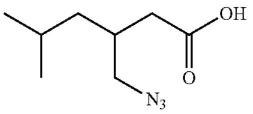
Plate 8 H11
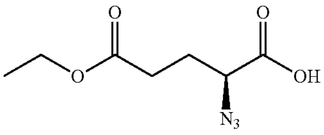
Plate 8 H12
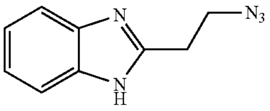 [SMILES: [N-]=[N+]=NCCc1nc2ccccc2[nH]1]
Plate 10 A1
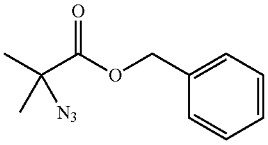 [SMILES: CC(C)(N=[N+]=[N-])C(=O)OCc1ccccc1]
Plate 10 A2
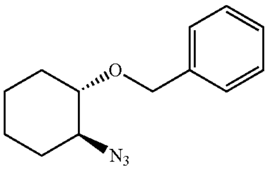 [SMILES: [N-]=[N+]=N[C@H]1CCCC[C@@H]1OCc1ccccc1]
Plate 10 A3
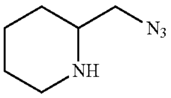
Plate 10 A4
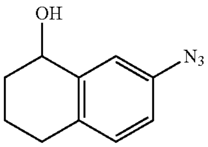 [SMILES: [N-]=[N+]=Nc1ccc2c(c1)C(O)CCC2]
Plate 10 B1

-continued
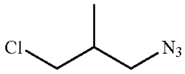
Plate 10 B2
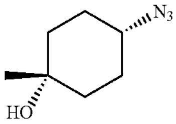
Plate 10 B3
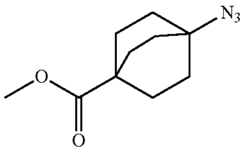
Plate 10 B4
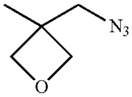
Plate 10 C1
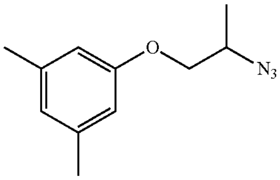
Plate 10 C2
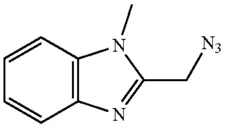
Plate 10 C3
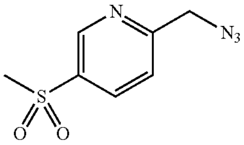
Plate 10 C4
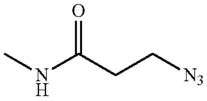
Plate 10 D1
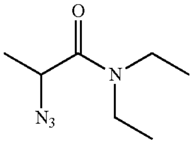
Plate 10 D2
-continued
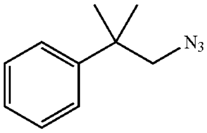
Plate 10 D3
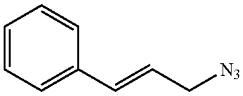 [SMILES: [N-]=[N+]=NC/C=C/c1ccccc1]
Plate 10 D4
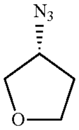
Plate 10 E1
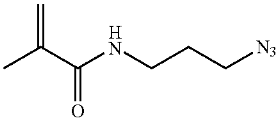
Plate 10 E2
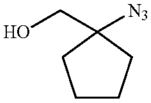
Plate 10 E3
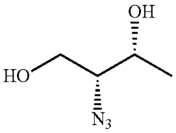
Plate 10 E4
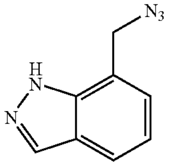 [SMILES: [N-]=[N+]=NCc1cccc2cn[nH]c12]
Plate 10 F1
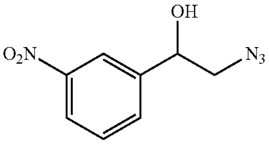
Plate 10 F2
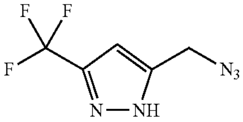
Plate 10 F3

-continued
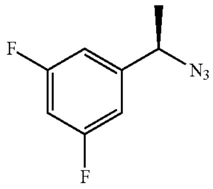
Plate 10 F4
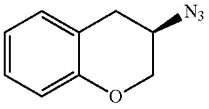
Plate 10 G1
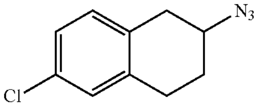
Plate 10 G2
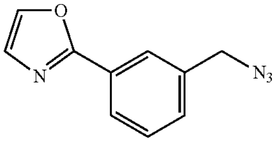
Plate 10 G3
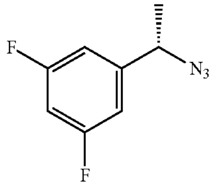
Plate 10 G4
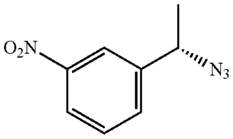
Plate 10 H1
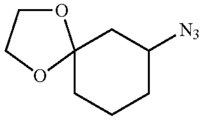
Plate 10 H2
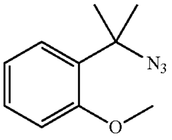
Plate 10 H3
-continued
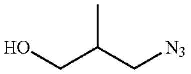
Plate 10 H4
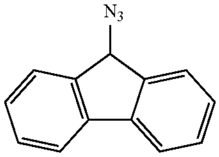
Plate 10 A5
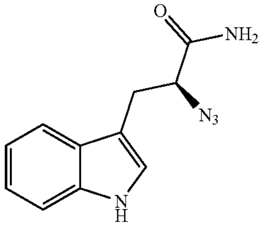
Plate 10 A6
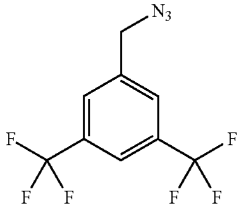
Plate 10 A7
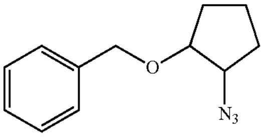
Plate 10 A8
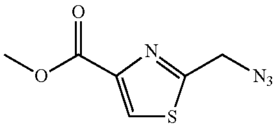
Plate 10 B5
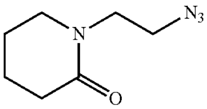 [SMILES: [N-]=[N+]=NCCN1CCCCC1=O]
Plate 10 B6
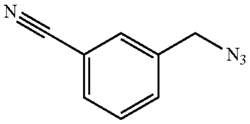 [SMILES: N#Cc1cccc(CN=[N+]=[N-])c1]
Plate 10 B7

-continued
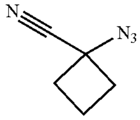
Plate 10 B8
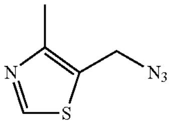
Plate 10 C5
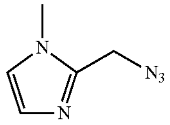
Plate 10 C6
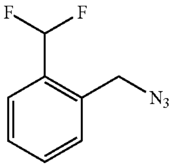 [SMILES: [N-]=[N+]=NCc1ccccc1C(F)F]
Plate 10 C7
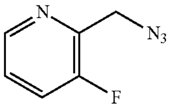 [SMILES: [N-]=[N+]=NCc1ncccc1F]
Plate 10 C8
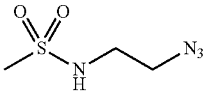
Plate 10 D5
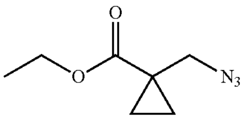
Plate 10 D6
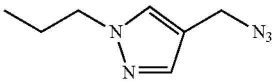
Plate 10 D7
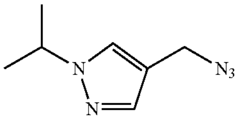
Plate 10 D8
-continued
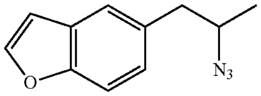
Plate 10 E5
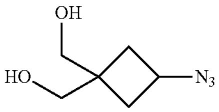 [SMILES: [N-]=[N+]=NC1CC(CO)(CO)C1]
Plate 10 E6
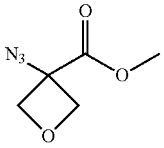
Plate 10 E7
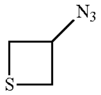
Plate 10 E8
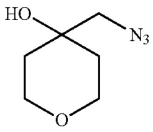 [SMILES: [N-]=[N+]=NCC1(O)CCOCC1]
Plate 10 F5
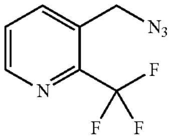 [SMILES: [N-]=[N+]=NCc1cccnc1C(F)(F)F]
Plate 10 F6
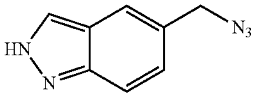 [SMILES: [N-]=[N+]=NCc1ccc2n[nH]cc2c1]
Plate 10 F7
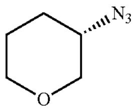
Plate 10 F8
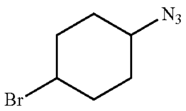
Plate 10 G5

-continued
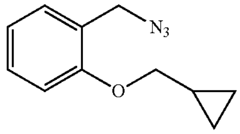 [SMILES: [N-]=[N+]=NCc1ccccc1OCC1CC1]
Plate 10 G6
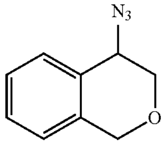 [SMILES: [N-]=[N+]=NC1COCc2ccccc21]
Plate 10 G7
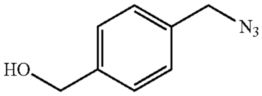 [SMILES: [N-]=[N+]=NCc1ccc(CO)cc1]
Plate 10 G8
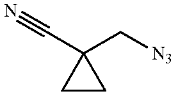
Plate 10 H5
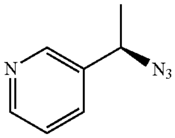
Plate 10 H6
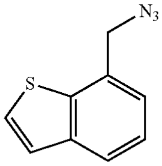 [SMILES: [N-]=[N+]=NCc1cccc2ccsc12]
Plate 10 H7
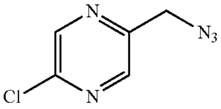 [SMILES: [N-]=[N+]=NCc1cnc(Cl)cn1]
Plate 10 H8
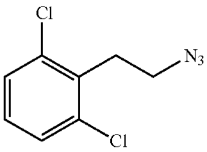 [SMILES: [N-]=[N+]=NCCc1c(Cl)cccc1Cl]
Plate 10 A9
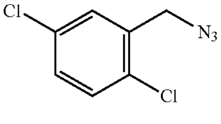 [SMILES: [N-]=[N+]=NCc1cc(Cl)ccc1Cl]
Plate 10 A10
-continued
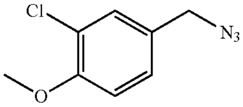
Plate 10 A11
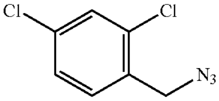
Plate 10 A12
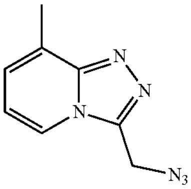
Plate 10 B9
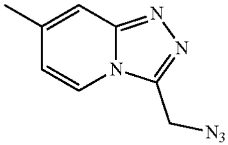
Plate 10 B10
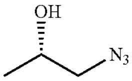
Plate 10 B11
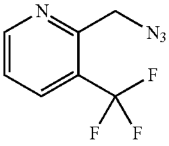
Plate 10 B12
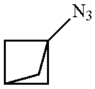
Plate 10 C9
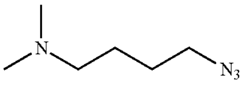
Plate 10 C10
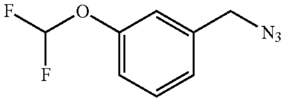
Plate 10 C11
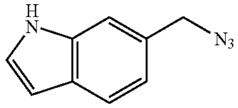
Plate 10 C12

-continued
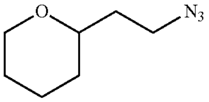
Plate 10 D9
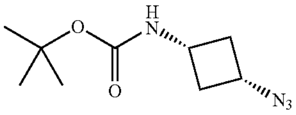
Plate 10 D10
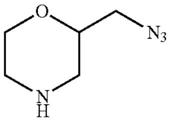
Plate 10 D11
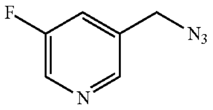
Plate 10 D12
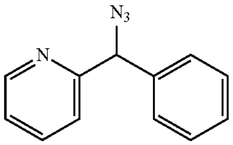
Plate 10 E9
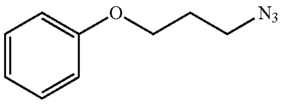
Plate 10 E10
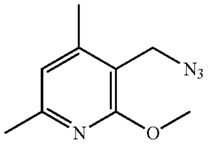
Plate 10 E11
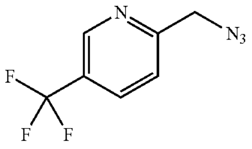
Plate 10 E12
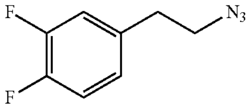
Plate 10 F9
-continued
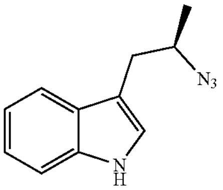
Plate 10 F10
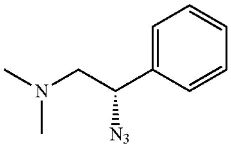
Plate 10 F11
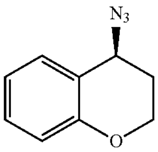
Plate 10 F12
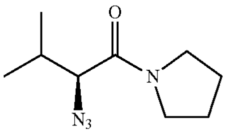
Plate 10 G9
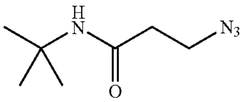
Plate 10 G10
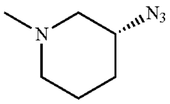
Plate 10 G11
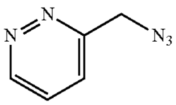
Plate 10 G12
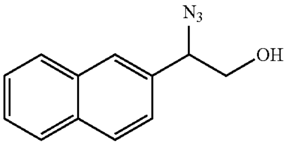
Plate 10 H9
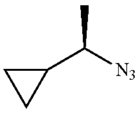
Plate 10 H10

-continued
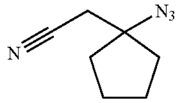
Plate 10 H11
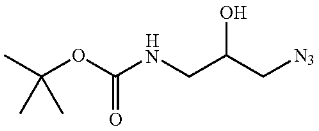
Plate 10 H12
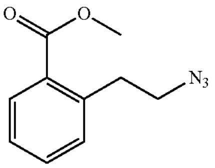
Plate 11 A1
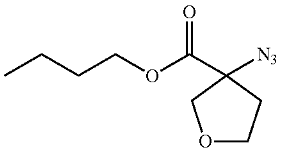
Plate 11 A2
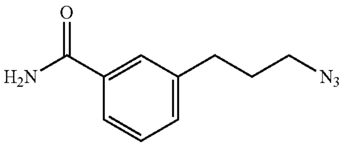
Plate 11 A3
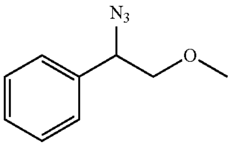
Plate 11 A4
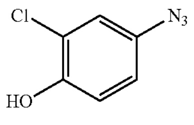
Plate 11 B1
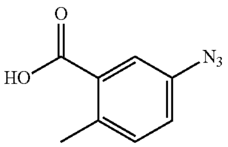
Plate 11 B2
-continued
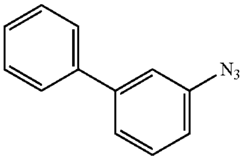
Plate 11 B3
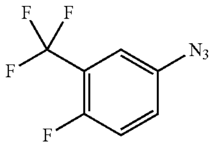
Plate 11 B4
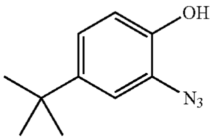
Plate 11 C1
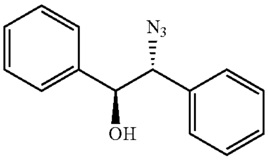
Plate 11 C2
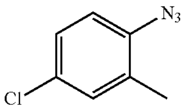
Plate 11 C3
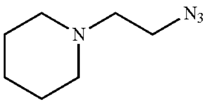
Plate 11 C4
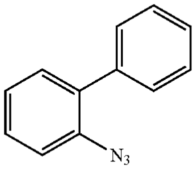
Plate 11 D1
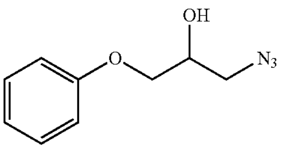
Plate 11 D2

-continued
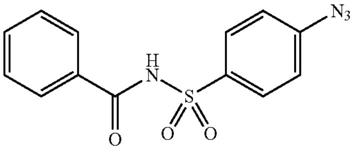
Plate 11 D3
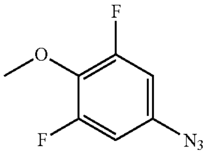
Plate 11 D4
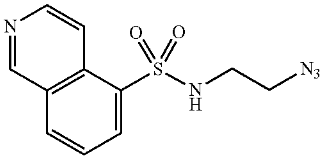 [SMILES: [N-]=[N+]=NCCNS(=O)(=O)c1cccc2cnccc12]
Plate 11 E1
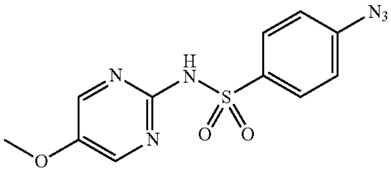 [SMILES: COc1cnc(NS(=O)(=O)c2ccc(N=[N+]=[N-])cc2)nc1]
Plate 11 E2
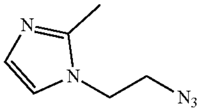
Plate 11 E3
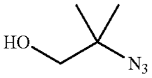
Plate 11 E4
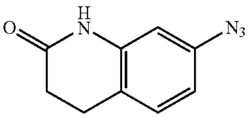 [SMILES: [N-]=[N+]=Nc1ccc2c(c1)NC(=O)CC2]
Plate 11 F1
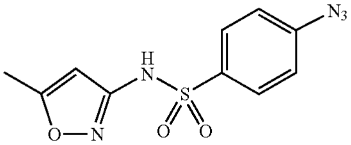 [SMILES: Cc1cc(NS(=O)(=O)c2ccc(N=[N+]=[N-])cc2)no1]
Plate 11 F2
-continued
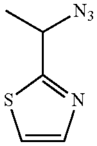
Plate 11 F3
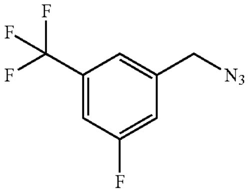
Plate 11 F4
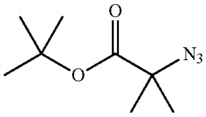
Plate 11 G1
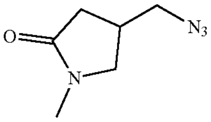
Plate 11 G2
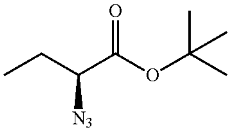
Plate 11 G3
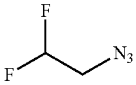
Plate 11 G4
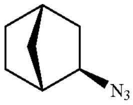
Plate 11 H1
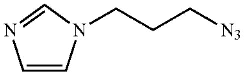 [SMILES: [N-]=[N+]=NCCCn1ccnc1]
Plate 11 H2
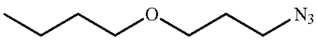
Plate 11 H3

-continued
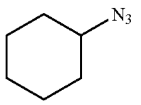
Plate 11 H4
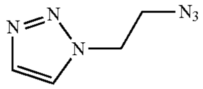
Plate 11 A5
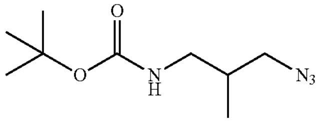
Plate 11 A6
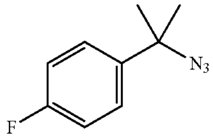
Plate 11 A7
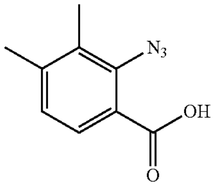
Plate 11 A8
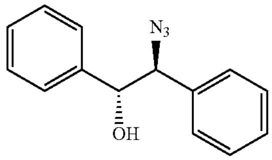
Plate 11 B5
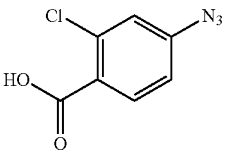
Plate 11 B6
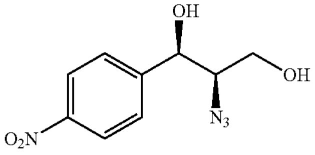
Plate 11 B7
-continued
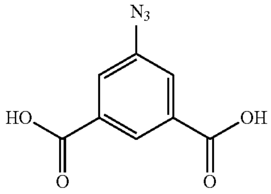
Plate 11 B8
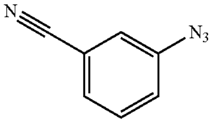
Plate 11 C5
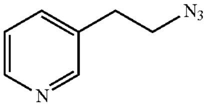
Plate 11 C6
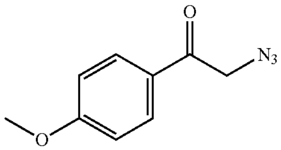
Plate 11 C7
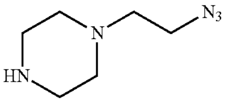
Plate 11 C8
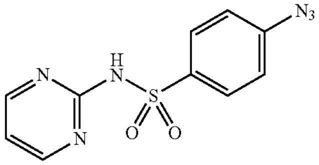
Plate 11 D5
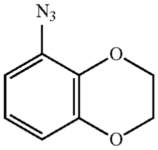 [SMILES: [N-]=[N+]=Nc1cccc2c1OCCO2]
Plate 11 D6
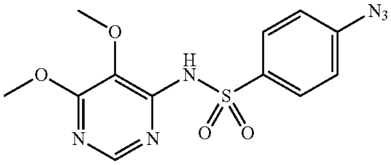 [SMILES: COc1ncnc(NS(=O)(=O)c2ccc(N=[N+]=[N-])cc2)c1OC]
Plate 11 D7

-continued
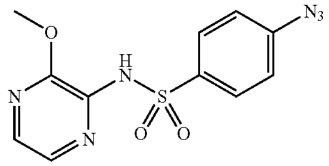 [SMILES: COc1nccnc1NS(=O)(=O)c1ccc(N=[N+]=[N-])cc1]
Plate 11 D8
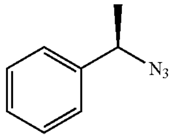
Plate 11 E5
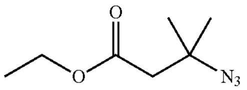
Plate 11 E6
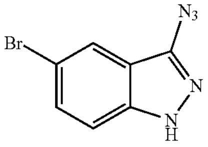 [SMILES: [N-]=[N+]=Nc1n[nH]c2ccc(Br)cc12]
Plate 11 E7
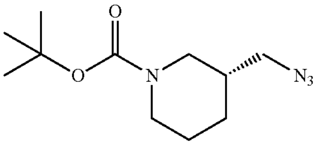 [SMILES: CC(C)(C)OC(=O)N1CCC[C@@H](CN=[N+]=[N-])C1]
Plate 11 E8
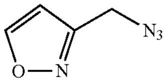
Plate 11 F5
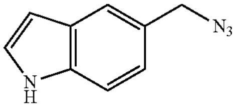 [SMILES: [N-]=[N+]=NCc1ccc2[nH]ccc2c1]
Plate 11 F6
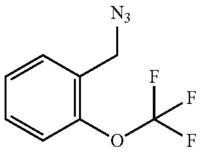 [SMILES: [N-]=[N+]=NCc1ccccc1OC(F)(F)F]
Plate 11 F7
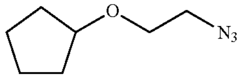 [SMILES: [N-]=[N+]=NCCOC1CCCC1]
Plate 11 F8
-continued
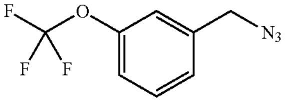 [SMILES: [N-]=[N+]=NCc1cccc(OC(F)(F)F)c1]
Plate 11 G5
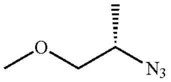
Plate 11 G6
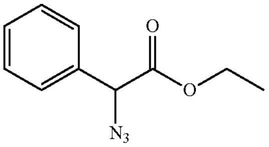
Plate 11 G7
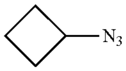
Plate 11 G8
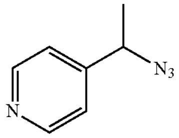
Plate 11 H5
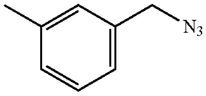
Plate 11 H6
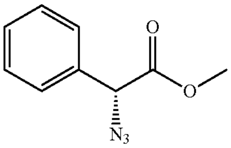
Plate 11 H7
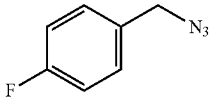 [SMILES: [N-]=[N+]=NCc1ccc(F)cc1]
Plate 11 H8
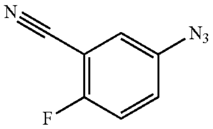 [SMILES: N#Cc1cc(N=[N+]=[N-])ccc1F]
Plate 11 A9

-continued
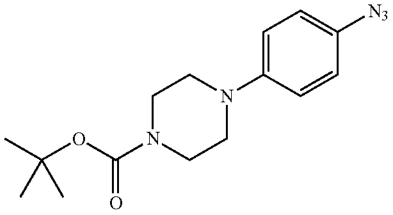 [SMILES: CC(C)(C)OC(=O)N1CCN(c2ccc(N=[N+]=[N-])cc2)CC1]
Plate 11 A10
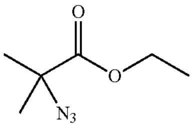
Plate 11 A11
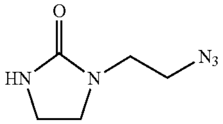 [SMILES: [N-]=[N+]=NCCN1CCNC1=O]
Plate 11 A12
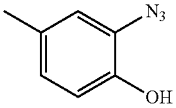
Plate 11 B9
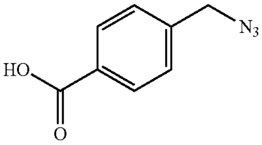 [SMILES: [N-]=[N+]=NCc1ccc(C(=O)O)cc1]
Plate 11 B10
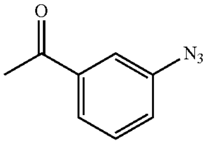
Plate 11 B11
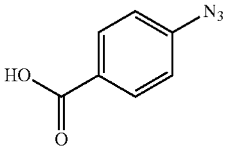 [SMILES: [N-]=[N+]=Nc1ccc(C(=O)O)cc1]
Plate 11 B12
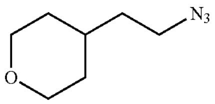 [SMILES: [N-]=[N+]=NCCC1CCOCC1]
Plate 11 C9
-continued
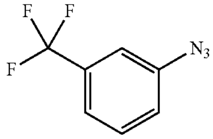 [SMILES: [N-]=[N+]=Nc1cccc(C(F)(F)F)c1]
Plate 11 C10
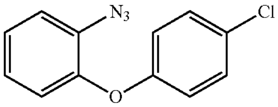 [SMILES: [N-]=[N+]=Nc1ccccc1Oc1ccc(Cl)cc1]
Plate 11 C11
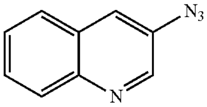 [SMILES: [N-]=[N+]=Nc1cnc2ccccc2c1]
Plate 11 C12
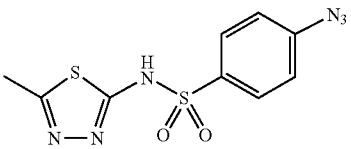 [SMILES: Cc1nnc(NS(=O)(=O)c2ccc(N=[N+]=[N-])cc2)s1]
Plate 11 D9
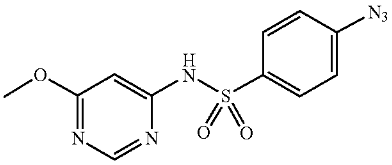 [SMILES: COc1cc(NS(=O)(=O)c2ccc(N=[N+]=[N-])cc2)ncn1]
Plate 11 D10
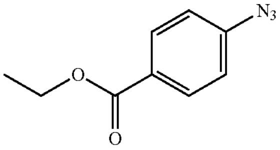
Plate 11 D11
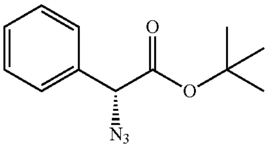 [SMILES: CC(C)(C)OC(=O)[C@H](N=[N+]=[N-])c1ccccc1]
Plate 11 D12
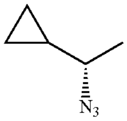
Plate 11 E9

-continued
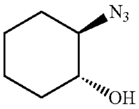
Plate 11 E10
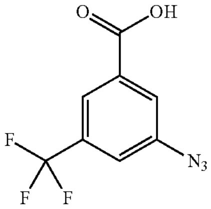 [SMILES: [N-]=[N+]=Nc1cc(C(=O)O)cc(C(F)(F)F)c1]
Plate 11 E11
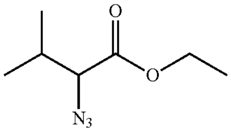
Plate 11 E12
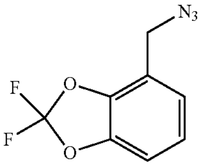 [SMILES: [N-]=[N+]=NCc1cccc2c1OC(F)(F)O2]
Plate 11 F9
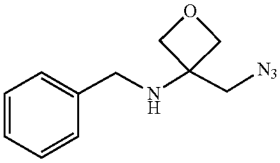 [SMILES: [N-]=[N+]=NCC1(NCc2ccccc2)COC1]
Plate 11 F10
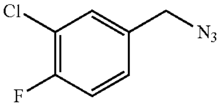 [SMILES: [N-]=[N+]=NCc1ccc(F)c(Cl)c1]
Plate 11 F11
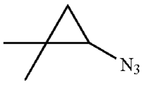
Plate 11 F12
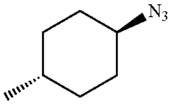
Plate 11 G9
-continued
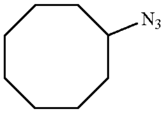 [SMILES: [N-]=[N+]=NC1CCCCCCC1]
Plate 11 G10
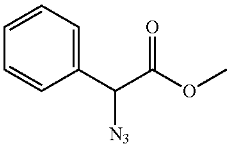
Plate 11 G11
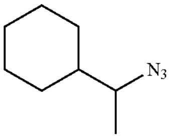
Plate 11 G12
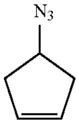
Plate 11 H9
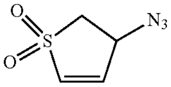
Plate 11 H10
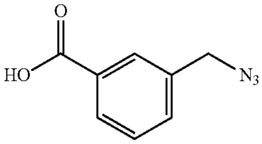 [SMILES: [N-]=[N+]=NCc1cccc(C(=O)O)c1]
Plate 11 H11
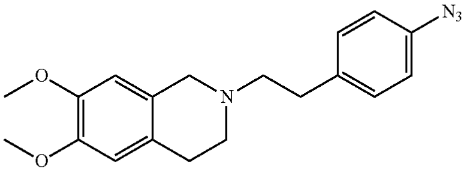 [SMILES: COc1cc2c(cc1OC)CN(CCc1ccc(N=[N+]=[N-])cc1)CC2]
Plate 11 H12
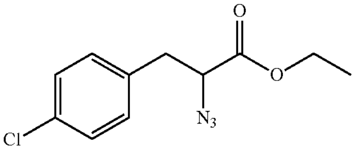 [SMILES: CCOC(=O)C(Cc1ccc(Cl)cc1)N=[N+]=[N-]]
Plate 12 A1

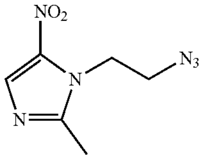
Plate 12 A2
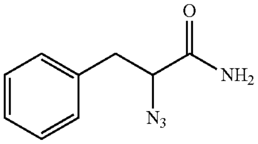 [SMILES: [N-]=[N+]=NC(Cc1ccccc1)C(N)=O]
Plate 12 A3
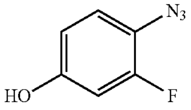 [SMILES: [N-]=[N+]=Nc1ccc(O)cc1F]
Plate 12 A4
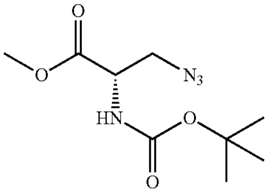 [SMILES: COC(=O)[C@H](CN=[N+]=[N-])NC(=O)OC(C)(C)C]
Plate 12 B1
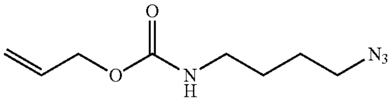
Plate 12 B2
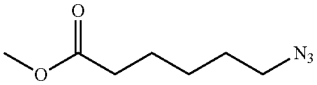
Plate 12 B3
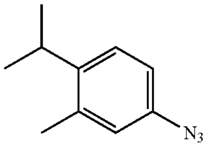
Plate 12 B4
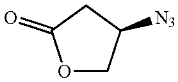
Plate 12 C1
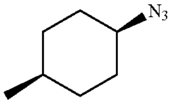
Plate 12 C2
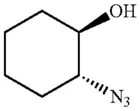
Plate 12 C3
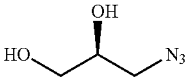
Plate 12 C4
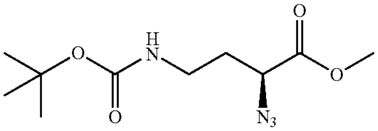 [SMILES: COC(=O)[C@H](CCNC(=O)OC(C)(C)C)N=[N+]=[N-]]
Plate 12 D1
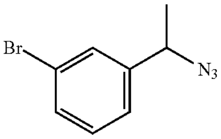
Plate 12 D2
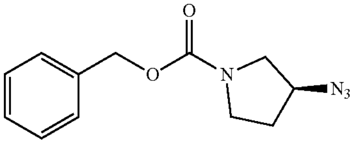 [SMILES: [N-]=[N+]=N[C@H]1CCN(C(=O)OCc2ccccc2)C1]
Plate 12 D3
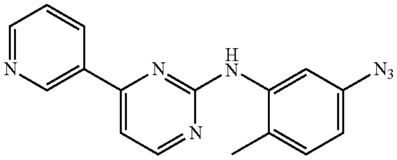 [SMILES: Cc1ccc(N=[N+]=[N-])cc1Nc1nccc(-c2cccnc2)n1]
Plate 12 D4
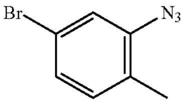
Plate 12 E1
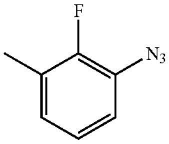
Plate 12 E2
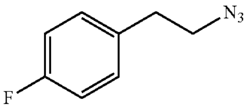 [SMILES: [N-]=[N+]=NCCc1ccc(F)cc1]
Plate 12 E3

-continued
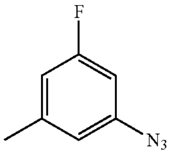
Plate 12 E4
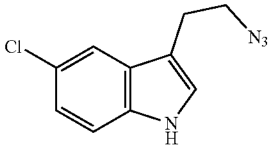 [SMILES: [N-]=[N+]=NCCc1c[nH]c2ccc(Cl)cc12]
Plate 12 F1
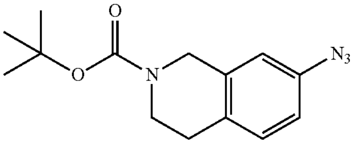 [SMILES: CC(C)(C)OC(=O)N1CCc2ccc(N=[N+]=[N-])cc2C1]
Plate 12 F2
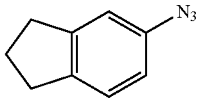 [SMILES: [N-]=[N+]=Nc1ccc2c(c1)CCC2]
Plate 12 F3
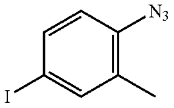
Plate 12 F4
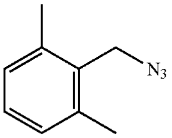
Plate 12 G1
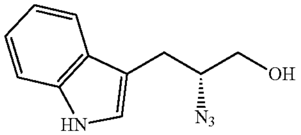 [SMILES: [N-]=[N+]=N[C@@H](CO)Cc1c[nH]c2ccccc12]
Plate 12 G2
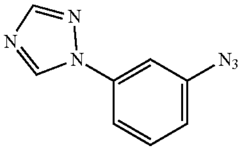 [SMILES: [N-]=[N+]=Nc1cccc(-n2cncn2)c1]
Plate 12 G3
-continued
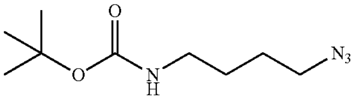
Plate 12 G4
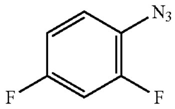
Plate 12 H1
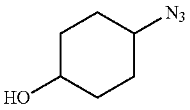
Plate 12 H2
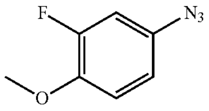
Plate 12 H3
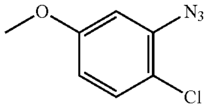
Plate 12 H4
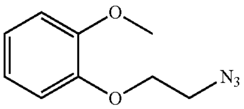
Plate 12 A5
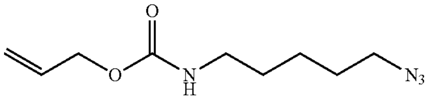
Plate 12 A6
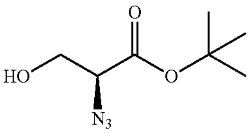
Plate 12 A7
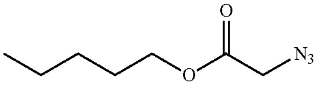
Plate 12 A8
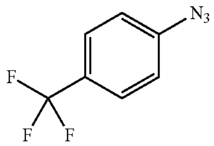 [SMILES: [N-]=[N+]=Nc1ccc(C(F)(F)F)cc1]
Plate 12 B5

-continued
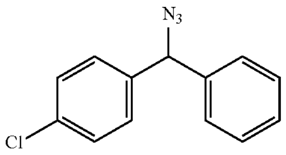 [SMILES: [N-]=[N+]=NC(c1ccccc1)c1ccc(Cl)cc1]
Plate 12 B6
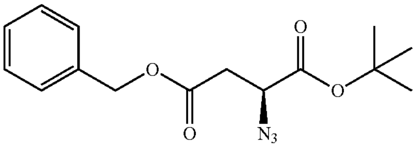 [SMILES: CC(C)(C)OC(=O)[C@H](CC(=O)OCc1ccccc1)N=[N+]=[N-]]
Plate 12 B7
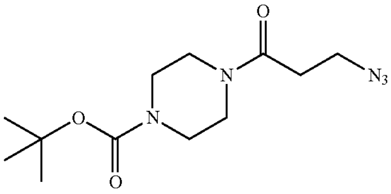 [SMILES: CC(C)(C)OC(=O)N1CCN(C(=O)CCN=[N+]=[N-])CC1]
Plate 12 B8
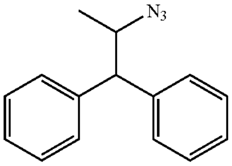 [SMILES: CC(N=[N+]=[N-])C(c1ccccc1)c1ccccc1]
Plate 12 C5
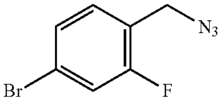 [SMILES: [N-]=[N+]=NCc1ccc(Br)cc1F]
Plate 12 C6
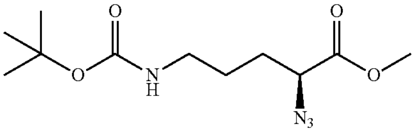 [SMILES: COC(=O)[C@H](CCCNC(=O)OC(C)(C)C)N=[N+]=[N-]]
Plate 12 C7
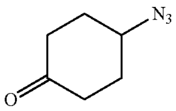
Plate 12 C8
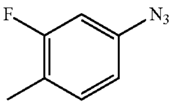
Plate 12 D5
-continued
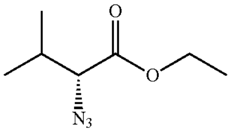
Plate 12 D6
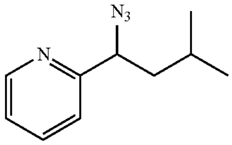
Plate 12 D7
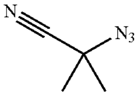
Plate 12 D8
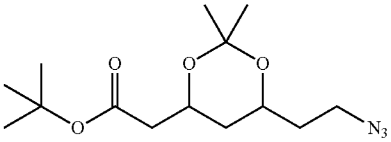 [SMILES: CC(C)(C)OC(=O)CC1CC(CCN=[N+]=[N-])OC(C)(C)O1]
Plate 12 E5
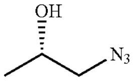
Plate 12 E6
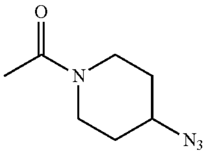
Plate 12 E7
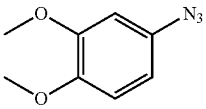
Plate 12 E8
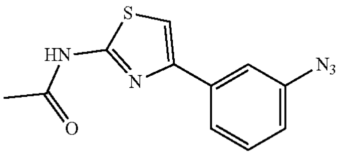 [SMILES: CC(=O)Nc1nc(-c2cccc(N=[N+]=[N-])c2)cs1]
Plate 12 F5
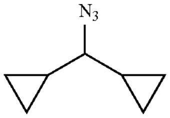
Plate 12 F6

-continued
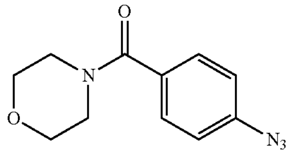 [SMILES: [N-]=[N+]=Nc1ccc(C(=O)N2CCOCC2)cc1]
Plate 12 F7
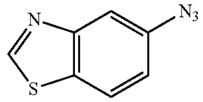 [SMILES: [N-]=[N+]=Nc1ccc2scnc2c1]
Plate 12 F8
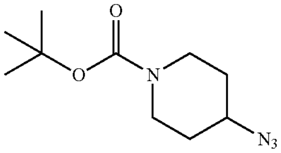 [SMILES: CC(C)(C)OC(=O)N1CCC(N=[N+]=[N-])CC1]
Plate 12 G5
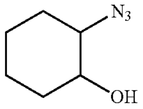
Plate 12 G6
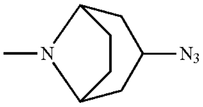
Plate 12 G7
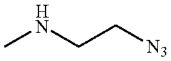
Plate 12 G8
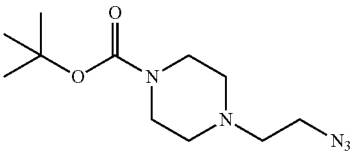 [SMILES: CC(C)(C)OC(=O)N1CCN(CCN=[N+]=[N-])CC1]
Plate 12 H5
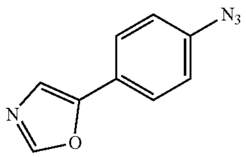 [SMILES: [N-]=[N+]=Nc1ccc(-c2cnco2)cc1]
Plate 12 H6
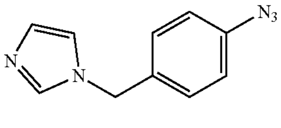 [SMILES: [N-]=[N+]=Nc1ccc(Cn2ccnc2)cc1]
Plate 12 H7
-continued
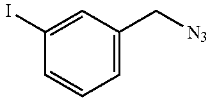 [SMILES: [N-]=[N+]=NCc1cccc(I)c1]
Plate 12 H8
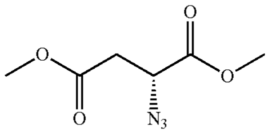
Plate 12 A9
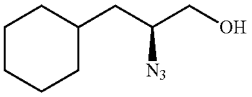 [SMILES: [N-]=[N+]=N[C@H](CO)CC1CCCCC1]
Plate 12 A10
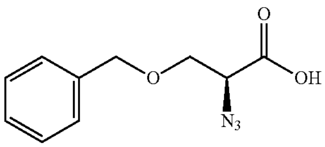 [SMILES: [N-]=[N+]=N[C@@H](COCc1ccccc1)C(=O)O]
Plate 12 A11
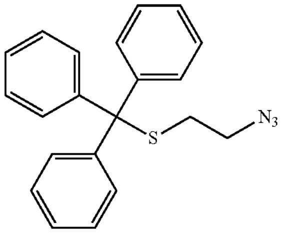 [SMILES: [N-]=[N+]=NCCSC(c1ccccc1)(c1ccccc1)c1ccccc1]
Plate 12 A12
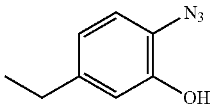
Plate 12 B9
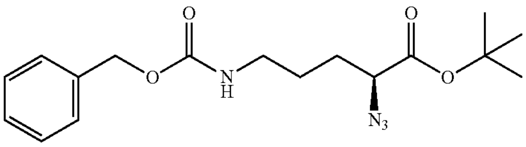 [SMILES: CC(C)(C)OC(=O)[C@H](CCCNC(=O)OCc1ccccc1)N=[N+]=[N-]]
Plate 12 B10
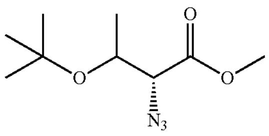
Plate 12 B11

-continued
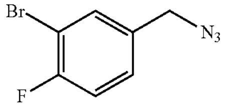
Plate 12 B12
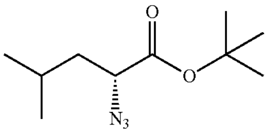
Plate 12 C9
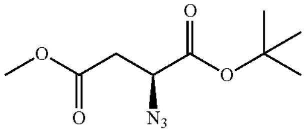 [SMILES: COC(=O)C[C@H](N=[N+]=[N-])C(=O)OC(C)(C)C]
Plate 12 C10
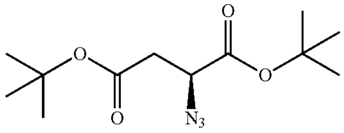 [SMILES: CC(C)(C)OC(=O)C[C@H](N=[N+]=[N-])C(=O)OC(C)(C)C]
Plate 12 C11
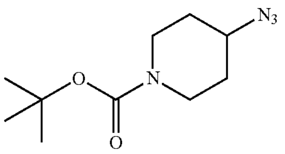 [SMILES: CC(C)(C)OC(=O)N1CCC(N=[N+]=[N-])CC1]
Plate 12 C12
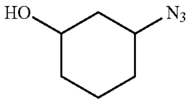
Plate 12 D9
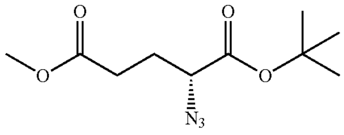 [SMILES: COC(=O)CC[C@@H](N=[N+]=[N-])C(=O)OC(C)(C)C]
Plate 12 D10
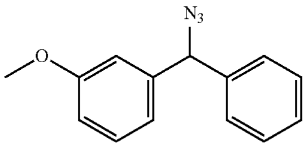 [SMILES: COc1cccc(C(N=[N+]=[N-])c2ccccc2)c1]
Plate 12 D11
-continued
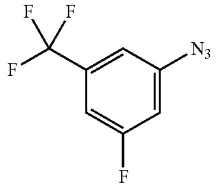 [SMILES: [N-]=[N+]=Nc1cc(F)cc(C(F)(F)F)c1]
Plate 12 D12
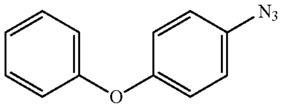 [SMILES: [N-]=[N+]=Nc1ccc(Oc2ccccc2)cc1]
Plate 12 E9
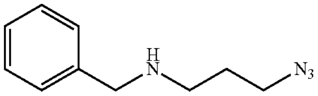 [SMILES: [N-]=[N+]=NCCCNCc1ccccc1]
Plate 12 E10
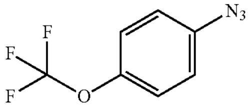 [SMILES: [N-]=[N+]=Nc1ccc(OC(F)(F)F)cc1]
Plate 12 E11
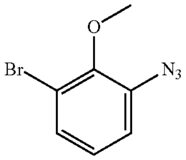
Plate 12 E12
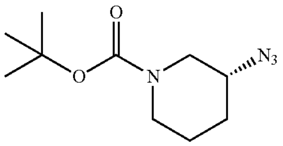 [SMILES: CC(C)(C)OC(=O)N1CCC[C@@H](N=[N+]=[N-])C1]
Plate 12 F9
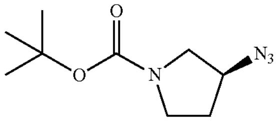
Plate 12 F10
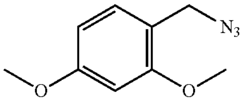
Plate 12 F11
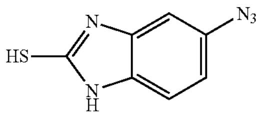 [SMILES: [N-]=[N+]=Nc1ccc2[nH]c(S)nc2c1]
Plate 12 F12

-continued
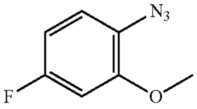
Plate 12 G9
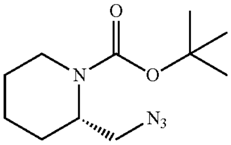 [SMILES: CC(C)(C)OC(=O)N1CCCC[C@H]1CN=[N+]=[N-]]
Plate 12 G10
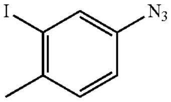
Plate 12 G11
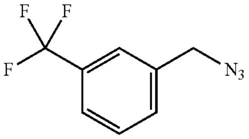 [SMILES: [N-]=[N+]=NCc1cccc(C(F)(F)F)c1]
Plate 12 G12
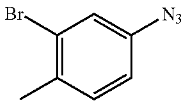
Plate 12 H9
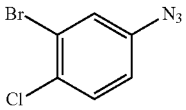 [SMILES: [N-]=[N+]=Nc1ccc(Cl)c(Br)c1]
Plate 12 H10
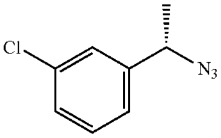
Plate 12 H11
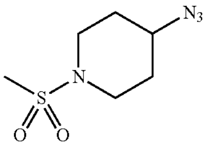
Plate 12 H12
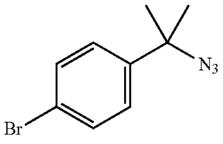
Plate 13 A1
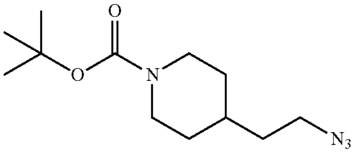
Plate 13 A2
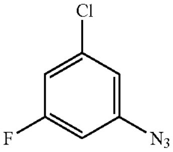
Plate 13 A3
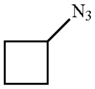
Plate 13 A4
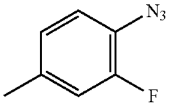
Plate 13 B1
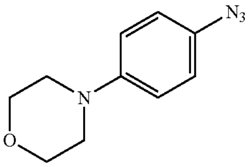
Plate 13 B2
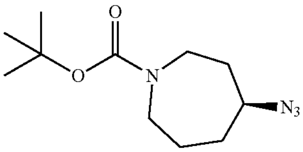
Plate 13 B3
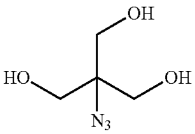
Plate 13 B4

-continued
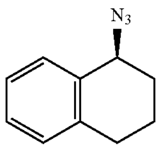
Plate 13 C1
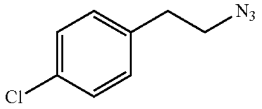
Plate 13 C2
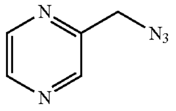
Plate 13 C3
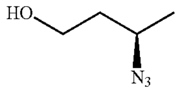
Plate 13 C4
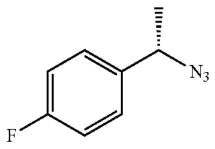
Plate 13 D1
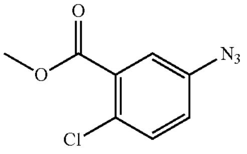
Plate 13 D2
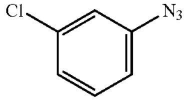
Plate 13 C3
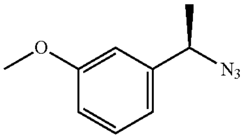
Plate 13 D4
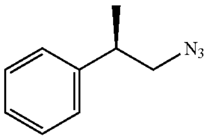
Plate 13 E1
-continued
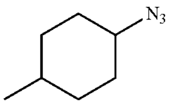
Plate 13 D2
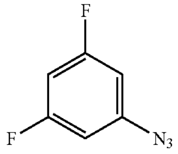
Plate 13 E3
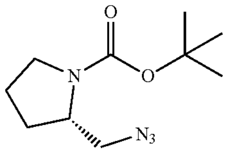 [SMILES: CC(C)(C)OC(=O)N1CCC[C@H]1CN=[N+]=[N-]]
Plate 13 E4
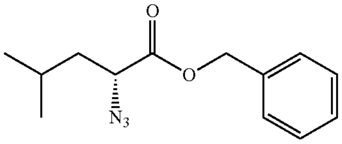 [SMILES: CC(C)C[C@@H](N=[N+]=[N-])C(=O)OCc1ccccc1]
Plate 13 F1
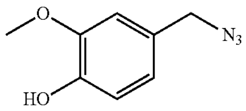
Plate 13 F2
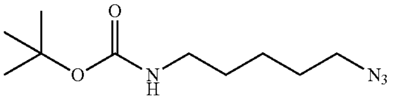 [SMILES: CC(C)(C)OC(=O)NCCCCCN=[N+]=[N-]]
Plate 13 F3
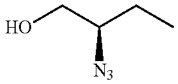
Plate 13 F4
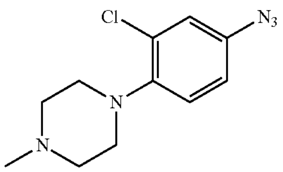 [SMILES: CN1CCN(c2ccc(N=[N+]=[N-])cc2Cl)CC1]
Plate 13 G1
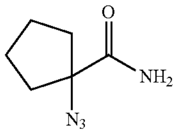
Plate 13 G2

-continued
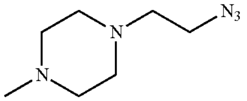
Plate 13 G3
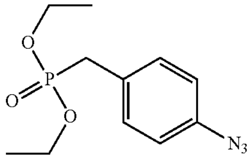 [SMILES: CCOP(=O)(Cc1ccc(N=[N+]=[N-])cc1)OCC]
Plate 13 G4
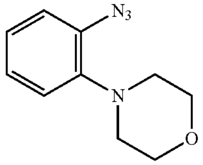 [SMILES: [N-]=[N+]=Nc1ccccc1N1CCOCC1]
Plate 13 H1
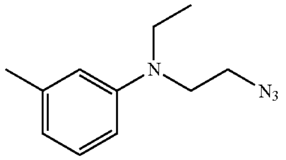
Plate 13 H2
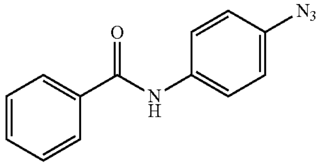 [SMILES: [N-]=[N+]=Nc1ccc(NC(=O)c2ccccc2)cc1]
Plate 13 H3
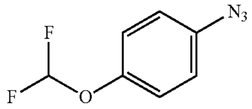 [SMILES: [N-]=[N+]=Nc1ccc(OC(F)F)cc1]
Plate 13 H4
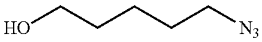
Plate 13 A5
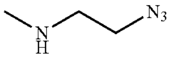
Plate 13 A6
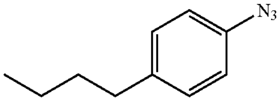
Plate 13 A7
-continued
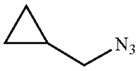
Plate 13 A8
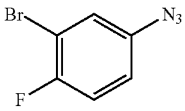
Plate 13 B5
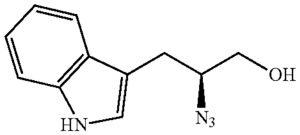
Plate 13 B6
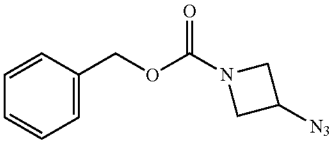
Plate 13 B7
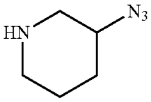
Plate 13 B8
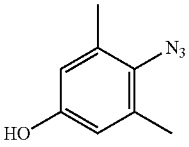
Plate 13 C5
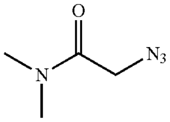
Plate 13 C6
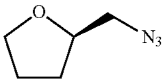
Plate 13 C7
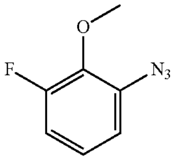
Plate 13 C8

-continued
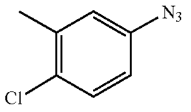
Plate 13 D5
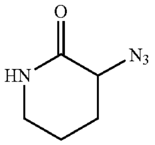
Plate 13 D6
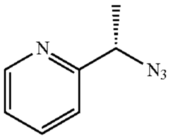
Plate 13 D7
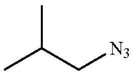
Plate 13 D8
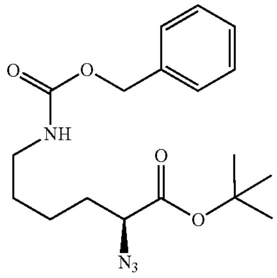 [SMILES: CC(C)(C)OC(=O)[C@H](CCCCNC(=O)OCc1ccccc1)N=[N+]=[N-]]
Plate 13 E5
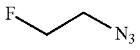
Plate 13 E6
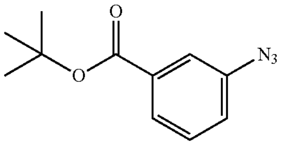 [SMILES: CC(C)(C)OC(=O)c1cccc(N=[N+]=[N-])c1]
Plate 13 E7
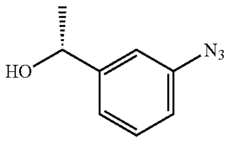
Plate 13 E8
-continued
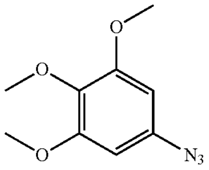
Plate 13 F5
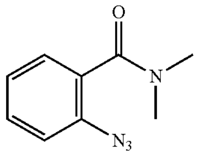
Plate 13 F6
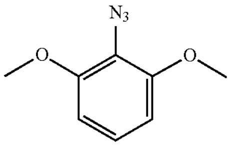
Plate 13 F7
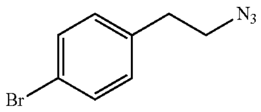 [SMILES: [N-]=[N+]=NCCc1ccc(Br)cc1]
Plate 13 F8
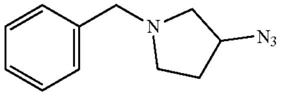 [SMILES: [N-]=[N+]=NC1CCN(Cc2ccccc2)C1]
Plate 13 G5
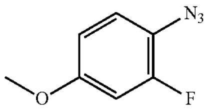
Plate 13 G6
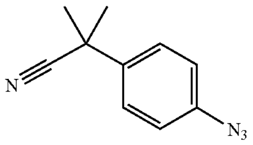
Plate 13 G7
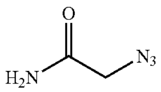
Plate 13 G8

-continued
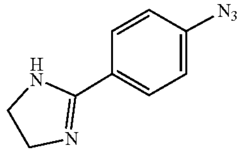 [SMILES: [N-]=[N+]=Nc1ccc(C2=NCCN2)cc1]
Plate 13 H5
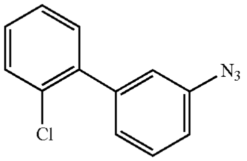 [SMILES: [N-]=[N+]=Nc1cccc(-c2ccccc2Cl)c1]
Plate 13 H6
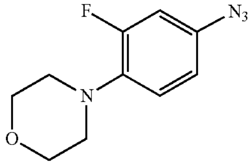 [SMILES: [N-]=[N+]=Nc1ccc(N2CCOCC2)c(F)c1]
Plate 13 H7
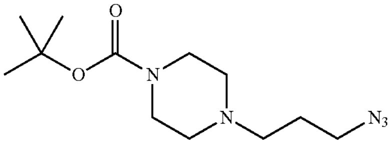 [SMILES: CC(C)(C)OC(=O)N1CCN(CCCN=[N+]=[N-])CC1]
Plate 13 H8
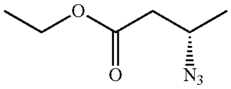
Plate 13 A9
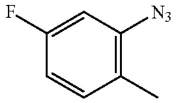
Plate 13 A10
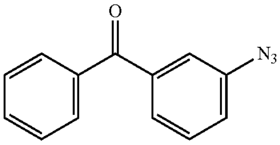 [SMILES: [N-]=[N+]=Nc1cccc(C(=O)c2ccccc2)c1]
Plate 13 A11
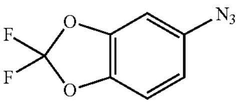 [SMILES: [N-]=[N+]=Nc1ccc2c(c1)OC(F)(F)O2]
Plate 13 A12
-continued
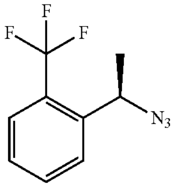
Plate 13 B9
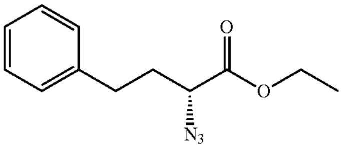 [SMILES: CCOC(=O)[C@@H](CCc1ccccc1)N=[N+]=[N-]]
Plate 13 B10
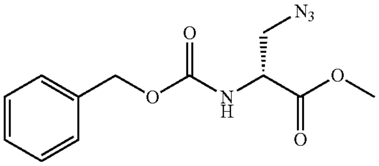 [SMILES: COC(=O)[C@@H](CN=[N+]=[N-])NC(=O)OCc1ccccc1]
Plate 13 B11
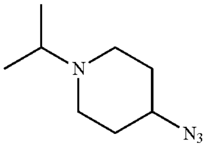
Plate 13 B12
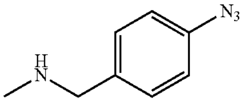
Plate 13 C9
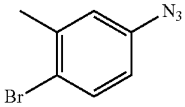
Plate 13 C10
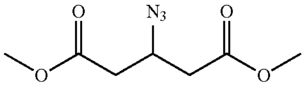
Plate 13 C11
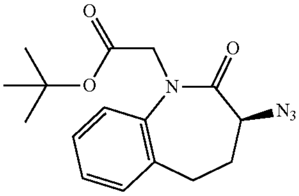 [SMILES: CC(C)(C)OC(=O)CN1C(=O)[C@@H](N=[N+]=[N-])CCc2ccccc21]
Plate 13 C12

-continued
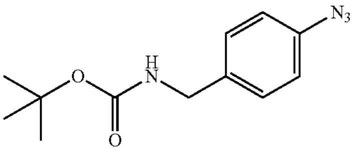 [SMILES: CC(C)(C)OC(=O)NCc1ccc(N=[N+]=[N-])cc1]
Plate 13 D9
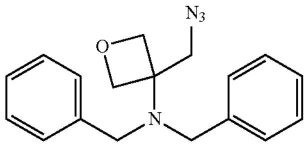 [SMILES: [N-]=[N+]=NCC1(N(Cc2ccccc2)Cc2ccccc2)COC1]
Plate 13 D10
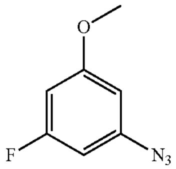
Plate 13 D11
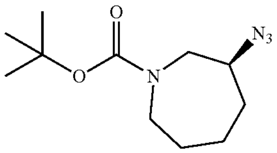
Plate 13 D12
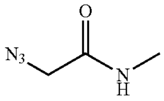
Plate 13 E9
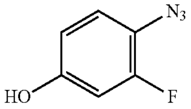
Plate 13 E10
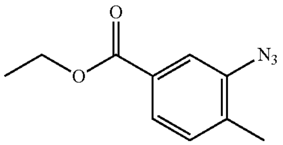
Plate 13 E11
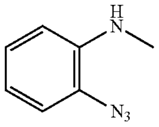
Plate 13 E12
-continued
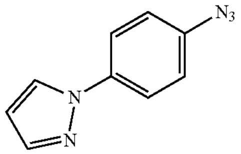
Plate 13 F9
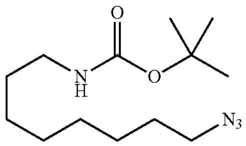
Plate 13 F10
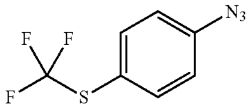
Plate 13 F11
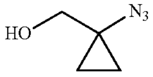
Plate 13 F12
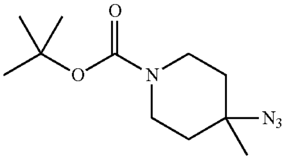
Plate 13 G9
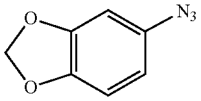
Plate 13 G10
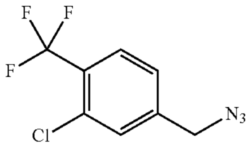
Plate 13 G11
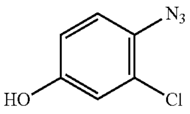
Plate 13 G12

-continued
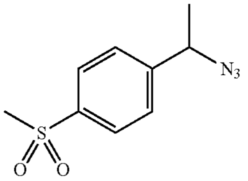
Plate 13 H9
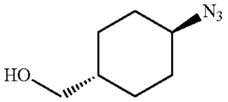 [SMILES: [N-]=[N+]=N[C@H]1CC[C@H](CO)CC1]
Plate 13 H10
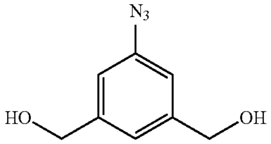 [SMILES: [N-]=[N+]=Nc1cc(CO)cc(CO)c1]
Plate 13 H11
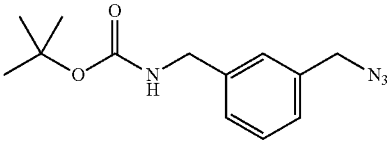 [SMILES: CC(C)(C)OC(=O)NCc1cccc(CN=[N+]=[N-])c1]
Plate 13 H12
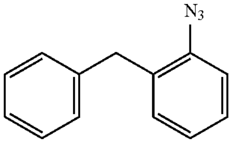 [SMILES: [N-]=[N+]=Nc1ccccc1Cc1ccccc1]
Plate 14 A1
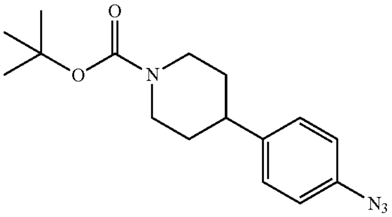 [SMILES: CC(C)(C)OC(=O)N1CCC(c2ccc(N=[N+]=[N-])cc2)CC1]
Plate 14 A2
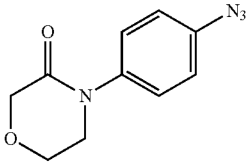 [SMILES: [N-]=[N+]=Nc1ccc(N2CCOCC2=O)cc1]
Plate 14 A3
-continued
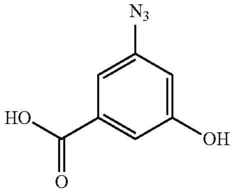
Plate 14 A4
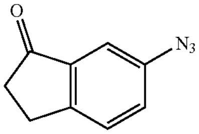 [SMILES: [N-]=[N+]=Nc1ccc2c(c1)C(=O)CC2]
Plate 14 B1
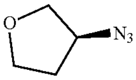
Plate 14 B2
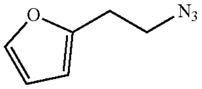
Plate 14 B3
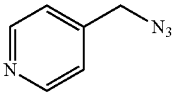
Plate 14 B4
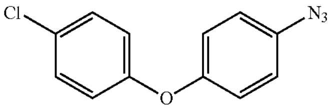 [SMILES: [N-]=[N+]=Nc1ccc(Oc2ccc(Cl)cc2)cc1]
Plate 14 C1
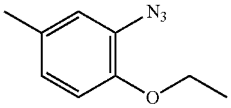
Plate 14 C2
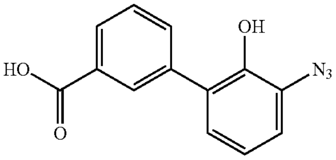 [SMILES: [N-]=[N+]=Nc1cccc(-c2cccc(C(=O)O)c2)c1O]
Plate 14 C3
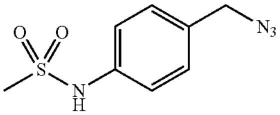
Plate 14 C4

-continued
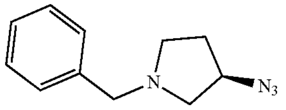 [SMILES: [N-]=[N+]=N[C@@H]1CCN(Cc2ccccc2)C1]
Plate 14 D1
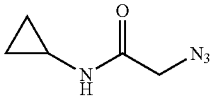
Plate 14 D2
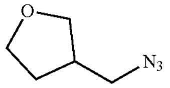
Plate 14 D3
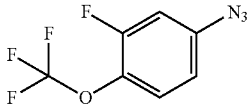 [SMILES: [N-]=[N+]=Nc1ccc(OC(F)(F)F)c(F)c1]
Plate 14 D4
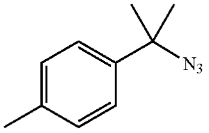
Plate 14 E1
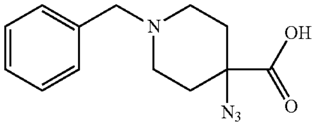 [SMILES: [N-]=[N+]=NC1(C(=O)O)CCN(Cc2ccccc2)CC1]
Plate 14 E2
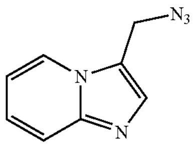 [SMILES: [N-]=[N+]=NCc1cnc2ccccn12]
Plate 14 E3
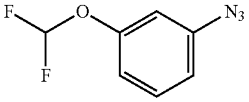 [SMILES: [N-]=[N+]=Nc1cccc(OC(F)F)c1]
Plate 14 E4
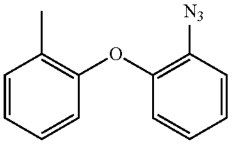 [SMILES: Cc1ccccc1Oc1ccccc1N=[N+]=[N-]]
Plate 14 F1
-continued
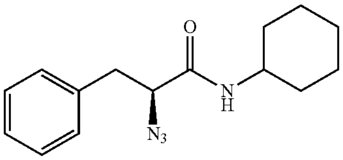 [SMILES: [N-]=[N+]=N[C@@H](Cc1ccccc1)C(=O)NC1CCCCC1]
Plate 14 F2
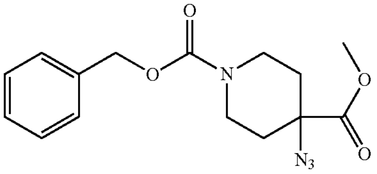 [SMILES: COC(=O)C1(N=[N+]=[N-])CCN(C(=O)OCc2ccccc2)CC1]
Plate 14 F3
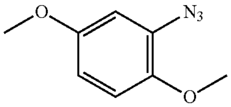
Plate 14 F4
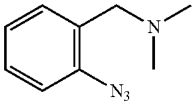
Plate 14 A5
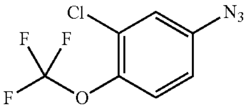 [SMILES: [N-]=[N+]=Nc1ccc(OC(F)(F)F)c(Cl)c1]
Plate 14 A6
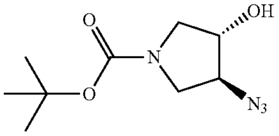 [SMILES: CC(C)(C)OC(=O)N1C[C@H](N=[N+]=[N-])[C@@H](O)C1]
Plate 14 A7
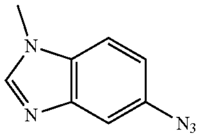
Plate 14 A8
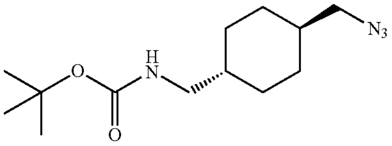 [SMILES: CC(C)(C)OC(=O)NC[C@H]1CC[C@H](CN=[N+]=[N-])CC1]
Plate 14 B5

-continued
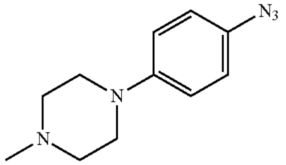 [SMILES: CN1CCN(c2ccc(N=[N+]=[N-])cc2)CC1]
Plate 14 B6
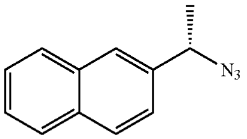
Plate 14 B7
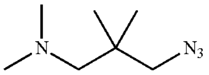
Plate 14 B8
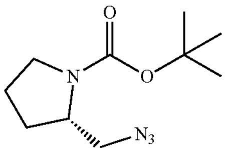 [SMILES: CC(C)(C)OC(=O)N1CCC[C@H]1CN=[N+]=[N-]]
Plate 14 C5
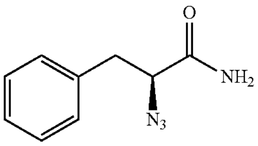 [SMILES: [N-]=[N+]=N[C@@H](Cc1ccccc1)C(N)=O]
Plate 14 C6
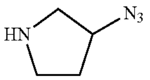
Plate 14 C7
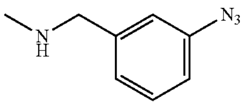
Plate 14 C8
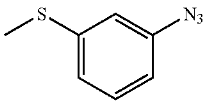
Plate 14 D5
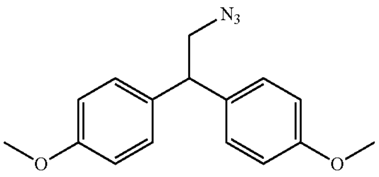
Plate 14 D6
-continued
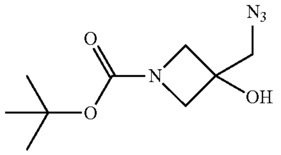 [SMILES: CC(C)(C)OC(=O)N1CC(O)(CN=[N+]=[N-])C1]
Plate 14 D7
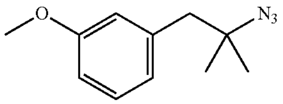
Plate 14 D8
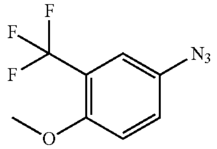
Plate 14 E5
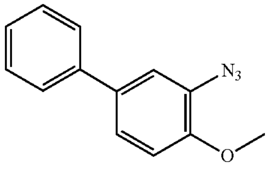 [SMILES: COc1ccc(-c2ccccc2)cc1N=[N+]=[N-]]
Plate 14 E6
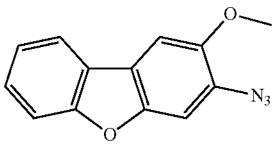 [SMILES: COc1cc2c(cc1N=[N+]=[N-])oc1ccccc12]
Plate 14 E7
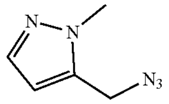
Plate 14 E8
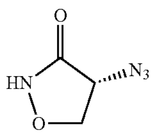
Plate 14 F5
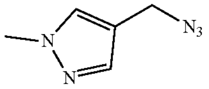
Plate 14 F6

-continued
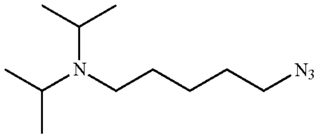
Plate 14 F7
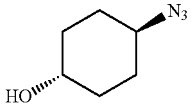
Plate 14 F8
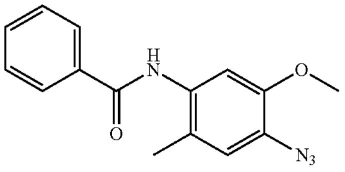 [SMILES: COc1cc(NC(=O)c2ccccc2)c(C)cc1N=[N+]=[N-]]
Plate 14 A9
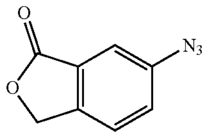 [SMILES: [N-]=[N+]=Nc1ccc2c(c1)C(=O)OC2]
Plate 14 A10
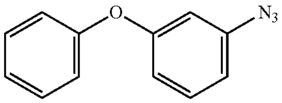 [SMILES: [N-]=[N+]=Nc1cccc(Oc2ccccc2)c1]
Plate 14 A11
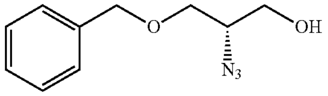 [SMILES: [N-]=[N+]=N[C@@H](CO)COCc1ccccc1]
Plate 14 A12
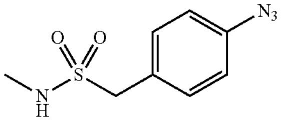
Plate 14 B9
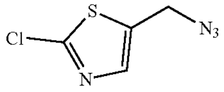
Plate 14 B10
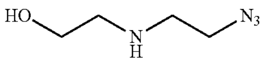
Plate 14 B11
-continued
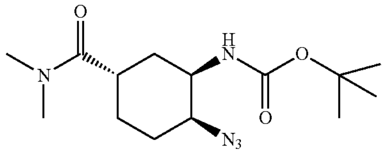 [SMILES: CN(C)C(=O)[C@H]1CC[C@H](N=[N+]=[N-])[C@H](NC(=O)OC(C)(C)C)C1]
Plate 14 B12
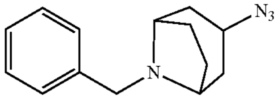 [SMILES: [N-]=[N+]=NC1CC2CCC(C1)N2Cc1ccccc1]
Plate 14 C9
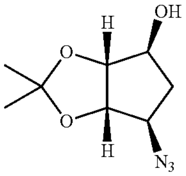
Plate 14 C10
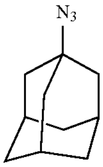 [SMILES: [N-]=[N+]=NC12CC3CC(CC(C3)C1)C2]
Plate 14 C11
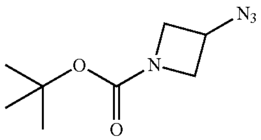
Plate 14 C12
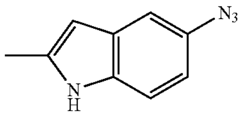
Plate 14 D9
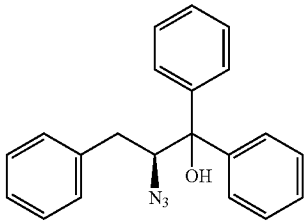 [SMILES: [N-]=[N+]=N[C@@H](Cc1ccccc1)C(O)(c1ccccc1)c1ccccc1]
Plate 14 D10
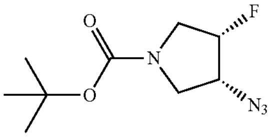 [SMILES: CC(C)(C)OC(=O)N1C[C@H](F)[C@H](N=[N+]=[N-])C1]
Plate 14 D11

-continued

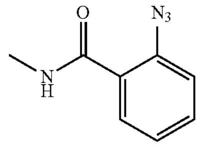

Plate 14 D12

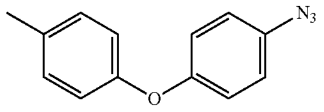 [SMILES: Cc1ccc(Oc2ccc(N=[N+]=[N-])cc2)cc1]

Plate 14 E9

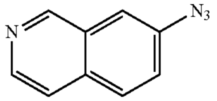 [SMILES: [N-]=[N+]=Nc1ccc2ccncc2c1]

Plate 14 E10

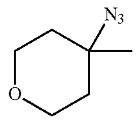

Plate 14 E11

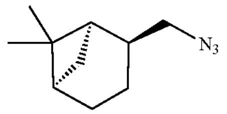

Plate 14 E12

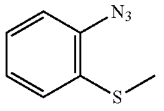

Plate 14 F9

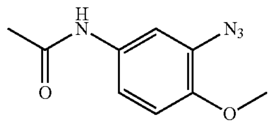

Plate 14 F10

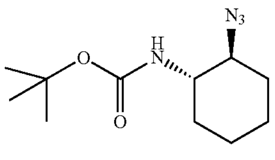 [SMILES: CC(C)(C)OC(=O)N[C@H]1CCCC[C@@H]1N=[N+]=[N-]]

Plate 14 F11

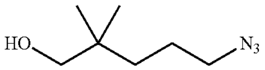

Plate 14 F12

Example 5 1, 2, 3-Triazole Compound Library was Obtained Directly by Diazotransfer and Copper-Catalyzed Azide Terminal Acetylene Cycloaddition Reaction (CuAAC) Using the Primary Amine Compound Library

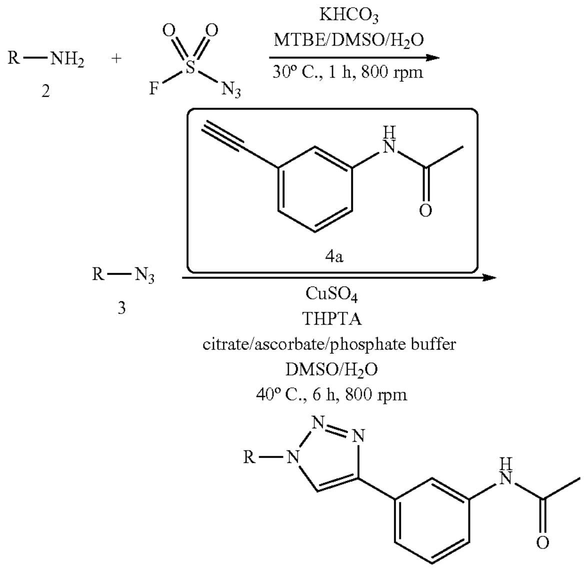

5a

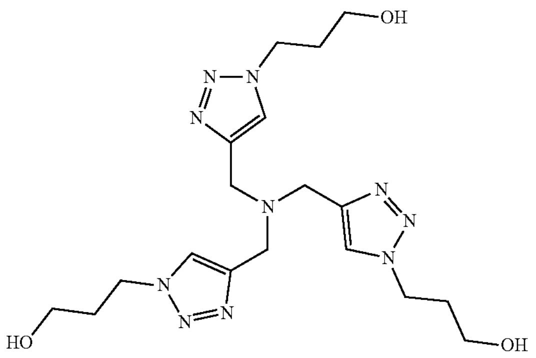

THPTA

50 μl (100 mM, dimethyl sulfoxide as solvent, containing 5 μmol of primary amine) was taken from per well in each 96-well plate of the 1128 primary amine compound library prepared in EXAMPLE 2 (i.e. the primary amin compound structures corresponding to the azide compounds in plates 1-7 and 10-14 in EXAMPLE 2) and transferred to the corresponding locations in a new 96-well plate. Subsequently, in these new plates containing primary amine solution, an aqueous potassium bicarbonate solution (3.0 M, 6.7 μl, containing 20 μmol of potassium bicarbonate), a fluorosulfonyl azide solution (refer to EXAMPLE 1, diluted in a solvent system of dimethyl sulfoxide/methyl tert-butyl ether 1:1; 200 mM, 25 μl, containing 5 gmol of fluorosulfonyl azide) and dimethyl sulfoxide (18 μl) were successively added to each well making a total volume to about 100 μl. The 96-well plate was sealed and shaken for 1 hour at 800 rpm under 30° C.

Sodium ascorbate (2.48 g, 12.5 mmol), disodium hydrogen phosphate (7.0 g, 49.3 mmol) and citric acid (4.87 g, 25.4 mmol) were mixed and dissolved in distilled water to 100 ml aqueous solution to obtain a buffer solution of sodium ascorbate/disodium hydrogen phosphate/citric acid with a pH value of about 5.

After shaking for 1 hour, the sealing film was removed from the 96-well plate, and the above prepared buffer solution of sodium ascorbate/disodium hydrogen phosphate/citric acid (40 g 1) was added, and after film sealing shaken at 800 rpm for 15 minutes at 30° C. Tearing off the sealing film, 3-acetamidophenylacetylene solution (compound 4a, 100 mM, the solvent was dimethyl sulfoxide; 47.5 µl, containing 4.75 µmol of 3-acetaminophenylacetylene) and copper sulfate/THPTA aqueous solution (the concentrations of both copper sulfate and THPTA were 20 mM respectively, 12.5 µl, 0.25 µmol) were added to each well. The microplate was sealed again and shaken for 6 hour at 800 rpm under 40° C. After the reaction was completed, the in-plate mixture was transferred one-to-one to an empty 1.2 ml 96-well plate, diluted by adding methanol (400 µl) and acetonitrile (400 µl) to each well, and the resulting 1, 2, 3-triazole product was detected by UPLC-MS.

Exemplary UPLC chromatographic detection results were shown in FIGS. 4*a-i*.

Example 6 1, 2, 3-Triazole Compound Library was Obtained Directly by Diazotransfer and Copper-Catalyzed Azide Terminal Acetylene Cycloaddition Reaction (CnuAAC) Using the Primary Amine Compound Library

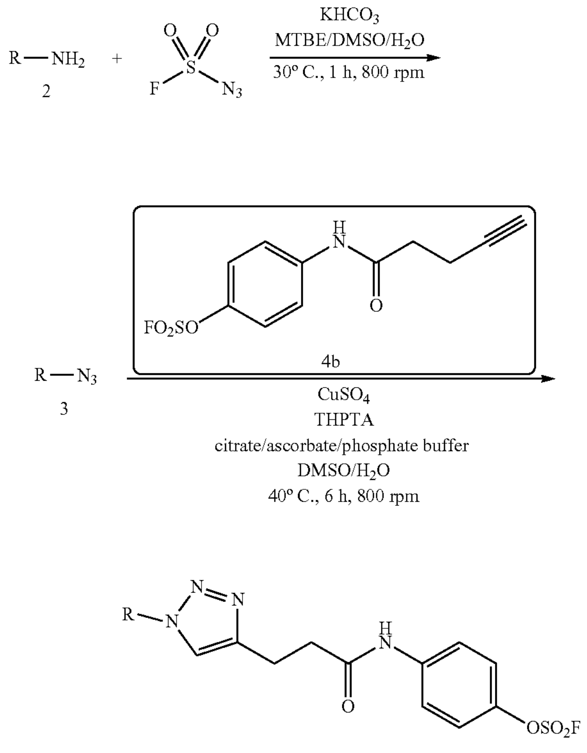

2

3

4b

5b

-continued

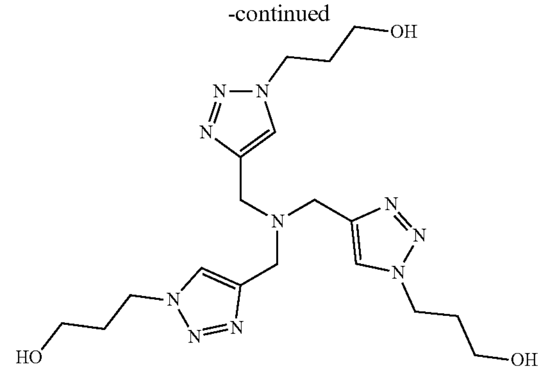

THPTA

50 µl (100 mM, dimethyl sulfoxide, containing 5 µmol of primary amine) was taken from each well in the second plate of the 1128 primary amine compound library prepared in EXAMPLE 2 (i.e. the primary amine compound structures corresponding to the azide compounds in plates 1-7 and 10-14 in EXAMPLE 2) and transferred to the corresponding locations in a new 96-well plate. Subsequently, in these new plates containing primary amine solution, an aqueous potassium bicarbonate solution (3.0 M, 6.7 µl, containing 20 µmol of potassium bicarbonate), a fluorosulfonyl azide solution (refer to EXAMPLE 1, diluted in a solvent system of dimethyl sulfoxide/methyl tert-butyl ether 1:1; 200 mM, 25 µl, containing 5 gmol of fluorosulfonyl azide) and dimethyl sulfoxide (18 µl) were successively added to each well making a total volume to about 100 µl. The 96-well plate was sealed and shaken for 1 hour at 00 rpm under 30° C.

Sodium ascorbate (2.48 g, 12.5 mmol), disodium hydrogen phosphate (7.0 g, 49.3 mmol) and citric acid (4.87 g, 25.4 mmol) were mixed and dissolved in distilled water to 100 ml aqueous solution to obtain a buffer solution of sodium ascorbate/disodium hydrogen phosphate/citric acid with a pH value of about 5.

After shaking for 1 hour, the sealing film was removed from the 96-well plate, and the above prepared buffer solution of sodium ascorbate/disodium hydrogen phosphate/citric acid (40 µl) was added and after film sealing, shaken at 800 rpm for 15 minutes at 30° C. Tearing off the sealing film and 4-(4-pentynylamido)phenyl fluorosulfonate solution (compound 4b, 100 mM, the solvent as dimethyl sulfoxide; 47.5 µl, containing 4.75 µmol of 3-acetaminophenylacetylene) and copper sulfate/THPTA aqueous solution (the concentrations of both cop er sulfate and THPTA were 20 mM respectively, 12.5 µl, 0.25 µmol) were added to each well. The microplate was sealed again and shaken for 6 hour at 800 rpm under 40° C. After the reaction was completed, the in-plate mixture was transferred one-to-one to a empty 96-well plate with a size of 1.2 ml, diluted by adding methanol (400 µl) and acetonitrile (400 1) to each well, and the resulting 1, 2, 3-triazole product was detected by UPLC-MS.

Exemplary UPLC chromatographic detection results were shown in FIGS. 5*a-d*.

The corresponding compounds of the azide compound library and triazole compound library prepared in EXAMPLEs 1-6 were analyzed, and the results were summarized as follows (FIG. 1):

(a) Searched in the Reaxys database, 618 azides are currently known and 606 azides are new.

(b) Among 1224 addressable reactions, 656 products (about 54%) have a conversion of more than 90%; 333 products (about 27%) have a conversion rate of 70-90%; 144 products have a conversion rate of 30-70%; 17 products have a conversion rate of <30%; 74 products have UPLC detection peaks superimposed with the peaks of 3-acetamide-phenylacetylene, so the conversion rate could not be calculated.

The above results showed that almost all the addressable reactions yielded corresponding expected products, and at least 989 (989/1224=80.8%) addressable reactions achieved a conversion rates of more than 70%, thus fully meeting the requirements of subsequent bioactivity tests.

The identification results of some of the compounds formed in 1224 addressable reactions carried out in the reaction chamber were shown in FIGS. 3, 4 and 5.

In conclusion, unexpectedly, by the method of the present invention, specific synthetic reaction are independently carried out in each reaction chamber, thus a large number of different reaction products with well-defined structures could be prepared efficiently and in high throughput and thus obtaining a high throughput compound library. Therefore, subsequent compound activity determination in situ can be directly carried out in the addressable reaction chamber array (or corresponding compound library) containing the reaction product without separation and purification.

Example 7 Construction of a Library Containing 840 Erlotinib Derivatives

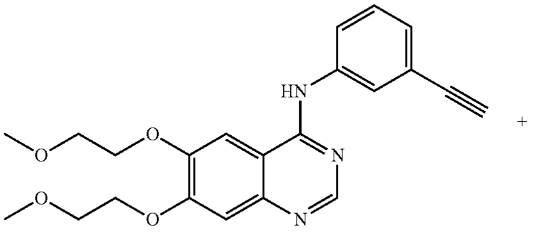

Ertotinib

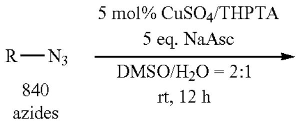

840 azides

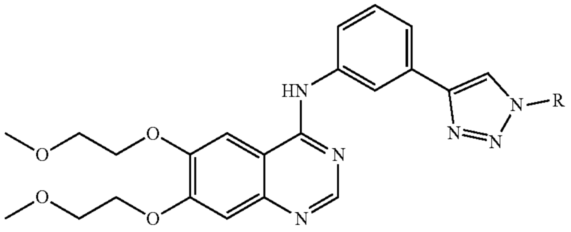

840 Ertotinib derivitives

-continued

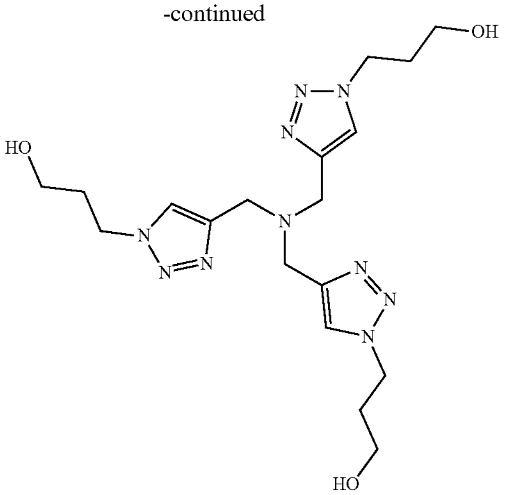

THPTA

The general reaction formula was shown above, and the operation steps were as follows:

(1) 37 μL DMSO, 13 μL $H_2O$, 10 μL DMSO of azide module solution (50 mM) and 20 μL solution of Erlotinib in DMSO (25 mM) were added into each well in 96-well plates, and mixed uniformly.

(2) 5 μL aqueous copper sulfate solution (5 mM), 5 μL aqueous tris [(1-(3-hydroxypropyl)-1H-1, 2, 3-triazol-4-yl)]methyl]amine solution (5 mM) and 10 μL aqueous sodium ascorbate solution (250 mM) were added to each well in a 96-well plate, and reacted for 12 hours in a shaking table at room temperature.

There were 9 96-well plates with 840 samples (final concentration: 5 mM, final volume: 100 μL) in total. UPLC-MS random tracking of some samples showed that most samples have a conversion rate of was over 70%, and were directly used for MTT screening.

Screening 840 Erlotinib derivatives by MTT method, operating steps:

(1) A549 (lung cancer) cells were adhered overnight: the logarithmic growth phase cells were digested and then counted, and were laid on 96 well plates overnight with 5000 cells per well.

(2) Adding drug: the compound concentration was diluted to 10 μM with complete culture solution, and the supernatant was discarded, and a volume of 100 μL per well was administrated and treated for 24 hours.

(3) Adding MTT: 20 μL MTT (5 mg/ml) was added to each well and cultured for 4 hours.

(4) Measuring the absorbance value: discarding the supernatant, 150 μL DMSO was added to each well, shaken for 10 minutes to make the crystals fully dissolved. The absorbance at 570 nm was measured by microplate reader.

The relative survival rate was calculated as the ratio of the survival rate of cells treated with Erlotinib derivatives to the survival rate of cells treated with positive compounds (Erlotinib), where lower relative survival rate means the activity of the compounds are better.

EXPERIMENTAL RESULTS

Figure 6:
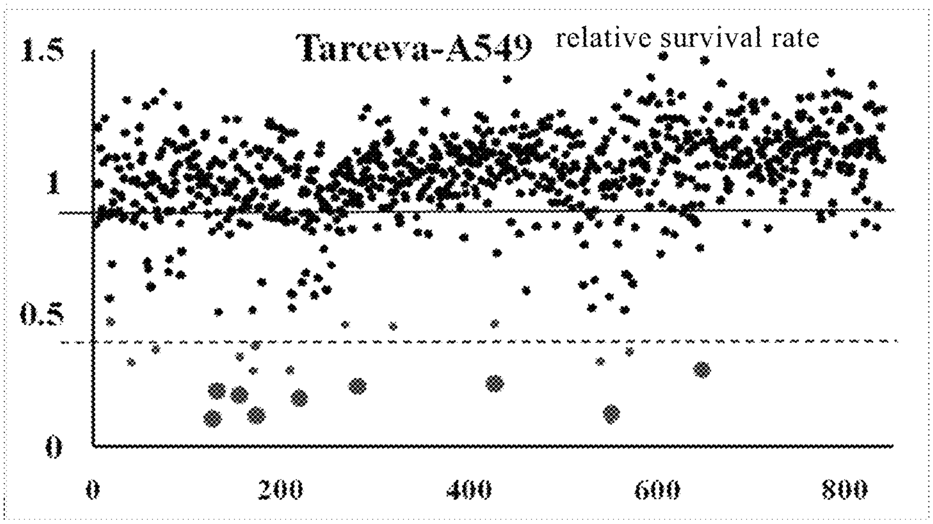
FIG. 6 shows that in an example of the present inventio, a compound library containing 840 compounds for a drug molecule was constructed by high throughput, and the activity was screened.

The results were shown in FIG. 6: among the 840 compounds, total 265 compounds with higher activity than Erlotinib (relative survival rate <1) were preliminarily screened on A549 cells, and 19 compounds with better activity (relative survival rate <0.5).

Compounds selected from a plurality of 96-well array reactors with exemplary partial activity better or slightly better than positive compounds (Erlotinib) for each addressable reaction chamber were listed in Tables 1 and 2 below:

TABLE 1

Structure and biological activity of some compounds in high-throughput compound library (relative survival rate = 0.5 ~ 1)

| Serial number of compound | Address in compound library | Relative survival rate | Compound structure | Molecular weight |
|---|---|---|---|---|
| 20 | P11-A4 | 0.993 | 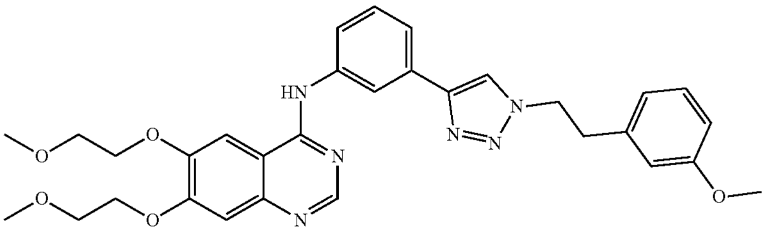 | 570.26 |
| 21 | P11-A6 | 0.995 | 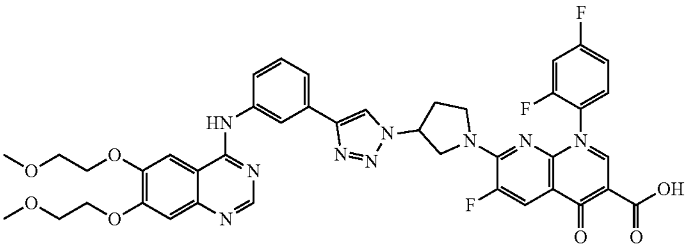 | 823.27 |
| 22 | P11-A7 | 0.866 | 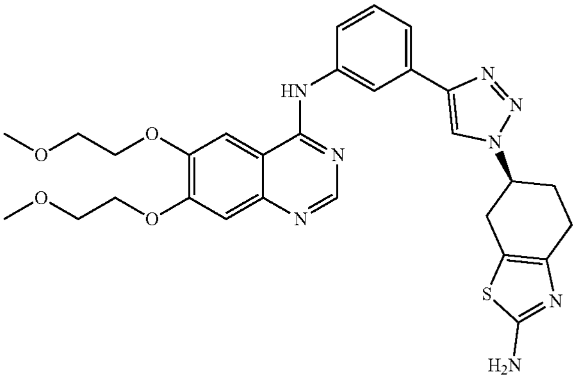 [SMILES: COCCOc1cc2ncnc(Nc3cccc(-c4cn([C@H]5CCc6nc(N)sc6C5)nn4)c3)c2cc1OCCOC] | 588.23 |
| 23 | P11-B4 | 0.874 | 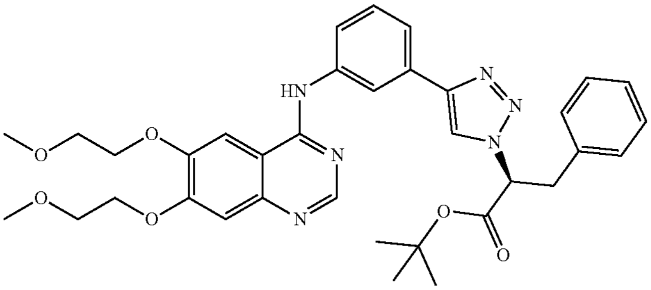 [SMILES: COCCOc1cc2ncnc(Nc3cccc(-c4cn([C@@H](Cc5ccccc5)C(=O)OC(C)(C)C)nn4)c3)c2cc1OCCOC] | 640.30 |

TABLE 1-continued
Structure and biological activity of some compounds in high-throughput compound library (relative survival rate = 0.5 ~ 1)
| Serial number of compound | Address in compound library | Relative survival rate | Compound structure | Molecular weight |
|---|---|---|---|---|
| 24 | P11-B5 | 0.557 | 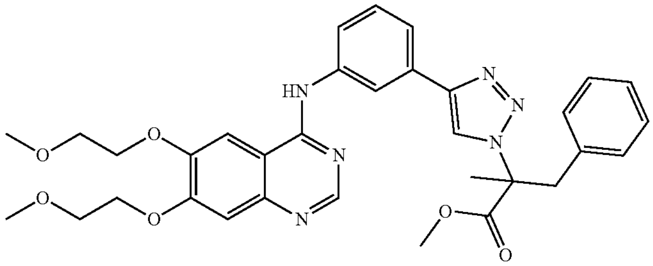 [SMILES: COCCOc1cc2ncnc(Nc3cccc(-c4cn(C(C)(Cc5ccccc5)C(=O)OC)nn4)c3)c2cc1OCCOC] | 612.27 |
| 25 | P11-B7 | 0.885 | 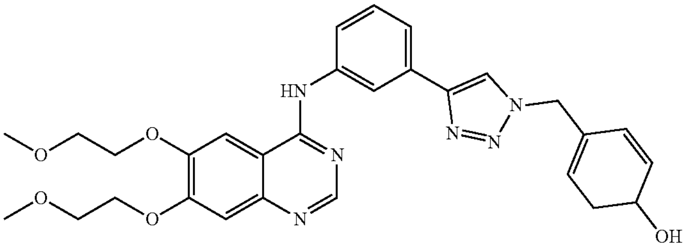 [SMILES: COCCOc1cc2ncnc(Nc3cccc(-c4cn(CC5=CCC(O)C=C5)nn4)c3)c2cc1OCCOC] | 542.23 |
| 26 | P11-C6 | 0.942 | 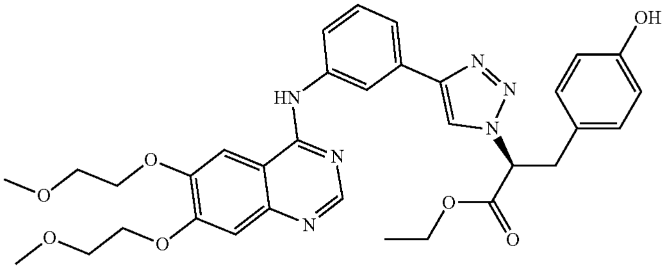 [SMILES: CCOC(=O)[C@H](Cc1ccc(O)cc1)n1cc(-c2cccc(Nc3ncnc4cc(OCCOC)c(OCCOC)cc34)c2)nn1] | 628.26 |
| 27 | P11-C7 | 0.862 | 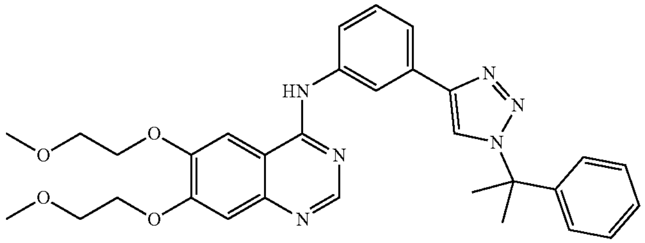 [SMILES: COCCOc1cc2ncnc(Nc3cccc(-c4cn(C(C)(C)c5ccccc5)nn4)c3)c2cc1OCCOC] | 554.26 |
| 47 | P12-A1 | 0.893 | 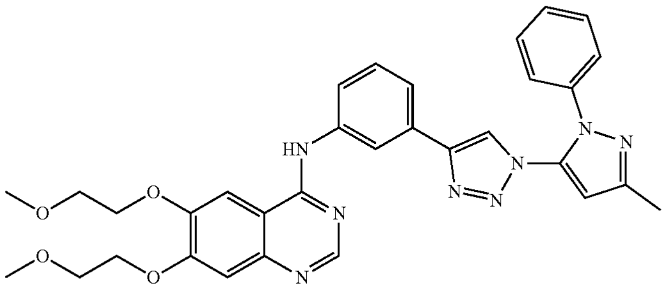 | 592.25 |

TABLE 1-continued
Structure and biological activity of some compounds in high-throughput compound library (relative survival rate = 0.5 ~ 1)
| Serial number of compound | Address in compound library | Relative survival rate | Compound structure | Molecular weight |
|---|---|---|---|---|
| 48 | P12-A7 | 0.971 | 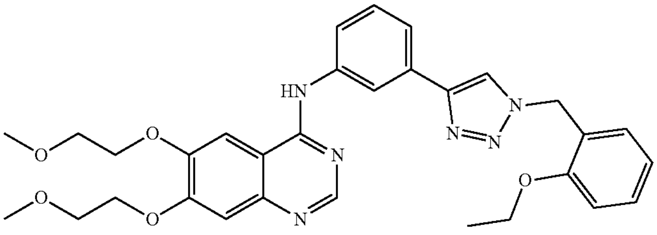 [SMILES: CCOc1ccccc1Cn1cc(-c2cccc(Nc3ncnc4cc(OCCOC)c(OCCOC)cc34)c2)nn1] | 570.26 |
| 49 | P12-A9 | 0.913 | 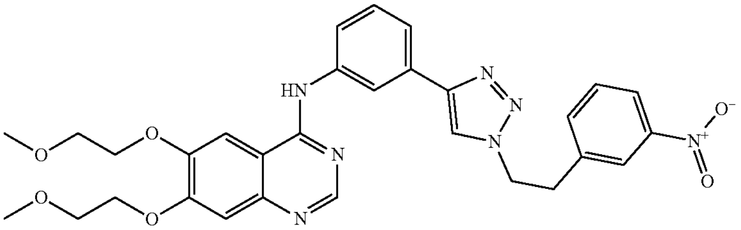 [SMILES: COCCOc1cc2ncnc(Nc3cccc(-c4cn(CCc5cccc([N+](=O)[O-])c5)nn4)c3)c2cc1OCCOC] | 585.23 |
| 50 | P12-B4 | 0.951 | 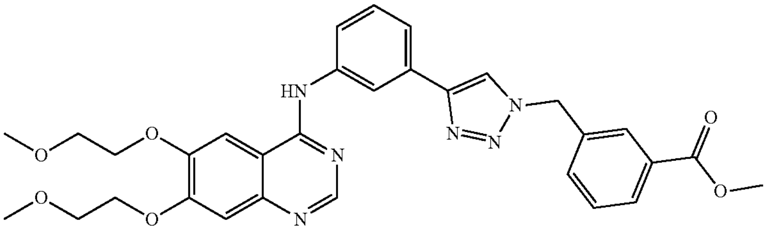 | 584.24 |
| 51 | P12-B5 | 0.989 | 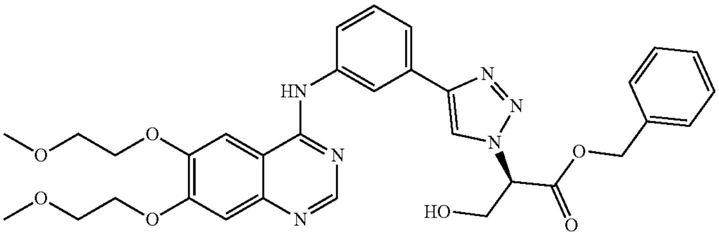 [SMILES: COCCOc1cc2ncnc(Nc3cccc(-c4cn([C@H](CO)C(=O)OCc5ccccc5)nn4)c3)c2cc1OCCOC] | 614.24 |
| 52 | P12-B12 | 0.993 | 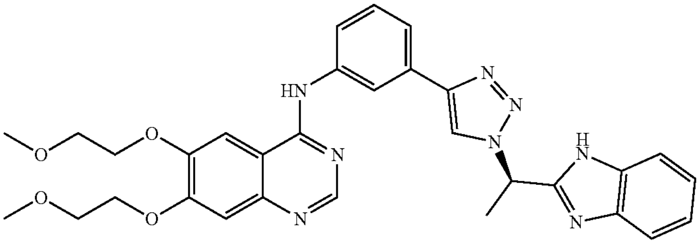 [SMILES: COCCOc1cc2ncnc(Nc3cccc(-c4cn([C@H](C)c5nc6ccccc6[nH]5)nn4)c3)c2cc1OCCOC] | 580.25 |
| 53 | P12-C1 | 0.928 | 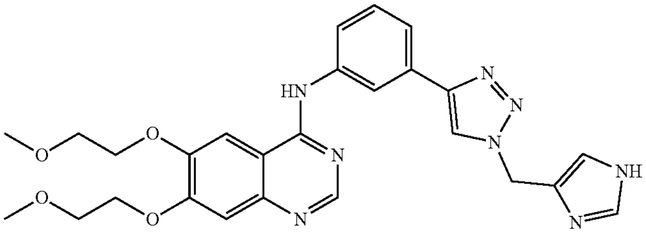 [SMILES: COCCOc1cc2ncnc(Nc3cccc(-c4cn(Cc5c[nH]cn5)nn4)c3)c2cc1OCCOC] | 516.22 |

TABLE 1-continued
| Serial number of compound | Address in compound library | Relative survival rate | Compound structure | Molecular weight |
|---|---|---|---|---|
| Structure and biological activity of some compounds in high-throughput compound library (relative survival rate = 0.5 ~ 1) | | | | |
| 54 | P12-C2 | 0.878 | 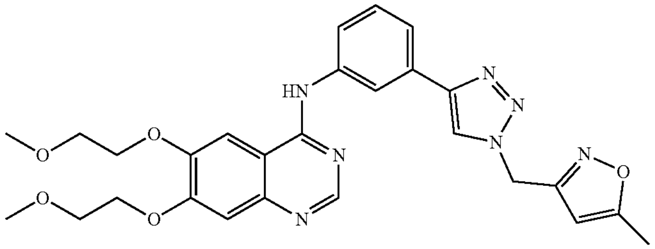 | 531.22 |
| 55 | P12-C6 | 0.814 | 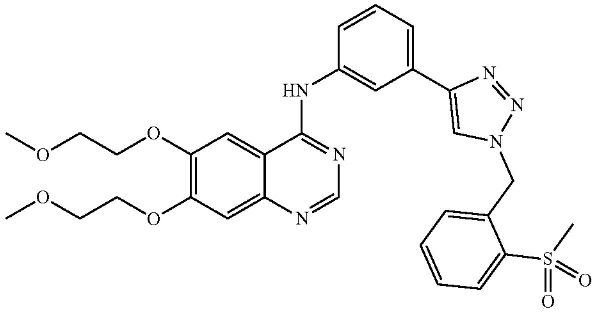 [SMILES: COCCOc1cc2ncnc(Nc3cccc(-c4cn(Cc5ccccc5S(C)(=O)=O)nn4)c3)c2cc1OCCOC] | 604.21 |
| 56 | P12-C8 | 0.978 | 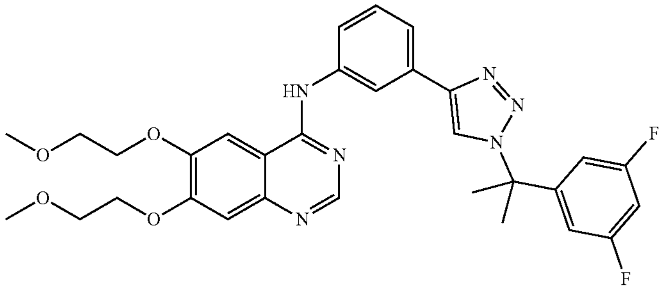 [SMILES: COCCOc1cc2ncnc(Nc3cccc(-c4cn(C(C)(C)c5cc(F)cc(F)c5)nn4)c3)c2cc1OCCOC] | 590.24 |
| 57 | P12-C9 | 0.957 | 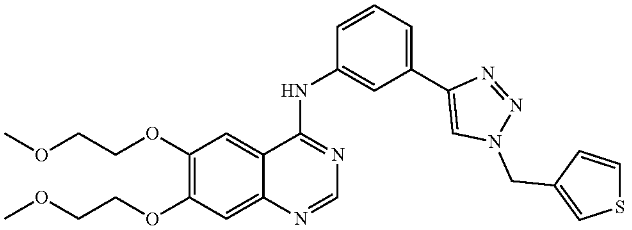 [SMILES: COCCOc1cc2ncnc(Nc3cccc(-c4cn(Cc5ccsc5)nn4)c3)c2cc1OCCOC] | 532.19 |
| 84 | P13-A1 | 0.988 | 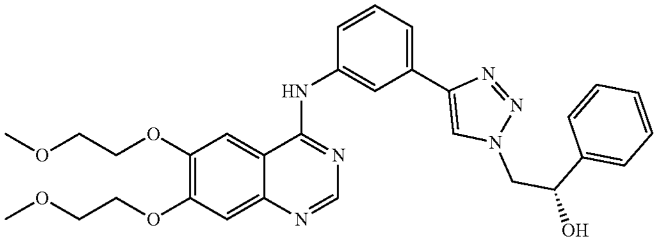 [SMILES: COCCOc1cc2ncnc(Nc3cccc(-c4cn(C[C@@H](O)c5ccccc5)nn4)c3)c2cc1OCCOC] | 556.24 |

TABLE 1-continued
| Serial number of compound | Address in compound library | Relative survival rate | Compound structure | Molecular weight |
|---|---|---|---|---|
| Structure and biological activity of some compounds in high-throughput compound library (relative survival rate = 0.5 ~ 1) | | | | |
| 85 | P13-A5 | 0.867 | 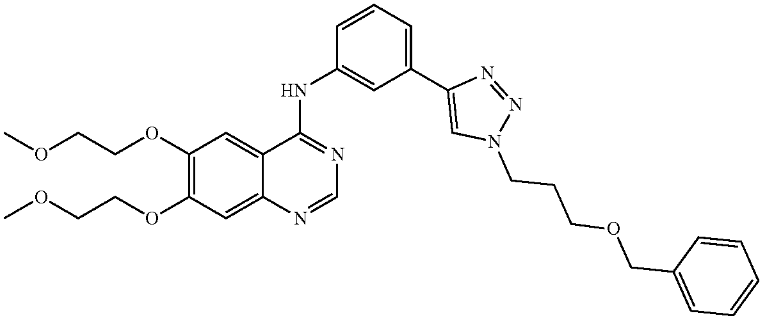 [SMILES: COCCOc1cc2ncnc(Nc3cccc(-c4cn(CCCOCc5ccccc5)nn4)c3)c2cc1OCCOC] | 584.27 |
| 86 | P13-A11 | 0.861 | 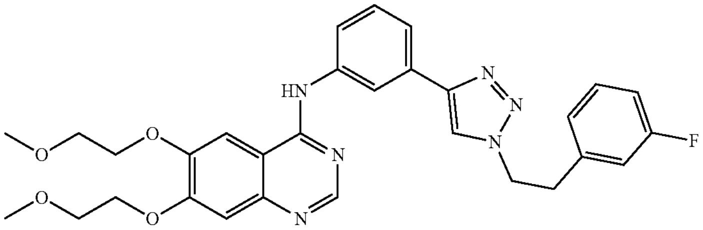 [SMILES: COCCOc1cc2ncnc(Nc3cccc(-c4cn(CCc5cccc(F)c5)nn4)c3)c2cc1OCCOC] | 558.24 |
| 87 | P13-B1 | 0.850 | 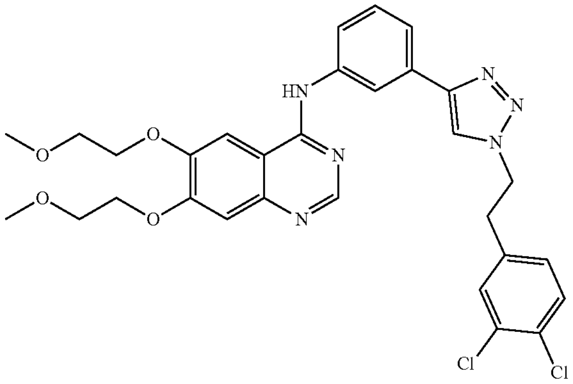 [SMILES: COCCOc1cc2ncnc(Nc3cccc(-c4cn(CCc5ccc(Cl)c(Cl)c5)nn4)c3)c2cc1OCCOC] | 608.17 |
| 88 | P13-B2 | 0.889 | 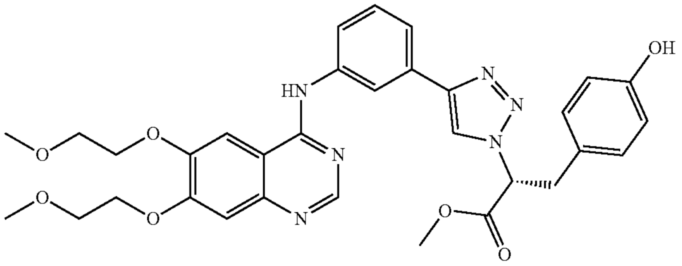 [SMILES: COCCOc1cc2ncnc(Nc3cccc(-c4cn([C@H](Cc5ccc(O)cc5)C(=O)OC)nn4)c3)c2cc1OCCOC] | 614.25 |

TABLE 1-continued
Structure and biological activity of some compounds in high-throughput compound library (relative survival rate = 0.5 ~ 1)
| Serial number of compound | Address in compound library | Relative survival rate | Compound structure | Molecular weight |
|---|---|---|---|---|
| 89 | P13-B6 | 0.577 | 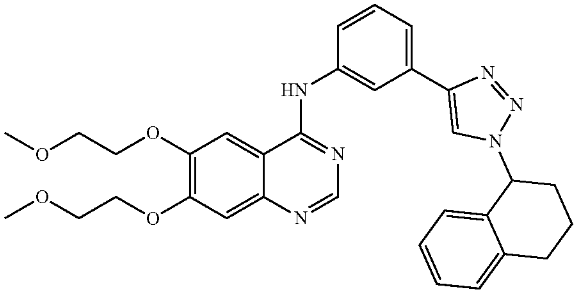 [SMILES: COCCOc1cc2ncnc(Nc3cccc(-c4cn(C5CCCc6ccccc65)nn4)c3)c2cc1OCCOC] | 566.26 |
| 90 | P13-B7 | 0.522 | 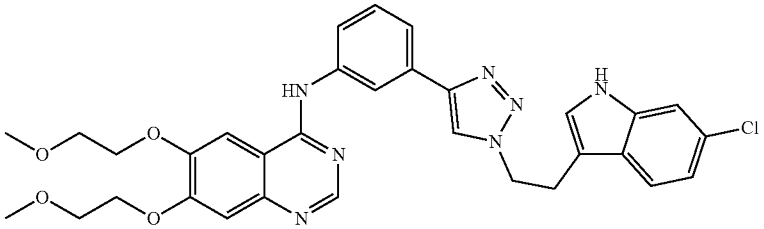 [SMILES: COCCOc1cc2ncnc(Nc3cccc(-c4cn(CCc5c[nH]c6cc(Cl)ccc56)nn4)c3)c2cc1OCCOC] | 613.22 |
| 91 | P13-B8 | 0.574 | 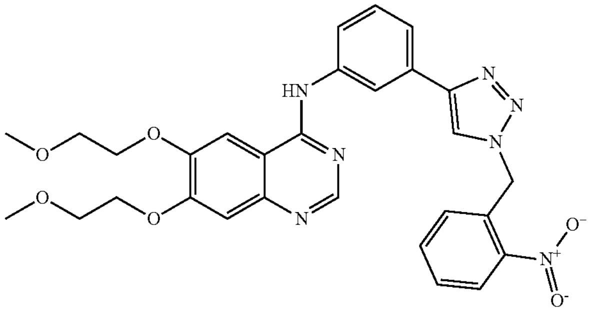 | 571.22 |
| 92 | P13-B10 | 0.854 | 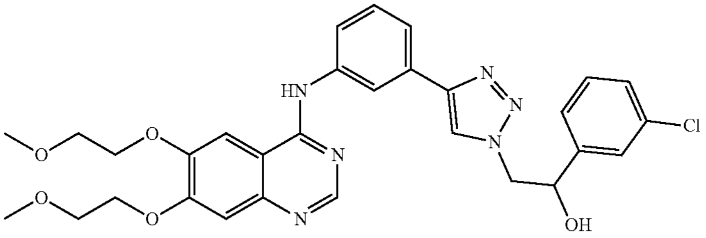 [SMILES: COCCOc1cc2ncnc(Nc3cccc(-c4cn(CC(O)c5cccc(Cl)c5)nn4)c3)c2cc1OCCOC] | 590.20 |
| 93 | P13-C6 | 0.621 | 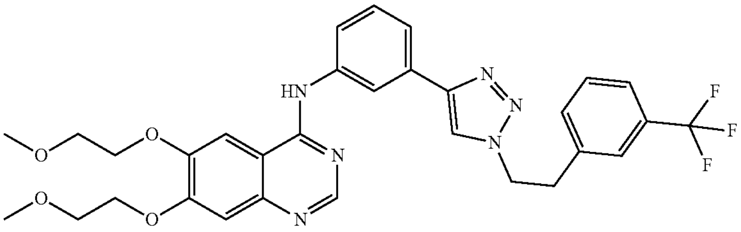 [SMILES: COCCOc1cc2ncnc(Nc3cccc(-c4cn(CCc5cccc(C(F)(F)F)c5)nn4)c3)c2cc1OCCOC] | 608.24 |

TABLE 1-continued
Structure and biological activity of some compounds in high-throughput compound library (relative survival rate = 0.5 ~ 1)
| Serial number of compound | Address in compound library | Relative survival rate | Compound structure | Molecular weight |
|---|---|---|---|---|
| 94 | P13-C7 | 0.885 | 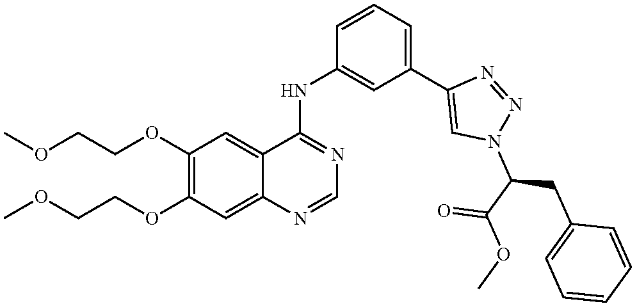 [SMILES: COCCOc1cc2ncnc(Nc3cccc(-c4cn([C@@H](Cc5ccccc5)C(=O)OC)nn4)c3)c2cc1OCCOC] | 598.25 |
| 95 | P13-C8 | 0.971 | 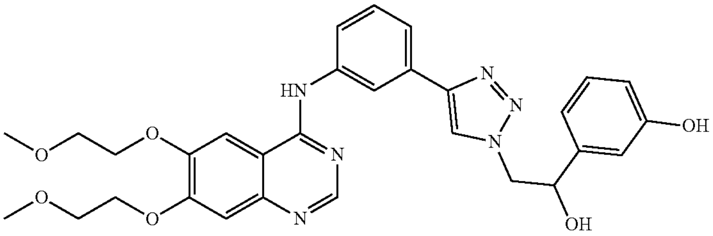 [SMILES: COCCOc1cc2ncnc(Nc3cccc(-c4cn(CC(O)c5cccc(O)c5)nn4)c3)c2cc1OCCOC] | 572.24 |
| 96 | P13-C9 | 0.829 | 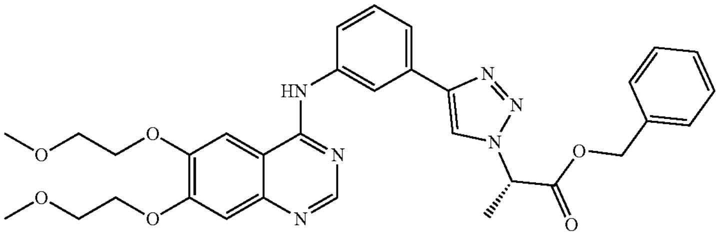 [SMILES: COCCOc1cc2ncnc(Nc3cccc(-c4cn([C@@H](C)C(=O)OCc5ccccc5)nn4)c3)c2cc1OCCOC] | 598.25 |
| 97 | P13-001 | 0.654 | 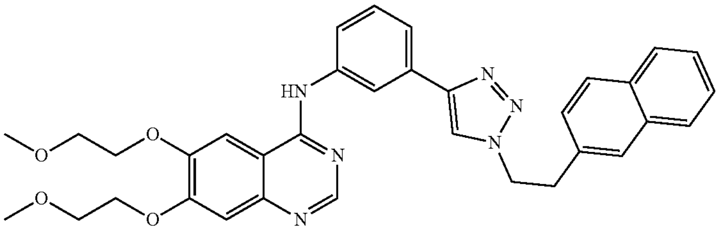 [SMILES: COCCOc1cc2ncnc(Nc3cccc(-c4cn(CCc5ccc6ccccc6c5)nn4)c3)c2cc1OCCOC] | 590.26 |
| 98 | P13-C11 | 0.959 | 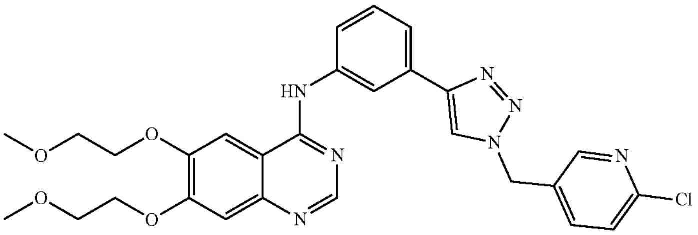 [SMILES: COCCOc1cc2ncnc(Nc3cccc(-c4cn(Cc5ccc(Cl)nc5)nn4)c3)c2cc1OCCOC] | 561.19 |

TABLE 1-continued

| Serial number of compound | Address in compound library | Relative survival rate | Compound structure | Molecular weight |
|---|---|---|---|---|
| Structure and biological activity of some compounds in high-throughput compound library (relative survival rate = 0.5 ~ 1) | | | | |
| 99 | P13-C12 | 0.888 | 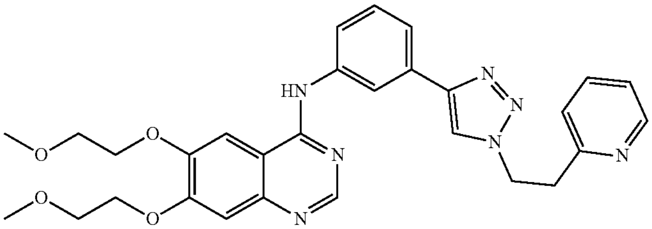 [SMILES: COCCOc1cc2ncnc(Nc3cccc(-c4cn(CCc5ccccn5)nn4)c3)c2cc1OCCOC] | 541.24 |

TABLE 2

| Serial number of compound | Compound library location | Relative survival rate | Compound structure | Molecular weight |
|---|---|---|---|---|
| Structure and biological activity of some compounds in high-throughput compound library (relative survival rate >1) | | | | |
| 266 | P11-A1 | 1.130 | 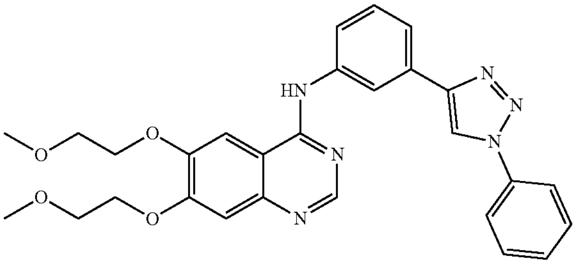 [SMILES: COCCOc1cc2ncnc(Nc3cccc(-c4cn(-c5ccccc5)nn4)c3)c2cc1OCCOC] | 512.22 |
| 267 | P11-A8 | 1.129 | 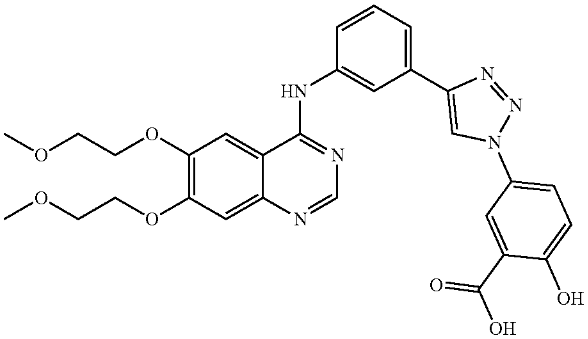 [SMILES: COCCOc1cc2ncnc(Nc3cccc(-c4cn(-c5ccc(O)c(C(=O)O)c5)nn4)c3)c2cc1OCCOC] | 572.20 |
| 268 | P11-C12 | 1.311 | 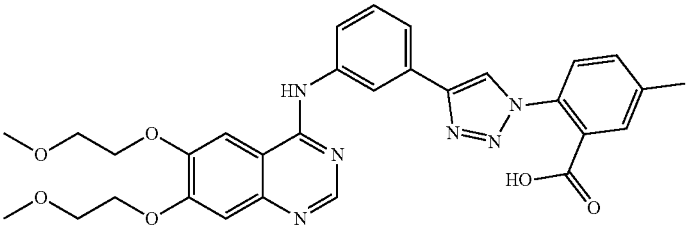 | 570.22 |

TABLE 2-continued

Structure and biological activity of some compounds in high-throughput compound library (relative survival rate >1)

| Serial number of compound | Compound library location | Relative survival rate | Compound structure | Molecular weight |
|---|---|---|---|---|
| 269 | P11-H6 | 1.289 | 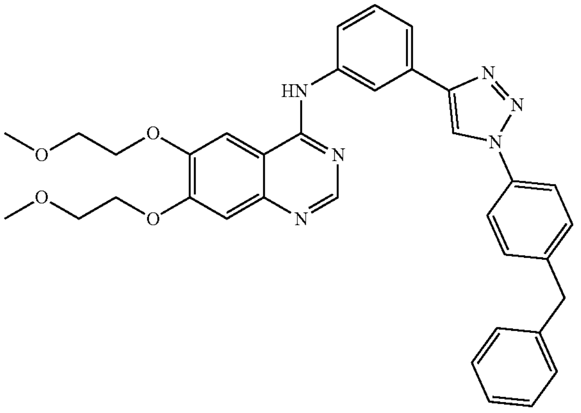 [SMILES: COCCOc1cc2ncnc(Nc3cccc(-c4cn(-c5ccc(Cc6ccccc6)cc5)nn4)c3)c2cc1OCCOC] | 602.26 |
| 270 | P11-H11 | 1.200 | 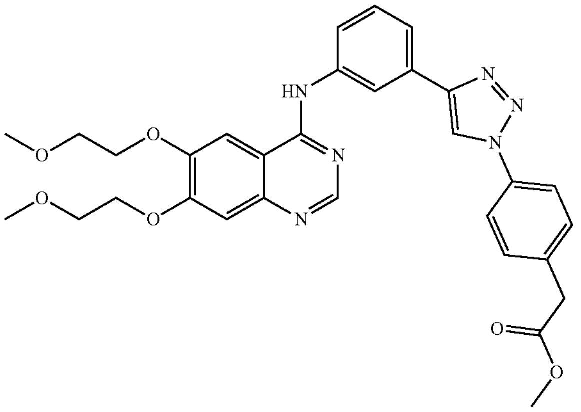 [SMILES: COCCOc1cc2ncnc(Nc3cccc(-c4cn(-c5ccc(CC(=O)OC)cc5)nn4)c3)c2cc1OCCOC] | 584.24 |

The results showed that, the method of/the invention can complete the preparation and screening process of compounds in the same reaction system (or reaction chamber).

Since the two-step reactions were almost quantitative generation of products, the products could be used in enzymology and even cytology test experiments without separation, and it has important application value in the field of high-throughput synthesis and screening of compounds.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for constructing and screening a high-throughput compound library comprising the following steps:

(a) providing a reactor comprising n reaction chambers, wherein the reaction chambers are each independent and addressable, and the n reaction chambers constitute an addressable array of then reaction chambers;

(b) performing m independent synthesis reactions in the n reaction chambers, and obtaining a respective synthetic product in the n reaction chambers in which the synthesis reactions are carried out, thereby constructing and obtaining a compound library; wherein, each of the m independent synthesis reactions, comprises the following steps:

(b0) in an inert solvent, in the presence of a base, reacting a primary amine R—$NH_2$ with $FSO_2N_3$ (fluorosulfonyl azide) to obtain a 1,3-dipolar cyclization reagent R—$N_3$;

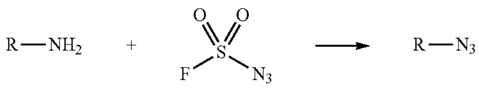

wherein R is $R^1$ or

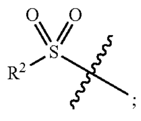

R1 and R2 are each independently drug active fragment, $R^1$ and $R^2$ are each independently substituted or unsubstituted groups selected from the group consisting of alkyl, cycloalkyl, heteroalkyl, heterocyclyl, alkenyl, cycloalkenyl, alkynyl, aryl, heteroaryl, sulfonyl, or a combination thereof; and (b1) in a reaction chamber of then reaction chambers, in an inert solvent, carrying out a 1,3-dipolarcycloaddition reaction with the 1,3-dipolar cyclization reagent R—$N_3$ obtained in b(0) and a reaction substrate containing a terminal unsaturated bond, thereby forming a reaction product containing 1,3-dipolar ring selected from formula II, formula III or formula IV, and the 1,3-dipolarcycloaddition reaction is selected from the group consisting of:

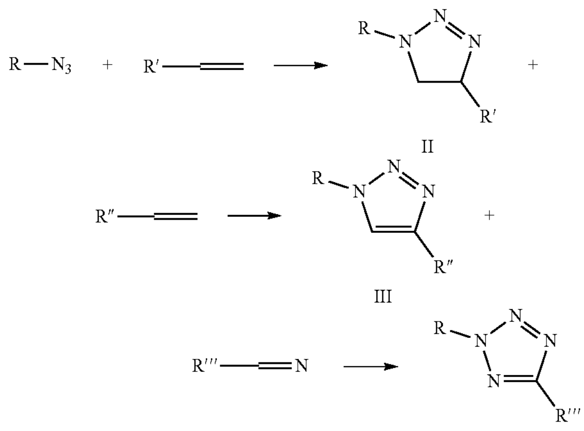

II

III

IV wherein R, R', R" and R"' are each independently $R^1$ or

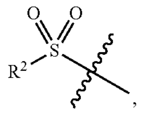

denotes a point of attachment to the terminal unsaturated bond in the reaction substrate selected from the group consisting of R'—CH═$CH_2$, R'—C≡CH, or R'—C≡N; and (c) adding to the synthetic product in each of the n reaction chambers an activity test reagent selected from the group consisting of enzymes, proteins, nucleic acids, cells, small molecule compounds, and combinations thereof, respectively, to carry out an activity test, thereby carrying out activity screening on each synthetic product; wherein, n is a positive integer ≥10, and m is a positive integer ≤n, and m≥10.

2. The method of claim 1, wherein each of the n reaction chambers independently has a volume of 5 microliters (μL) to 5000 μL.

3. The method of claim 1, wherein the activity test reagent is selected from the group consisting of an antibody, an antigen, a ligand, a ligand/receptor binding inhibitor, an angiogenesis inhibitor, a cell adhesion inhibitor, a gene expression inhibitor, an enzyme inhibitor, wherein the enzyme inhibitor is selected from the group consisting of tyrosinase inhibitor, cyclooxygenase inhibitor, telomerase inhibitor, matrix metalloprotein inhibitor, prostaglandin D synthesis inhibitor, phosphodiesterase inhibitor, cholinesterase inhibitor, viral protease inhibitor, reverse transcriptase inhibitor, and combinations thereof.

4. The method of claim 1, further comprising detecting, in each of the n reaction chambers, the presence or absence of a reaction product.

5. The method of claim 1, wherein the 1,3-dipolar cycloaddition reaction is:

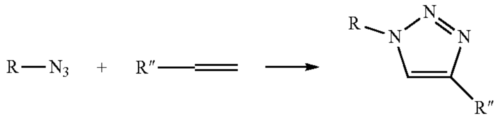

III wherein R and R" are as defined in claim 1.

* * * * *